US012691269B2

(12) United States Patent
Irving et al.

(10) Patent No.: US 12,691,269 B2
(45) Date of Patent: Jul. 28, 2026

(54) INTRANASAL DELIVERY DEVICES AND METHODS OF USE

(71) Applicant: Rocket Science Health Corp., Victoria (CA)

(72) Inventors: Kenneth Irving, Victoria (CA); James Jackson, Victoria (CA); Alec Lillis, Victoria (CA); Manu Sharma, Victoria (CA)

(73) Assignee: Rocket Science Health Corp., Victoria (CA)

( * ) Notice: Subject to any disclaimer, the term of this patent is extended or adjusted under 35 U.S.C. 154(b) by 0 days.

(21) Appl. No.: 19/430,790

(22) Filed: Dec. 23, 2025

(65) Prior Publication Data

US 2026/0115438 A1     Apr. 30, 2026

Related U.S. Application Data

(63) Continuation of application No. PCT/CA2025/050507, filed on Apr. 8, 2025.

(Continued)

(51) Int. Cl.
*A61M 31/00* (2006.01)

(52) U.S. Cl.
CPC ......... *A61M 31/00* (2013.01); *A61M 2206/11* (2013.01); *A61M 2210/0618* (2013.01)

(58) Field of Classification Search
CPC .......... A61M 31/00; A61M 2210/0618; A61M 2210/0681; A61M 2202/0007;

(Continued)

(56) References Cited

U.S. PATENT DOCUMENTS 5,961,489 A * 10/1999 Hirota ................. A61M 11/007
                                                            604/94.01
2007/0119451 A1* 5/2007 Wang ................... A61M 15/08
                                                            128/207.18

(Continued)

FOREIGN PATENT DOCUMENTS

CA          2315381 A1     7/1999
CA          2698137 A1     3/2008

(Continued)

OTHER PUBLICATIONS

International Search Report and Written Opinion received in PCT Application No. PCT/CA25/50507, mailed on Jul. 31, 2025, 12 pages.

*Primary Examiner* — Kevin C Sirmons
*Assistant Examiner* — Alexandra Lalonde
(74) *Attorney, Agent, or Firm* — Mintz, Levin, Cohn, Ferris, Glovsky and Popeo, P.C.

(57) ABSTRACT

The present disclosure describes devices for intranasal drug delivery to targeted regions and sub-regions of a nasal cavity of a subject, including turbinates. The devices may have a housing with a dispensing element, and a positioning or trigger element coupled to the housing that positions the dispensing element within a nasal channel and limits its depth of insertion. The dispensing element may comprise a side opening for dispensing a composition. Devices of the present disclosure may provide a convenient and effective way to deliver compositions intranasally to the targeted regions and sub-regions while limiting off-target delivery.

15 Claims, 53 Drawing Sheets

Related U.S. Application Data

(60) Provisional application No. 63/631,991, filed on Apr. 9, 2024.

(58) Field of Classification Search
CPC .. A61M 11/006; A61M 11/007; A61M 11/06; A61M 15/0003; A61M 15/08; A61M 15/009; A61M 15/008; A61M 2206/11; A61M 5/46; A61M 2205/073; A61M 25/007; A61M 16/0666; A61M 1/682
See application file for complete search history.

(56) References Cited

U.S. PATENT DOCUMENTS

| | | | |
|---|---|---|---|
| 2010/0160897 A1* | 6/2010 | Ducharme | A61M 5/1409 604/82 |
| 2016/0367771 A1 | 12/2016 | Djupesland | |
| 2020/0390989 A1* | 12/2020 | Mazhar | A61M 15/009 |
| 2022/0088327 A1* | 3/2022 | Fuller | A61M 15/009 |

FOREIGN PATENT DOCUMENTS

| | | | |
|---|---|---|---|
| WO | 2024224372 A1 | 10/2024 | |
| WO | 2025213256 A1 | 10/2025 | |

* cited by examiner

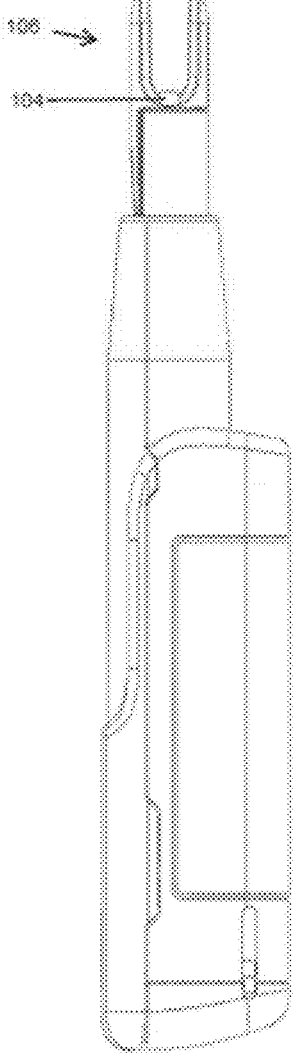
FIG. 2G
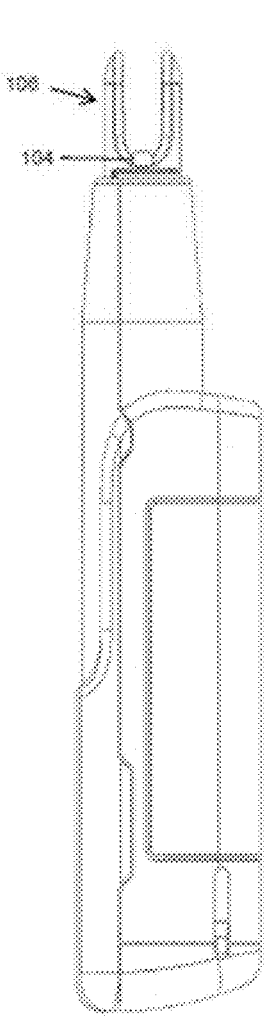
FIG. 2H

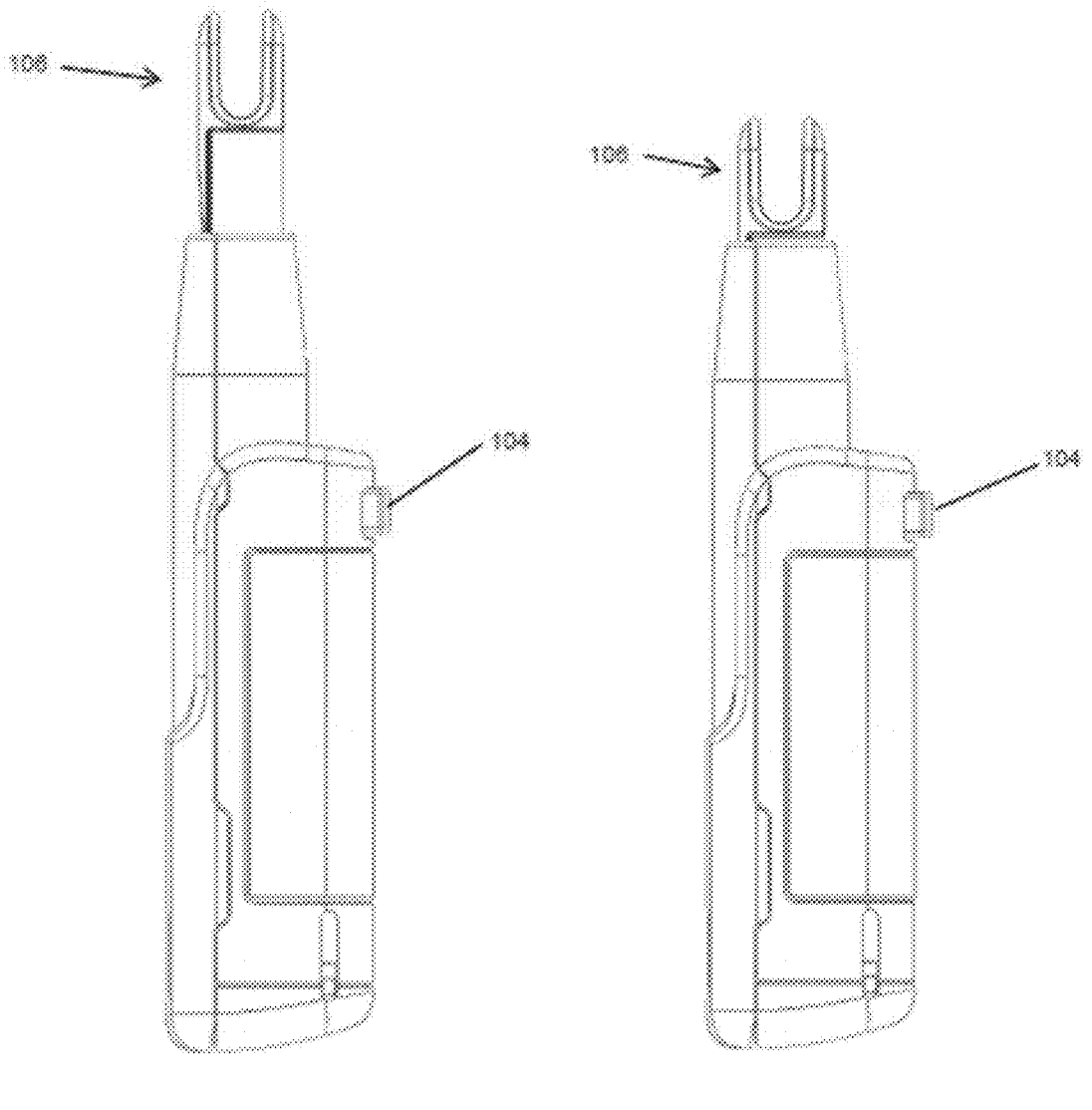
FIG. 2I                              FIG. 2J

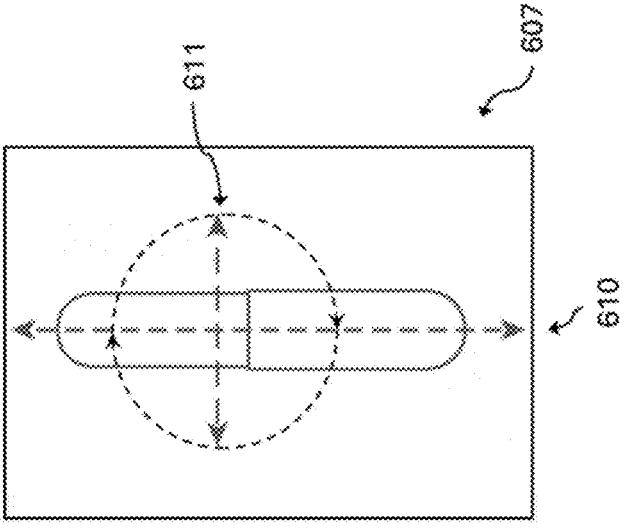
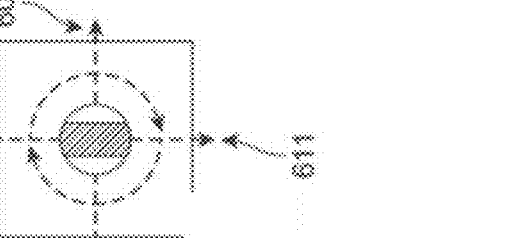
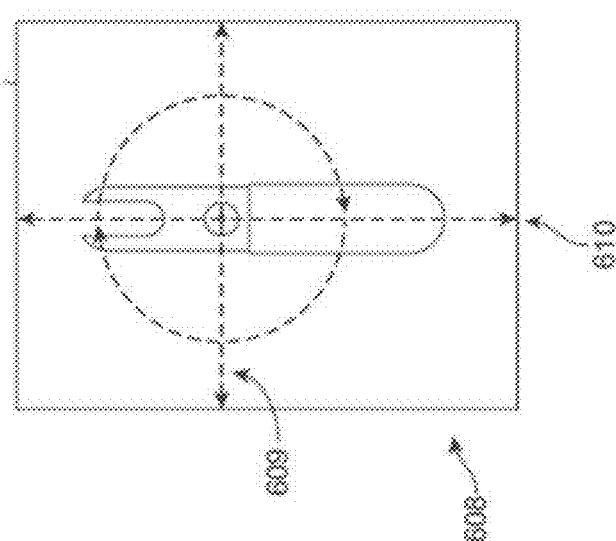
FIG. 6C

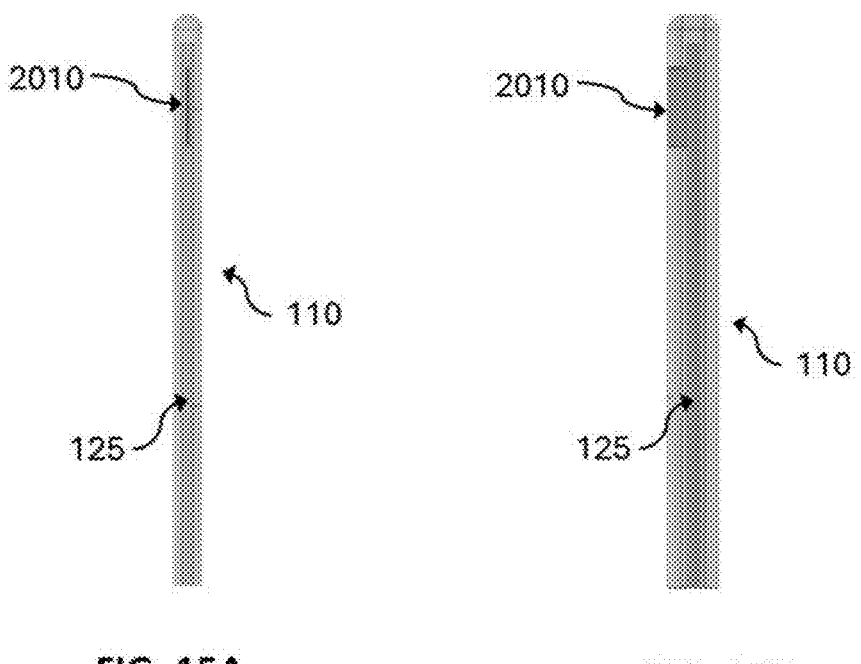
FIG. 15A                    FIG. 15B
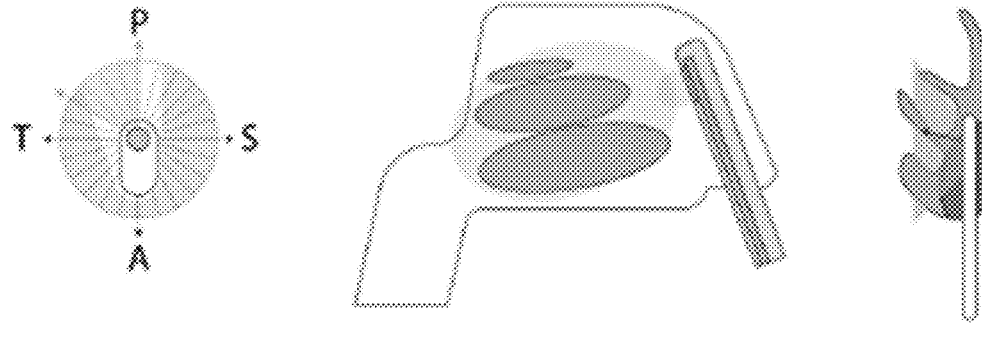
FIG. 16

INTRANASAL DELIVERY DEVICES AND METHODS OF USE

CROSS REFERENCE

This application is a continuation of International Application No. PCT/CA25/050507, filed Apr. 8, 2025, which claims the benefit to U.S. Provisional Application No. 63/631,991, filed Apr. 9, 2024, the content of which is incorporated herein in its entirety by reference.

FIELD

The present disclosure relates generally to an intranasal delivery device, and more specifically, an intranasal delivery device for delivery to targeted intranasal regions and sub-regions such as the turbinates.

BACKGROUND

Intranasal drug delivery is an effective route for the administration of certain medications, for example, those that act locally in the nasal channel, or those that are rapidly absorbed into the bloodstream through the nasal mucosa. The pharmaceutical industry has long recognized the nasal route as an effective means for drug delivery, offering rapid absorption, convenience, and non-invasiveness compared to other methods. Currently, the lower nasal cavity is a focal point for drug deposition, dominating the market due to its significant advantages in drug absorption and effectiveness. Among the challenges associated with delivering compositions to the nasal channel of a subject includes difficulty in accommodating for variations in nasal channel, targeting deposition of the therapeutic compound at the correct location in the nasal channel, and providing a device which can reliably and repeatably deliver a composition to lower nasal regions within the nasal channel with a high degree of precision across a population of subjects.

SUMMARY

It is appreciated by the inventors that difficulties in nasal delivery include anatomical, cognitive, and dexterity related challenges. These challenges must be addressed to provide a reliable and effective nasal delivery device. For example, the internal nasal valve is a flow-limiting segment of the nasal channel bounded medially by the dorsal septum, laterally by the caudal portion of the upper lateral cartilage and inferiorly by the head of the inferior turbinate that together present a physical barrier between the nasal vestibule and the rest of the nasal channel, including the respiratory region and the olfactory cleft. The internal nasal valve is bounded by nasal tissue that can swell or block the path to the nasal channel, which varies based on time of day, environmental factors, and genetically among individuals. Devices may need to be inserted at particular angles or depths in order to target a specific area, and users may struggle with correct placement and actuation of a device. Users with motor skill impairment (e.g., persons with Parkinson's disease, arthritis) or cognitive impairments (e.g., Alzheimer's disease) may especially struggle to correctly articulate, position, and actuate an intranasal delivery device.

To counter such difficulties, this disclosure provides a novel introducer device for targeted delivery of a composition to a target region of a nasal cavity of a subject, which can be readily actuated and positioned by users of various patient populations, and reliably deliver the composition to the target region of the nasal cavity. Exemplary devices utilize a dual nostril inserter with a columella engaging portion positioned therebetween in order to quickly and reliably seat the insertable portions of the device within an ejection zone of a subject's nasal cavity. The exemplary devices disclosed herein can permit for quick, easy, and reliable positioning of a dispensing element within the nasal channel so as to permit for accurate and targeted deposition of compositions to target regions of the nasal cavity. Further, exemplary devices disclosed herein can enable quick, easy, and reliable positioning and targeted deposition across diverse patient populations (e.g., users that are elderly, cognitively impaired, dexterity impaired, or have variations in nasal anatomy), by users of varying skill (e.g., untrained bystanders), under high stress circumstances (e.g., a medical emergency), which may otherwise prevent proper use of intranasal delivery devices.

The devices of the present disclosure may comprise housing comprising one or a combination of the following: a subject engaging portion, one or more insertable portions, one or more dispensing elements, and a trigger.

In one aspect, the disclosure provides a device for intranasal delivery to a subject, the device comprising: a housing comprising an insertable portion comprising a distal end, and a proximal end; a subject engaging portion which engages a columella region of the subject to seat the distal end of the insertable portion within an ejection zone of a nasal channel of the subject. In some embodiments, the ejection zone is: 0 mm to 30 mm superior to a horizontal line that intersects the anterior aspect of the internal nasal valve, and 0 mm to 20 mm anterior to an inclined line that intersects the anterior aspect of the middle turbinate and the posterior aspect of the vestibule, wherein the insertable portion comprises a dispensing element for delivery of a composition to a region or sub-region of the nasal channel of the subject, wherein the dispensing element comprises a side opening.

In one aspect, the disclosure provides a device for intranasal delivery to a subject, the device comprising an insertable portion comprising a distal end, and a proximal end, wherein the device is configured to seat the distal end of the insertable portion within an ejection zone of a nasal channel of the subject, wherein the ejection zone is superior to an internal nasal valve, and wherein delivery from the insertable portion of the device is configured to selectively target a lower nasal region.

In one aspect, the disclosure provides a device for intranasal delivery to a subject, the device comprising: a housing comprising an insertable portion configured for insertion into a nasal channel of the subject; and a subject engaging portion which engages a columella region of the subject coupled to the housing, wherein application of pressure by the subject engaging portion to the columella region of the subject enables and/or causes delivery of a composition to the subject from the insertable portion.

In one aspect, the disclosure provides a device for intranasal delivery to a subject, the device comprising: a housing defining first and second insertable portions, each for insertion into a nasal channel of the subject, wherein, upon insertion of the first insertable portion into the nasal channel of the subject, the at least one insertable portion engages tissue within the nasal channel to open or expand an internal nasal valve of the subject thereby positioning at least one of the insertable portions for delivery of a composition to the subject; and an actuator which delivers the composition from the either or both of the insertable portions when the device is actuated.

In one aspect, the disclosure provides a device for intranasal delivery to a subject, the device transitionable from a first configuration to a second configuration, the device comprising: a housing defining a first insertable portion configured to be inserted into a nasal channel of the subject; and a dispensing element coupled to the housing, the dispensing element revealing from the first insertable portion upon transition of the device from the first configuration to the second configuration, wherein the device is transitioned from the first configuration to the second configuration by application of pressure about a longitudinal axis of the device, and wherein the device is simultaneously actuated upon being transitioned from the first configuration to the second configuration.

In one aspect, the disclosure provides a device for intranasal delivery to a subject, the device transitionable from a first configuration to a second configuration, the device comprising: a housing defining two insertable portions comprising at least one dispensing element, each insertable portion for insertion into a nasal channel of the subject, wherein, upon insertion of the first insertable portion into a nasal channel of the subject, the first insertable portion engages tissue within the nasal channel to open or expand an internal nasal valve of the subject thereby positioning at least one of the dispensing elements for delivery of a composition to the subject; a subject engaging portion coupled to the housing comprising a trigger, the trigger comprising a subject engaging portion which engages a columella region, wherein upon application of pressure to the subject engaging portion, the trigger permits actuation of the device to deliver a composition to the subject from the dispensing element; and the dispensing element revealing from the first insertable portion upon transition of the device from the first configuration to the second configuration.

In some embodiments, the insertable portion comprises a dispensing element for delivery of a composition to a region or sub-region of the nasal channel of the subject. In some embodiments, the region or sub-region comprises one or more turbinates. In some embodiments, the region or sub-region comprises a middle turbinate.

In some embodiments, the dispensing element is configured to dispense the composition from a side opening.

In one aspect, the disclosure provides a method for intranasal delivery to a subject with a device, the method comprising: positioning a dispensing element within an ejection zone of a nasal cavity of the subject; and dispensing a composition from a side opening of the dispensing element.

In one aspect, the disclosure provides a method for intranasal delivery to a subject with a device, the method comprising: positioning an insertable portion of the device within an ejection zone of a nasal cavity of the subject by engaging a columella region of the subject with a subject engaging portion of the device, seating the insertable portion within the ejection zone of the subject's nasal cavity, wherein the ejection zone is: 0 mm to 30 mm superior to a horizontal line that intersects the anterior aspect of the internal nasal valve, and 0 mm to 20 mm anterior to an inclined line that intersects the anterior aspect of the middle turbinate and the posterior aspect of the vestibule, and one or more of the following: 0 mm to 40 mm inferior to a horizontal line that is parallel to the inferior aspect of the olfactory cleft, 0 mm to 20 mm posterior to the internal nasal dorsum, 10 mm to 50 mm superior to a horizontal line that intersects the inferior aspect of the columella, 0 mm to 30 mm superior to a horizontal line that intersects the superior aspect of the inferior turbinate, 0 mm to 3 mm from the septum, or any combination thereof.

In one aspect, the disclosure provides a method for intranasal delivery to a subject with a device, the method comprising: inserting two insertable portions into nasal channels of the subject, wherein upon the inserting at least one of the insertable portion engages tissue within the nasal channel thereby opening or expanding an opening of an internal nasal valve of the subject, thereby positioning at least one of the insertable portions for delivery of a composition to the subject.

In one aspect, the disclosure provides a method for intranasal delivery to a subject with a device, the method comprising: positioning an insertable portion of the device within a nasal channel of the subject; and transitioning the device from a first configuration to a second configuration by applying pressure about a longitudinal axis of the device, thereby revealing a dispensing element from the first insertable portion and simultaneously actuating the device to deliver the composition to the subject.

In one aspect, the disclosure provides a method for intranasal delivery of a composition to a target region of the nasal cavity of a subject, the method comprising: inserting a dispensing element into an ejection zone of a nasal cavity, wherein the ejection zone is: 0 mm to 30 mm superior to a horizontal line that intersects the anterior aspect of the internal nasal valve, and 0 mm to 20 mm anterior to an inclined line that intersects the anterior aspect of the middle turbinate and the posterior aspect of the vestibule, and one or more of the following: 0 mm to 40 mm inferior to a horizontal line that is parallel to the inferior aspect of the olfactory cleft, 0 mm to 20 mm posterior to the internal nasal dorsum, 10 mm to 50 mm superior to a horizontal line that intersects the inferior aspect of the columella, 0 mm to 30 mm superior to a horizontal line that intersects the superior aspect of the inferior turbinate, 0 mm to 3 mm from the septum, or any combination thereof, and dispensing the composition from the dispensing element to contact the target region with the composition, wherein dispensing the composition from the ejection zone: a) increases on target delivery of the composition to the target region, b) decreases off target delivery of the composition to the nasal cavity, or c) both.

The devices and methods of the present disclosure provide several advantages over existing intranasal drug delivery devices. For example, the device is easy to use and provides precise, consistent, and effective drug delivery. Additionally, the device is capable of accurately delivering drugs to the target site within the nasal channel, resulting in several therapeutic benefits, for example, reduced drug loss, minimized off-target effects, improved comfort, greater compliance, improved subject experience, and improved therapeutic outcomes.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings.

FIG. 2G depicts an exemplary embodiment front view of another Exemplary Device in the first configuration, according to some embodiments.

FIG. 2H depicts an exemplary embodiment front view of an Exemplary Device in the second configuration, according to some embodiment.

FIG. 2I depicts an exemplary embodiment front view of another Exemplary Device in the first configuration, according to some embodiments.

FIG. 2J depicts an exemplary embodiment front view of an Exemplary Device in the second configuration, according to some embodiment.

FIG. 6C depicts an exemplary embodiment of (left to right) a front Coronal Plane, a top Transverse Plane, and a back Sagittal Plane view, according to some embodiments.

FIGS. 15A-15B depicts a cannula modified for targeted delivery to the lower nasal cavity, having an ejection port (e.g. a kiss-cut or other type of cut) cut through a side of the cannula to the inner lumen, for off-axis ejection. Length of the cut/opening can be varied to open or focus deposition height, and/or target specific anatomies of the nasal cavity. Velocity can be modified to open or focus deposition length, and/or target specific anatomies of the nasal cavity. Position of the ejection port (Superior/inferior) can be modified to target specific anatomies of the nasal cavity. Position of the ejection port (Medial/lateral) can be modified to target specific anatomies of the nasal cavity. Velocity can be modified or varied to achieve different types of impinging jet profiles resulting in varied deposition profiles (eg. Bolus Deposition, surface coating deposition, and droplet deposition). (A) Front view. (B) Side view.

FIG. 16 depicts schematic illustrations of an example of turbinate deposition. A lateral ejection port is cut in a turbinate side of a cannula from about 0 to 50 degrees. The length of the cut is about 5 to 10 mm. The fluid velocity for this example is about 6 to 12+m/s. The position of the ejection port for this example is about 30 mm from the columella. The deposition type is droplet or sheet/surfacer. The impingement type is wide early distribution.

DETAILED DESCRIPTION

Figure 1A:
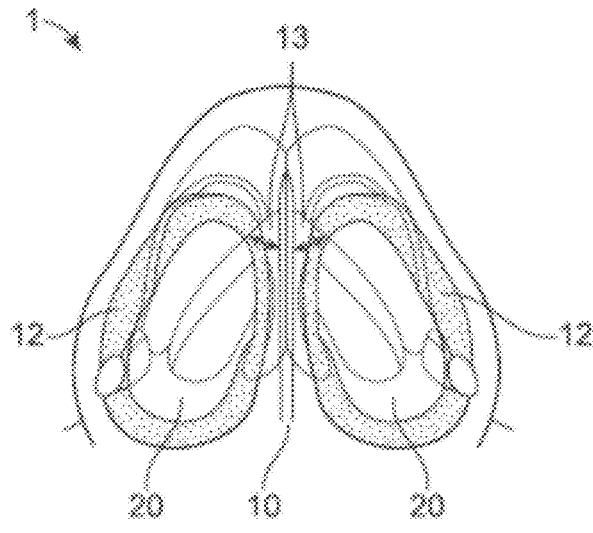
FIG. 1A depicts a bottom view of an exemplary embodiment of a subject's nose.

The nasal cavity is comprised of a nasopharyngeal region and two nasal channels, separated by the septum, each comprising a vestibule, a respiratory region, and an olfactory cleft. It is appreciated by the inventors that there are a number of difficulties in facilitating intranasal delivery of therapeutic compositions including anatomical, cognitive, and dexterity related challenges depending on the subject population. For example, the internal nasal valve is a flow-limiting segment of the nasal channel bounded medially by the dorsal septum, laterally by the caudal portion of the upper lateral cartilage and inferiorly by the head of the inferior turbinate that together present a physical barrier between the nasal vestibule and the rest of the nasal channel, including the respiratory region and the olfactory cleft. The internal nasal valve is bounded by nasal tissue that can swell or block the path to the nasal channel, which varies based on time of day, environmental factors, and genetically among individuals. Devices may need to be inserted at particular angles or depths in order to target a specific area, and users may struggle with correct placement and actuation of a device. Users with motor skill impairment (e.g., persons with Parkinson's disease, arthritis) or cognitive impairments (e.g., Alzheimer's disease) may especially struggle to correctly articulate, position, and actuate an intranasal delivery device.

To counter such difficulties, this disclosure provides a novel introducer device for targeted delivery of a composition to a target region of a nasal cavity of a subject, which can be readily actuated and positioned by users of various patient populations, and reliably deliver the composition to the target region of the nasal cavity. Exemplary devices utilize a dual nostril inserter with a columella engaging portion positioned therebetween in order to quickly and reliably seat the insertable portions of the device within an ejection zone of a subject's nasal cavity. The exemplary devices disclosed herein can permit for quick, easy, and reliable positioning of a dispensing element within the nasal channel so as to permit for accurate and targeted deposition of compositions to target regions of the nasal cavity. Further, exemplary devices disclosed herein can enable quick, easy, and reliable positioning and targeted deposition across diverse patient populations (e.g., users that are elderly, cognitively impaired, dexterity impaired, or have variations in nasal anatomy), by users of varying skill (e.g., untrained bystanders), under high stress circumstances (e.g., a medical emergency), which may otherwise prevent proper use of intranasal delivery devices The devices of the present disclosure may comprise a subject engaging portion that engages a columella region of a subject and one or more insertable portions that open or expand one or both internal nasal valves of a subject, with the subject engaging portion thereby properly positioning either one or more insertable portions, or one or more dispensing elements of the device, within an ejection zone for targeted delivery of a composition to one or more specific areas of the nasal cavity, such as one or both middle meatuses, or one or both middle turbinates. The subject engaging portion can engage the columella region about one or both sides of the columella region, may comprise a saddle or concave shape, and may slide onto the columella region such that the device uses the columella region as a depth datum and the nasal dorsum line as an angular reference for positioning the insertable portions and/or dispensing elements at a desired depth and orientation within the ejection zone. Such a subject engaging portion utilizing the columella region as a depth datum and the nasal dorsum line as an angular reference, can permit for the placement of the device, and dispensing of a composition there from, to a targeted area of one or both nasal cavities in a reproduceable manner across a population of subjects. For example, subjects of differing anatomy, backgrounds, cognitive abilities, and motor skills may be able to position the device in approximately the same position within one or both nasal channels. The columella region and the nasal dorsum line can position the introducer device to achieve precise and consistent positioning of either one or both insertable portions and/or one or both dispensing elements within one or both nasal channels. By relying on the columella region and the nasal dorsum line, a reliable reference point is established that can be used across different populations and anthropometric variances. This eliminates the need for subject-specific tuning or measurements, making the process more efficient, accurate, cost-effective, and user friendly. The subject engaging portion may comprise or be coupled to an actuator, trigger, or both which actuates or permits the device to be actuated and dispense a composition when pressure is applied to the user's columella region by the subject engaging portion or when pressure is applied to the subject engaging portion by the user's columella. The devices of the present disclosure may further comprise one or more insertable portions which are inserted into one or both nasal channels of a subject and open or expand one or both internal nasal valves by pushing the upper lateral cartilage and surrounding tissue up and away from the septum and define a path through which the composition can be delivered to one or more target areas of one or both of the subject's nasal channels such as the meatuses, e.g., the middle meatus, or one or both middle turbinates.

The one or more insertable portions may travel along the nasal channel advancing along the inner nasal dorsum and the septum until the subject engaging portion contacts the columella region. The one or more insertable portions may use the columella region as a depth datum and the nasal dorsum line as an angular reference. The one or more insertable portions may align with the nasal dorsum line. The one or more insertable portions may be configured to follow the shape of inner nasal dorsum, and lateral aspects of the septum, allowing them to maintain a consistent and repeatable angle on a sagittal plane. The form of the one or more insertable portions may be configured to hold them to, and guide them along, the soft tissues of the inner nasal dorsum, ensuring that they remain parallel to these tissues. The device may further comprise one or more dispensing elements that emerge from or are revealed by the one or more insertable portions when the device is transitioned from a first position to a second position (e.g., from a first configuration to a second configuration).

Such features may serve to permit for the design of a universal intranasal delivery device that is usable across a wide variety of subject populations and anthropometric variances. For example, using the columella region and the nasal dorsum as a datum to position the one or more insertable portions within the subject's nasal channels achieves precise and consistent positioning of the insertable portions and the dispensing elements within the nasal cavity. Further, in some cases, when the device comprises, a trigger coupled to the subject engaging portion which is actuated by applying pressure to the columella region with the subject engaging portion, it permits for an easy administration of a composition to one or more nasal channels without the user having to use a digit to actuate the device or the user having to be concerned with the proper alignment or insertion depth of the device within the nasal channels. Such easy administration permitted by the devices of the present disclosure may enable subjects with limited cognitive abilities (e.g., dementia subjects), subjects with limited motor skills (e.g., arthritis subjects), or users in high stress situations (e.g., paramedics, medical personnel, or untrained bystanders treating an overdose victim) to reliably, conveniently, and quickly make use of the targeted intranasal delivery devices disclosed herein to accurately and reliably deliver a composition to a target region of a nasal cavity. Similarly, the one or more insertable portions can align closely with the septum preventing the one or more dispensing elements that extend therefrom or are revealed thereby from snagging or catching on tissue within the nasal channels, while also pushing away hair in the nasal channels and minimizing the likelihood of a sneeze reflex that may negatively impact administration. In some cases, the one or more insertable portions that enable comfortable and accurate insertion into and past the internal nasal valve by moving the upper lateral cartilage up and away from the septum—as needed depending on user anatomy and conditions, can permit for highly targeted delivery to the meatuses, e.g., the middle meatus, the turbinates, or other regions of the nasal anatomy, with one or more dispensing elements that extend from or are revealed by one or more insertable portions in the direction of the meatuses, e.g., the middle meatus, the turbinates, or other regions of the nasal anatomy, thereby enabling accurate delivery of a composition to the meatuses, e.g., the middle meatus, the turbinates, or other regions of the nasal anatomy. The revealing of the one or more dispensing elements only upon insertion of the device may also reduce fear associated with inserting a thin object deep into the nasal channel for certain users.

Embodiments of the present disclosure include an intranasal drug delivery device with a housing comprising one or a combination of the following: a subject engaging portion, one or more insertable portions, one or more dispensing elements, and a trigger. The subject engaging portion engages the columella region of a subject with a columella saddle to seat the distal end of the insertable portion within an ejection zone of a nasal channel of the subject, allowing for accurate positioning of the device in one or both nasal channels, wherein the ejection zone 29 is: 0 mm to 30 mm superior to a horizontal line 627 that intersects the anterior aspect of the internal nasal valve, and 0 mm to 20 mm anterior to an inclined line that intersects the anterior aspect of the middle turbinate and the posterior aspect of the vestibule. The one or more insertable portions move the upper lateral cartilage up and away from the septum of a subject's nasal channels, allowing a composition, upon actuation of the device, to be accurately delivered from the one or more insertable portions to one or more targeted areas in the nasal channels such as the meatuses, e.g., the middle meatus, or the middle turbinates. The one or more dispensing elements, either independently or upon being extended from or revealed by one or more insertable portions, deliver a composition, upon actuation of the device, accurately to one or more areas of the nasal channels such as the meatuses, e.g., the middle meatus, or the middle turbinates. The trigger actuates the device, either by the subject applying pressure on the subject engaging portion against the columella region, or by the subject directly applying pressure to a trigger release.

As used herein composition may include therapeutic compounds (small and large molecules, vaccines, biologics, antibodies, peptides, oligonucleotides, psychedelics, etc), medicaments in liquid form or gas form, or combination thereof. The columella region comprises the columella, a subnasale, or an anterior nasal spine, or a combination thereof. A dispensing element comprises a cannula or a catheter, an insertable portion, a syringe, a fluid chamber, or a combination thereof, or anything that acts upon the cannula or the catheter, the syringe, or the fluid chamber. In some embodiments, the end of the dispensing element is coextensive with the end of the insertable portion when the device is fully actuated.

Figure 1B:
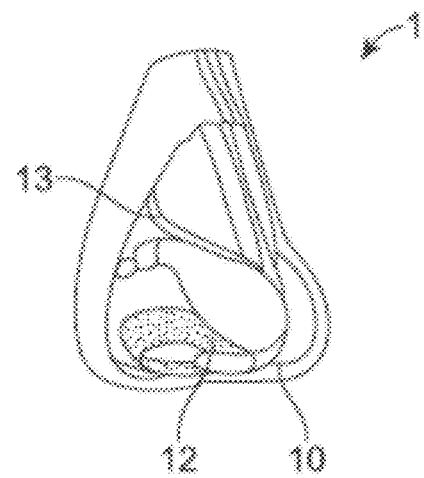
FIG. 1B depicts a side view of an exemplary embodiment of a subject's nose.

FIG. 1A depicts a bottom view of an exemplary embodiment of a subject's nose. FIG. 1B depicts a side view of an exemplary embodiment of a subject's nose. The nose 1 has a columella region 10 between the entrance to two nasal channels 20, an external nasal valve 12 coupled to the nasal channel 20, and an internal nasal valve 13 (INV) coupled to the nasal channel 20.

Figure 1C:
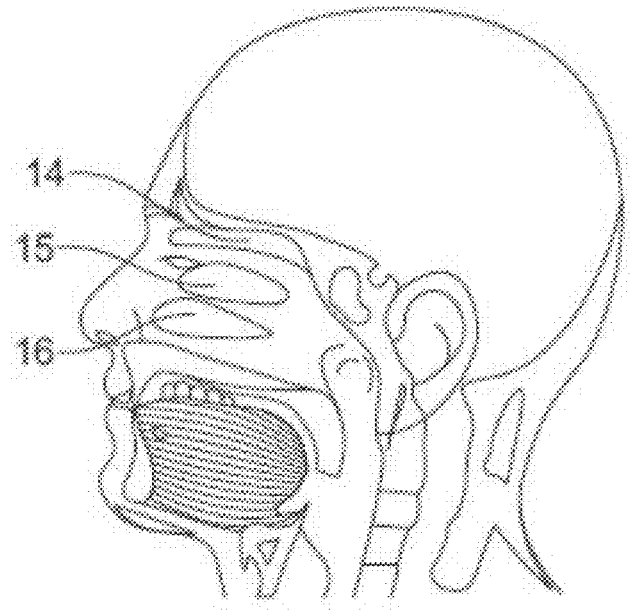
FIG. 1C depicts a side view of a side view of a representation subject's nasal channel.
Figure 1D:
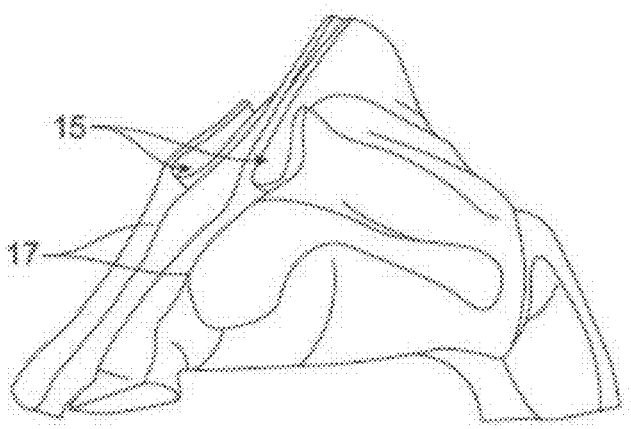
FIG. 1D depicts an exemplary embodiment of a representation subject's nasal channels from the vestibule to the olfactory cleft based on a posteriorly oriented plane.
Figure 1E:
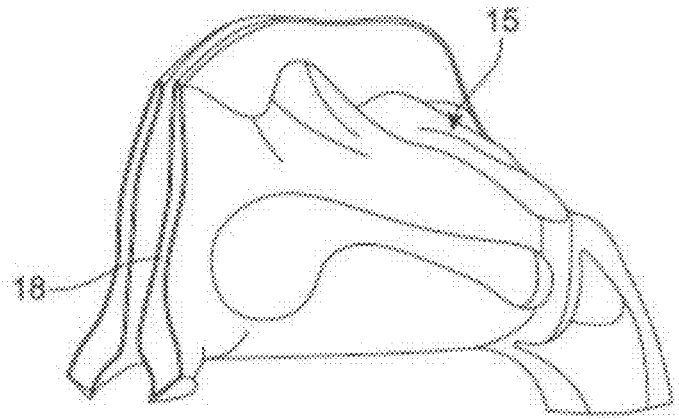
FIG. 1E depicts an exemplary embodiment of a representation subject's nasal channels from the vestibule to the olfactory cleft based on an anteriorly oriented plane.
Figure 1F:
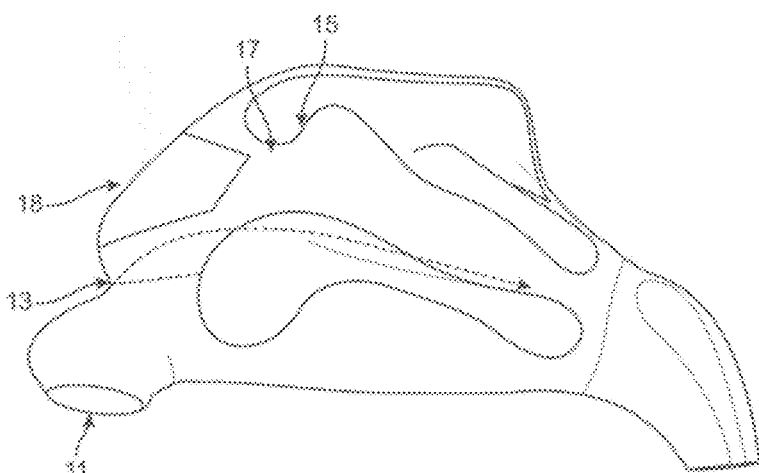
FIG. 1F depicts a side view of an exemplary embodiment of a representation an ejection zone, according to some embodiments.
Figure 1G:
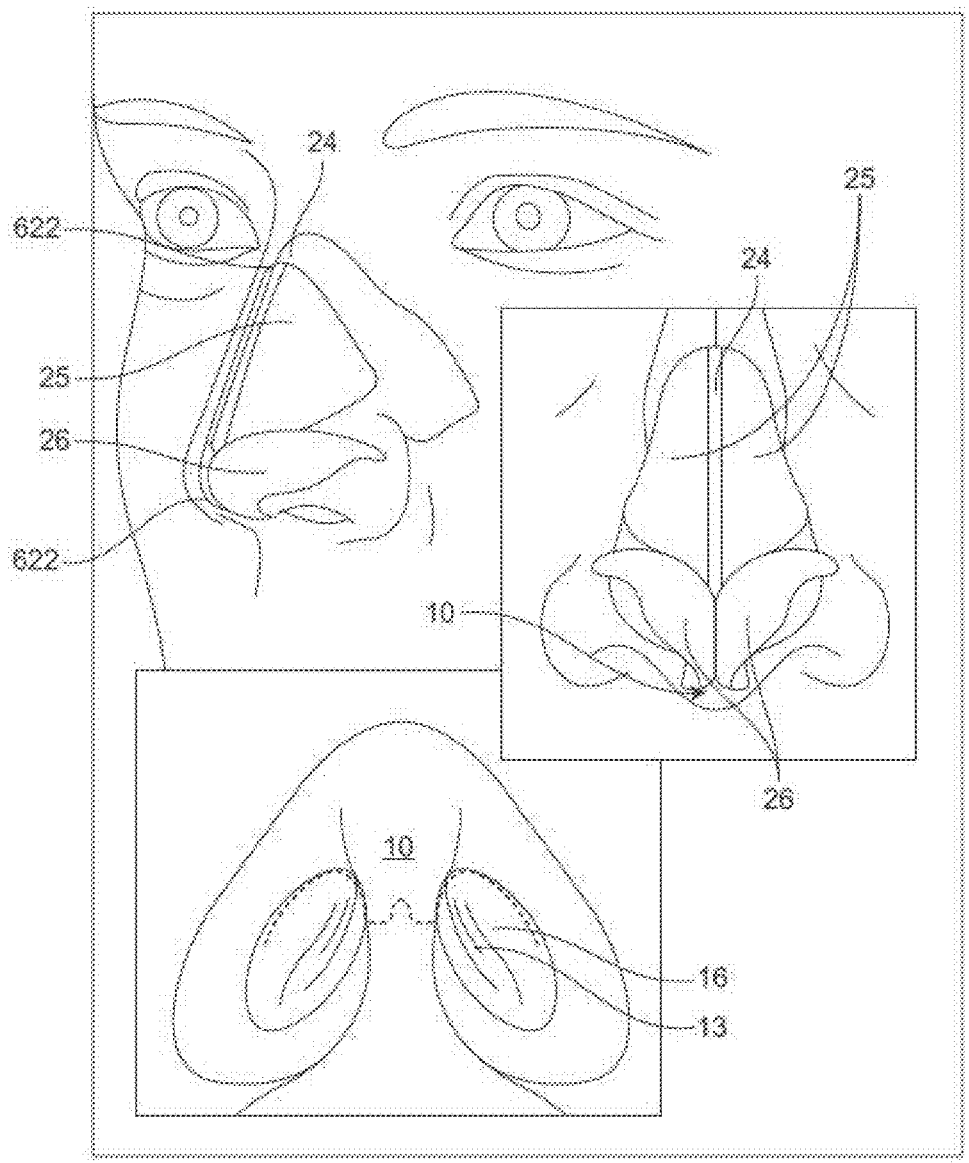
FIG. 1G depicts a front, base and perspective view of an exemplary embodiment of a subject's nose and the columella region.

FIG. 1C depicts a side view of an exemplary embodiment of a subject's nasal cavity showing an inferior turbinate 16, a middle turbinate 15, and a superior turbinate 14. FIG. 1D depicts an angled side view of an exemplary embodiment of a representation subject's nasal channels 20 from the vestibules 21 to the olfactory clefts 23 based on a first plane intersecting at least one posterior pathway 17 showing the middle turbinates 15. FIG. 1E depicts an angled side view of an exemplary embodiment of a representation subject's nasal channels 20 from the vestibules to the olfactory clefts based on a second plane intersecting at least one anterior pathway 18. FIG. 1F depicts a side view of an exemplary embodiment of a representative subject's target region 19. FIG. 1G depicts a front, base and perspective view of an exemplary embodiment of a representative subject's nose exposing the columella region 10. The respiratory regions comprise turbinates that present physical obstacles to delivery to the upper reaches of a nasal channels 20, e.g., the olfactory clefts 23. Each respiratory region comprises at least one superior turbinate 14. Each respiratory region comprises at least one middle turbinate 15. Each respiratory region comprises at least one inferior turbinate 16. Each respiratory region comprises at least one posterior pathway 17 that involves at least one middle turbinate 15. Each respiratory region comprises at least one anterior pathway 18 that does not involve at least one middle turbinate 15.

Figure 1H:
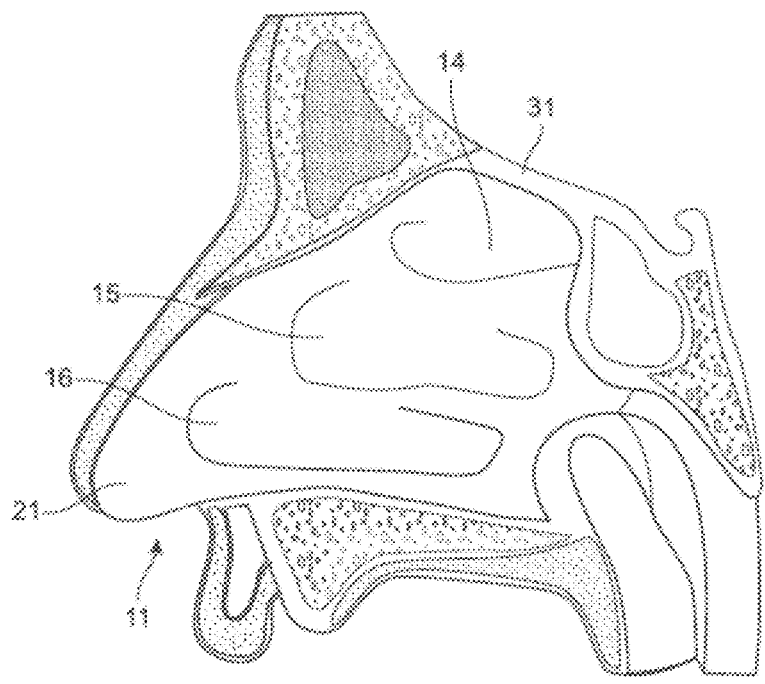
FIG. 1H depicts a side view of an exemplary embodiment of a representation subject's nasal cavity, including internal anatomical features.

FIG. 1H depicts a side view of an exemplary embodiment of a representative subject's nasal cavity. In some cases, the subject's nasal cavity 11 comprises the nasal vestibule 21, inferior turbinate 16, middle turbinate 15, superior turbinate 14, cribriform plate 31 or a combination thereof.

Figure 1I:
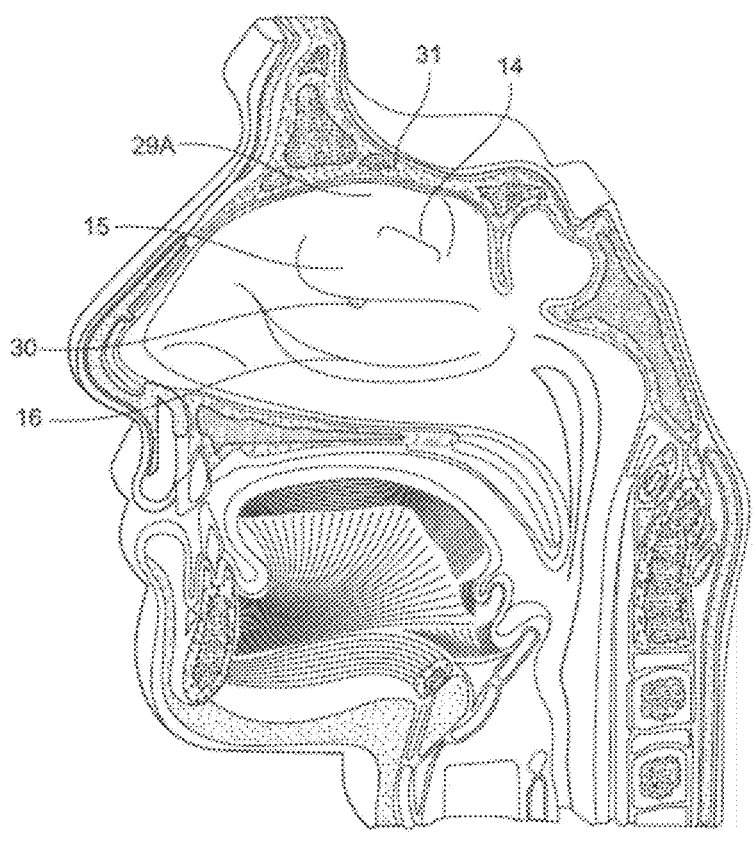
FIG. 1I depicts a side view of an exemplary embodiment of a representation subject's sinus, according to some embodiments.

FIG. 1I depicts a side view of an exemplary embodiment of a representative subject's sinus. In some cases, the subject's sinus comprises the inferior turbinate 16, middle turbinate 15, superior turbinate 14, cribriform plate 31, middle meatus 30, or a combination thereof.

Figure 1J:
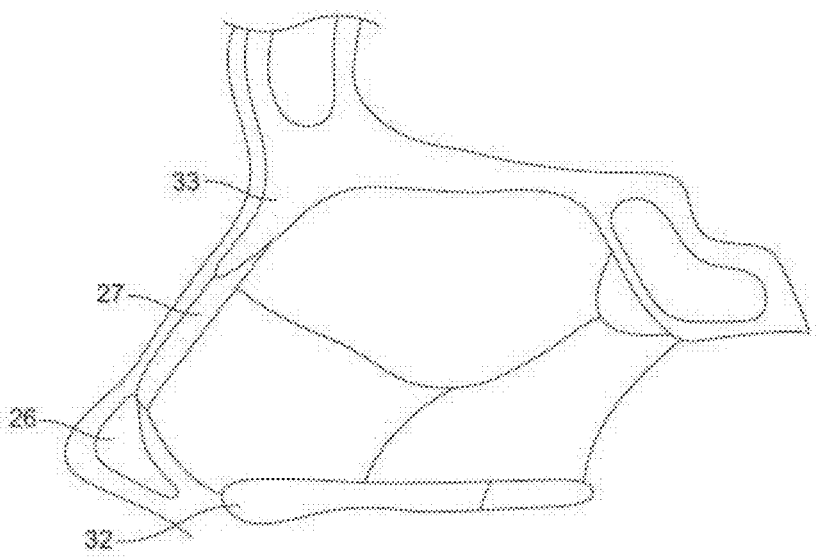
FIG. 1J depicts a side view of a subject's nasal cavity.

FIG. 1J depicts a side view of an exemplary embodiment of a representative subject's nasal cavity. In some embodiments, the nasal cavity 11 comprises the nasal bone 33, septal-lateral cartilage junction 27, lower lateral cartilage 26, anterior nasal spine 32, or a combination thereof.

In one aspect, provided herein is a device for intranasal delivery to a subject, the device comprising an insertable portion 107 comprising a distal end 128, and a proximal end 127, wherein the device is configured to seat the distal end 128 of the insertable portion 107 within an ejection zone 29 of a nasal channel 20 of the subject, wherein the ejection zone 29 is superior to an internal nasal valve 13, and wherein delivery from the insertable portion 107 of the device is configured to selectively target a lower nasal region.

In one aspect, provided herein is a device for intranasal delivery to a subject, the device comprising: a housing 101 defining an insertable portion 107 configured for insertion into a nasal channel 20 of the subject, the insertable portion 107 comprising a distal end 128, and a proximal end 127; a subject engaging portion 106 coupled to the proximal end 127 of the insertable portion 107, the subject engaging portion 106 for engaging a columella region 10 of the subject, thereby seating the insertable portion 107 such that the distal end 128 of the insertable portion 107 is positioned within an ejection zone 29 of the nasal channel 20 of the subject, wherein the ejection zone 29 is: (i) 0 mm to 30 mm superior to a horizontal line 627 that intersects the anterior aspect of the internal nasal valve, and (ii) 0 mm to 20 mm anterior to an inclined line that intersects the anterior aspect of the middle turbinate 15 and the posterior aspect of the vestibule 21.

In one aspect, the disclosure provides a device for intranasal delivery to a subject, the device comprising: a housing 101 comprising an insertable portion 107 configured for insertion into a nasal channel 20 of the subject; and a subject engaging portion 106 which engages a columella region 10 of the subject coupled to the housing 101, wherein application of pressure by the subject engaging portion 106 to the columella region 10 of the subject enables and/or causes delivery of a composition 111 to the subject from the insertable portion 107.

In one aspect, the disclosure provides a device for intranasal delivery to a subject, the device comprising: a housing 101 defining first and second insertable portions 107, each for insertion into a nasal channel 20 of the subject, wherein, upon insertion of the first insertable portion 107 into the nasal channel 20 of the subject, the at least one insertable portion 107 engages tissue within the nasal channel 20 to open or expand an internal nasal valve 13 of the subject thereby positioning at least one of the insertable portions 107 for delivery of a composition 111 to the subject; and an actuator which delivers the composition 111 from the either or both of the insertable portions 107 when the device is actuated.

In one aspect, the disclosure provides a device for intranasal delivery to a subject, the device transitionable from a first configuration 100 to a second configuration 200, the device comprising: a housing 101 defining a first insertable portion 100 configured to be inserted into a nasal channel 20 of the subject; and a dispensing element 110 coupled to the housing 101, the dispensing element 110 revealing from the first insertable portion 107 upon transition of the device from the first configuration 100 to the second configuration 200, wherein the device is transitioned from the first configuration 100 to the second configuration 200 by application of pressure about a longitudinal axis 610 of the device, and wherein the device is simultaneously actuated upon being transitioned from the first configuration 100 to the second configuration 200.

In one aspect, the disclosure provides a device for intranasal delivery to a subject, the device transitionable from a first configuration 100 to a second configuration 200, the device comprising: a housing 101 defining two insertable portions 107 comprising at least one dispensing element 110, each insertable portion for insertion into a nasal channel 20 of the subject, wherein, upon insertion of the first insertable portion 107 into a nasal channel 20 of the subject, the first insertable portion 107 engages tissue within the nasal channel 20 to open or expand an internal nasal valve 13 of the subject thereby positioning at least one of the dispensing elements 110 for delivery of a composition 111 to the subject; a subject engaging portion 106 coupled to the housing 101 comprising a trigger, the trigger comprising a subject engaging portion 106 which engages a columella region 10, wherein upon application of pressure to the subject engaging portion 106, the trigger permits actuation of the device to deliver a composition 111 to the subject from the dispensing element 110; and the dispensing element 110 revealing from the first insertable portion 107 upon transition of the device from the first configuration 100 to the second configuration 200.

In one aspect, the disclosure provides a device for intranasal delivery to a subject, the device transitionable from a first configuration 100 to a second configuration 200, the device comprising: a housing 101 defining two insertable portions 107, each insertable portion 107 for insertion into a nasal channel 20 of the subject for delivery of a composition 111 into a nasal channel 20 of the subject, wherein, upon insertion of the first insertable portion 107 into a nasal channel 20 of the subject, the first insertable portion 107 engages tissue within the nasal channel 20 to open or expand an internal nasal valve 13 of the subject thereby positioning at least one of the insertable portions 107 for delivery of a composition 111 to the subject; and a subject engaging portion 106 coupled to the housing comprising a trigger, the trigger comprising a subject engaging portion 106 which engages a columella region 10, wherein upon application of pressure to the subject engaging portion 106, the trigger permits actuation of the device to deliver a composition 111 to the subject from at least one of the insertable portions 107.

Referring to FIGS. 7A-7E, in some embodiments, the subject engaging portion 106 limits a depth of insertion of the insertable portion 107 into the nasal channel 20. In some embodiments, the insertable portion 107 incorporates one or more dispensing channels 125 leading to one or more dispensing ports 126 configured for delivery of a composition 111 to one or more regions or sub-regions of the nasal channel 20 of the subject. In some embodiments, the insertable portion 107 comprises a dispensing element 110 for delivery of a composition 111 to a region or sub-region of the nasal channel 20 of the subject. In some embodiments, wherein the housing 101 comprises a trigger, upon application of pressure to the trigger, the trigger actuates the device to dispense a composition 111 to the subject from the insertable portion 107 or the dispensing element 110. In some embodiments, the subject engaging portion 106 comprises a trigger coupled to the housing 101 and the subject engaging portion 106, and upon application of pressure of the subject engaging portion 106 to the columella region 10, the trigger actuates the device to dispense a composition 111 to the subject from the insertable portion 107 or the dispensing element 110. In some embodiments, the subject engaging portion 106 comprises a trigger release 104 coupled to the housing 101 and the subject engaging portion 106, and upon application of pressure of the subject engaging portion 106 to the columella region 10, the trigger release 104 permits actuation of the device to deliver a composition 111 to the subject from the insertable portion 107 or the dispensing element 110. In some embodiments, the device further comprises a trigger which is actuatable upon engagement of the trigger release 104. In some embodiments, wherein the housing 101 defines two insertable portions 107, each for insertion into a nasal channel 20 of the subject, wherein, upon insertion of the first insertable portion 107 into a nasal channel 20 of the subject, the first insertable portion 107 engages tissue within the nasal channel 20 to open or expand an internal nasal valve 13 of the subject thereby positioning at least one of the insertable portions 107 for delivery of a composition 111 to the subject within the ejection zone. The device can further include an actuator which delivers a composition 111 from the either or both of the insertable portions 107 when the device is actuated. In some embodiments, wherein the housing 101 defines two insertable portions 107, each for delivery of a composition 111 into a nasal channel 20 of the subject, the device further comprising an actuator which delivers the composition 111 from either or both of the insertable portions 107 when the device is actuated. In some embodiments, wherein the device is transitionable from a first configuration 100 to a second configuration 200, the device further comprising one or two dispensing elements 110 coupled to the insertable portion 107, the at least one dispensing element 110 revealing from the at least one insertable portion 107 upon transition of the device from the first configuration 100 to the second configuration 200.

In some embodiments, the device is transitionable from the first configuration 100 to the second configuration 200 upon application of pressure about a longitudinal axis 610 of the device, wherein the at least one dispensing element 110 reveals in a linear vector relative to a longitudinal axis 610 of the at least one insertable portion 107, or wherein the device is configured to be transitioned from the first configuration 100 to the second configuration 200 with only one hand. In some embodiments, the device is simultaneously actuated upon being transitioned from the first configuration 100 to the second configuration 200. In some embodiments, the distal aspect 131 of the at least one dispensing element 110 is positioned in the ejection zone 29 when the device is in the second configuration 200.

In one aspect, the disclosure provides a device for intranasal delivery to a subject, the device comprising: a housing 101 comprising a dispensing element 110; a subject engaging portion 106 coupled to the housing 101, wherein the subject engaging portion 106 engages a columella region 10, wherein the subject engaging portion 106 positions a dispensing element 110 within a nasal channel 20 of the subject and limits a depth of insertion of the dispensing element 110 into the nasal channel 20. In some embodiments, the subject engaging portion 106 comprises a columella saddle 121, wherein the columella saddle 121 comprises a "U" or "saddle" shape adapted for engaging the columella region 10 of a subject. In some embodiments, the device comprises at least one insertable portion 107. In some embodiments, the device comprises two insertable portions 107, each for insertion into a nasal channel 20 of the subject. In some embodiments, the subject engaging portion 106 engages the columella region 10 of the subject about multiple sides of the columella region 10 in a concave shape. In some embodiments, the at least one dispensing element 110 emerges from or is revealed by the at least one insertable portion 107 upon transition of the device from the first configuration 100 to the second configuration 200. In some embodiments, the housing 101 defines an external shell of the device. In some embodiments the housing comprises a first portion 102, wherein the first portion 102 defines part of the outer shell of the device. In some embodiments, the device comprises a trigger release 104. In some embodiments, the trigger release 104 actuates the ejection mechanism, which in turn delivers a composition 111 from the device. In some embodiments, the trigger release 104 engages an actuation mechanism, which in turn actuates the composition 111 ejection mechanism. In some embodiments, the trigger release 104 may comprise safety or locking mechanisms. In some embodiments, the device is actuated by the user's application of force onto the trigger release 104. In some embodiments, the user may use any digit to actuate the device.

Figure 2A:
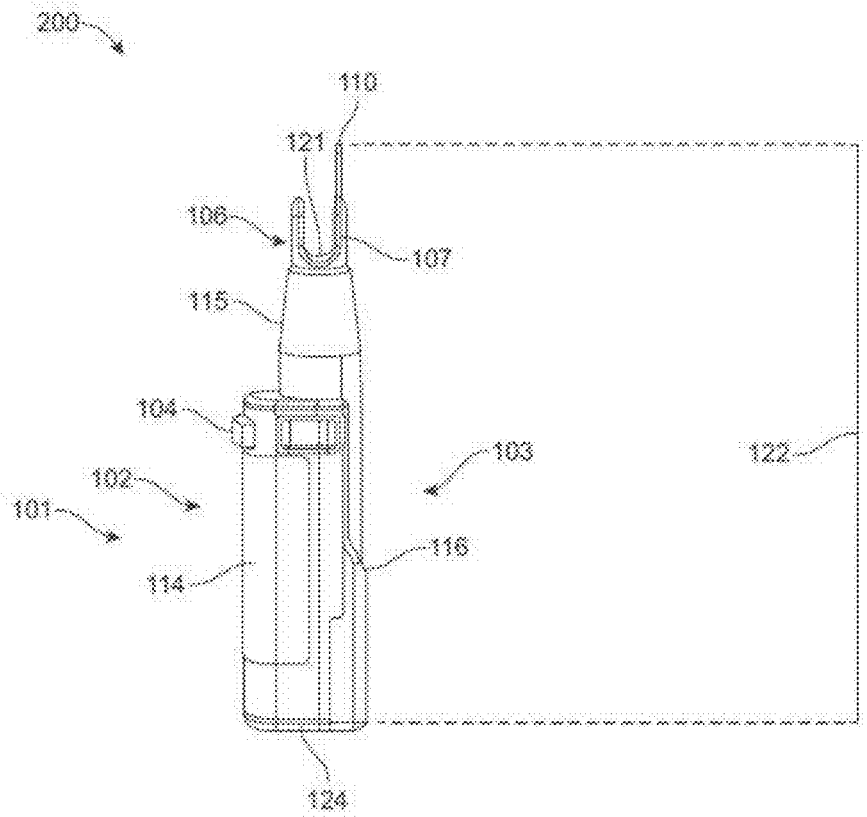
FIG. 2A depicts an exemplary embodiment of an Exemplary Device in a second configuration, according to some embodiments.
Figure 2B:
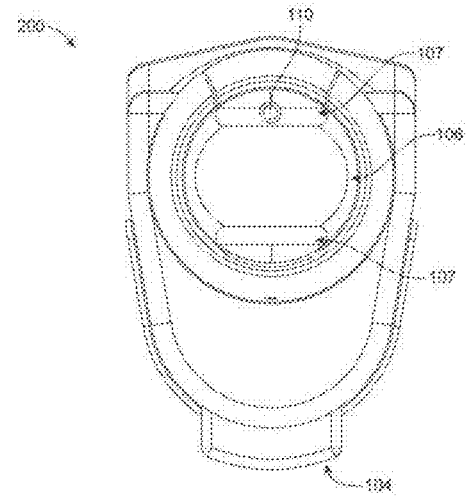
FIG. 2B depicts an exemplary embodiment top view of an Exemplary Device in the second configuration, according to some embodiments.
Figure 2C:
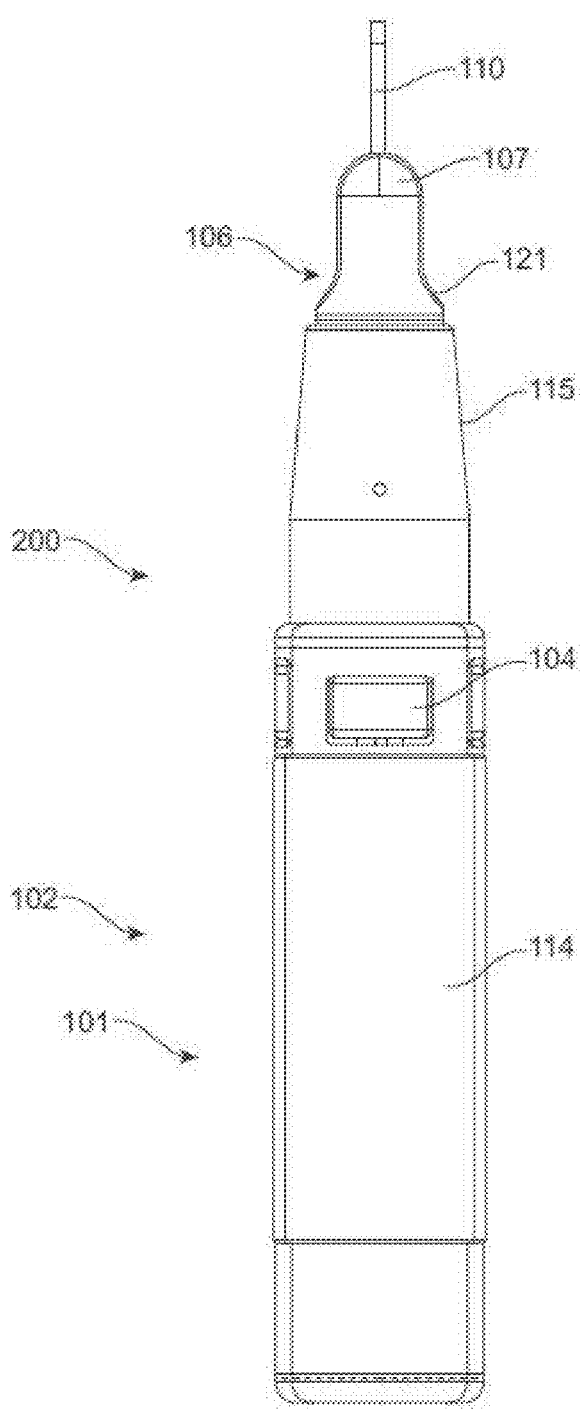
FIG. 2C depicts an exemplary embodiment trigger release side view of an Exemplary Device in the second configuration, according to some embodiments.
Figure 2D:
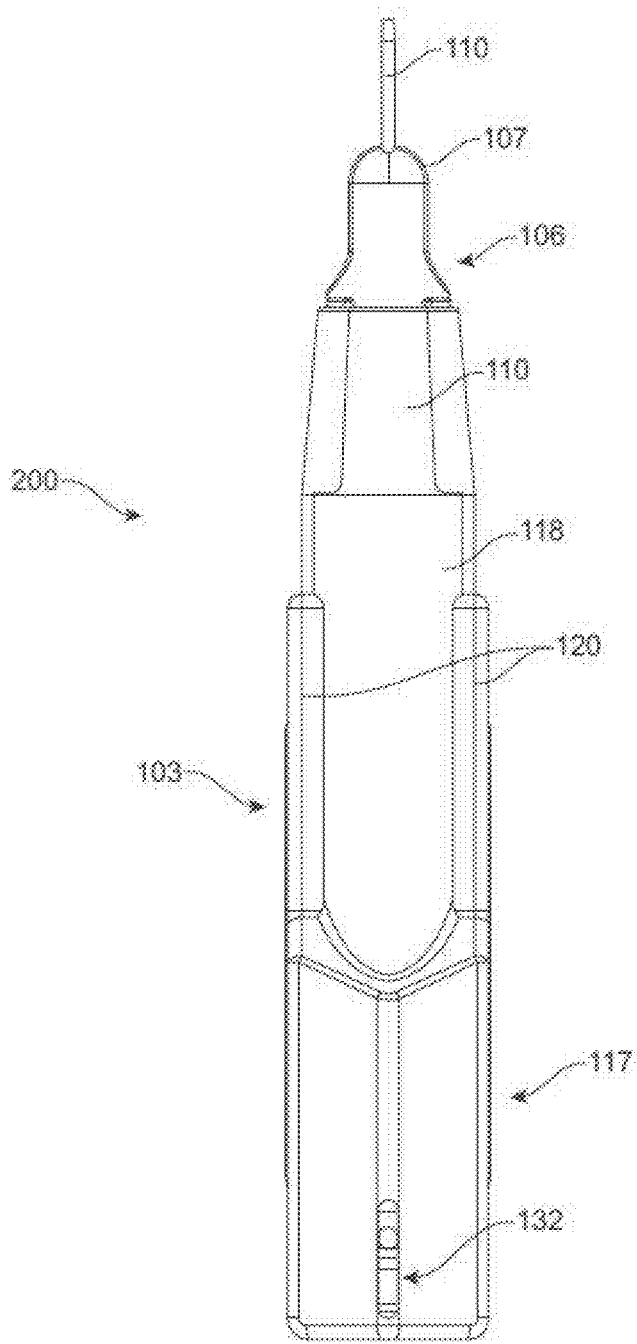
FIG. 2D depicts an exemplary embodiment chassis side view of an Exemplary Device in the second configuration, according to some embodiments.
Figure 2E:
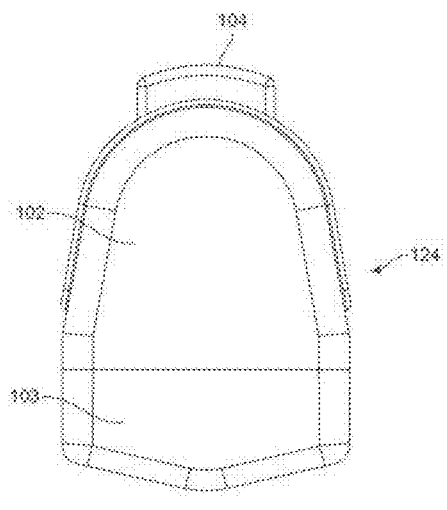
FIG. 2E depicts an exemplary embodiment bottom view of an Exemplary Device in the second configuration, according to some embodiments.
Figure 2F:
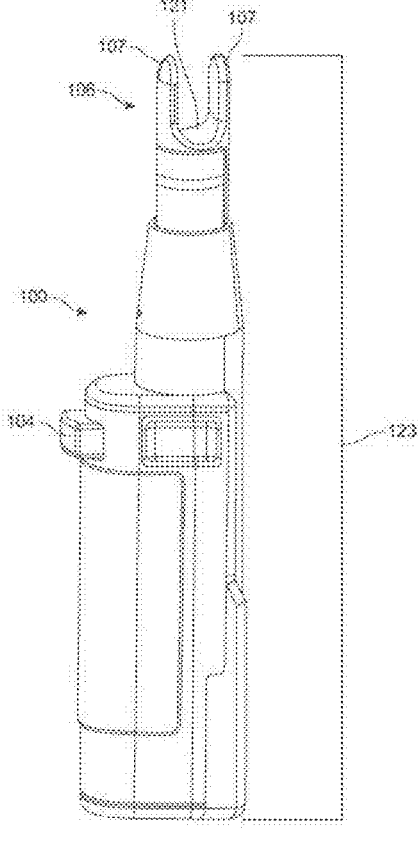
FIG. 2F depicts an exemplary embodiment perspective view of an Exemplary Device in the first configuration, according to some embodiments.
Figure 3A:
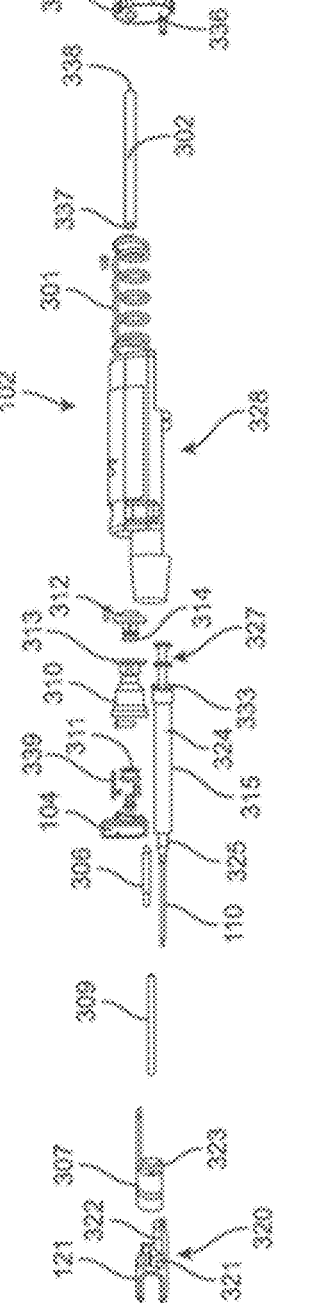
FIG. 3A depicts an exploded view of an Exemplary Device without a chassis, according to some embodiments.
Figure 3B:
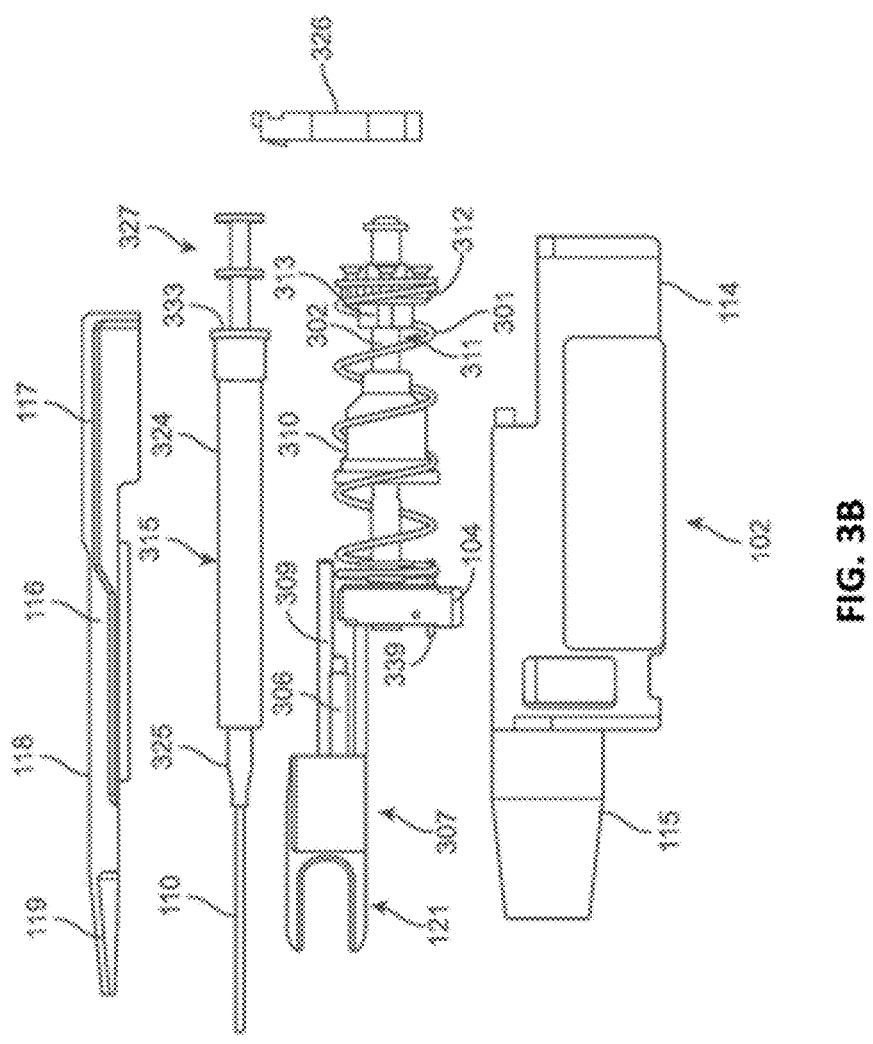
FIG. 3B depicts an exploded view of an Exemplary Device, according to some embodiments.
Figure 3C:
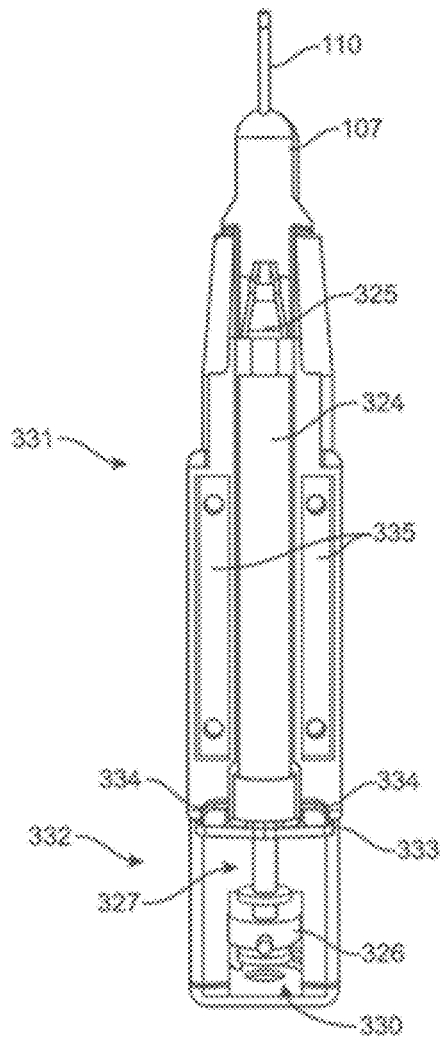
FIG. 3C depicts a cross sectional view of an Exemplary Device without a chassis, according to some embodiments.
Figure 3D:
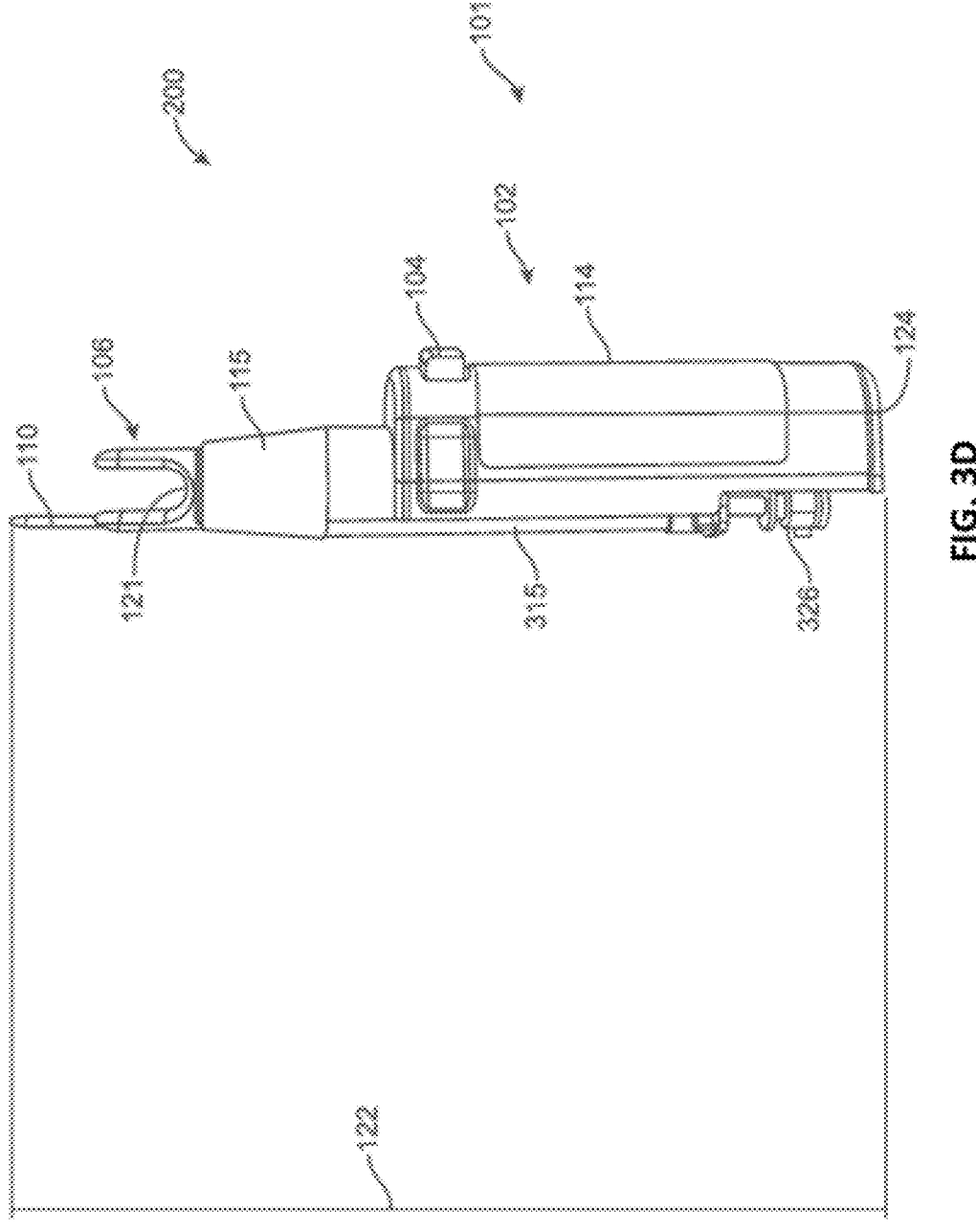
FIG. 3D depicts a forward view with internal components displayed of an Exemplary Device in a second configuration with one dispensing element revealed, according to some embodiments.
Figure 4A:
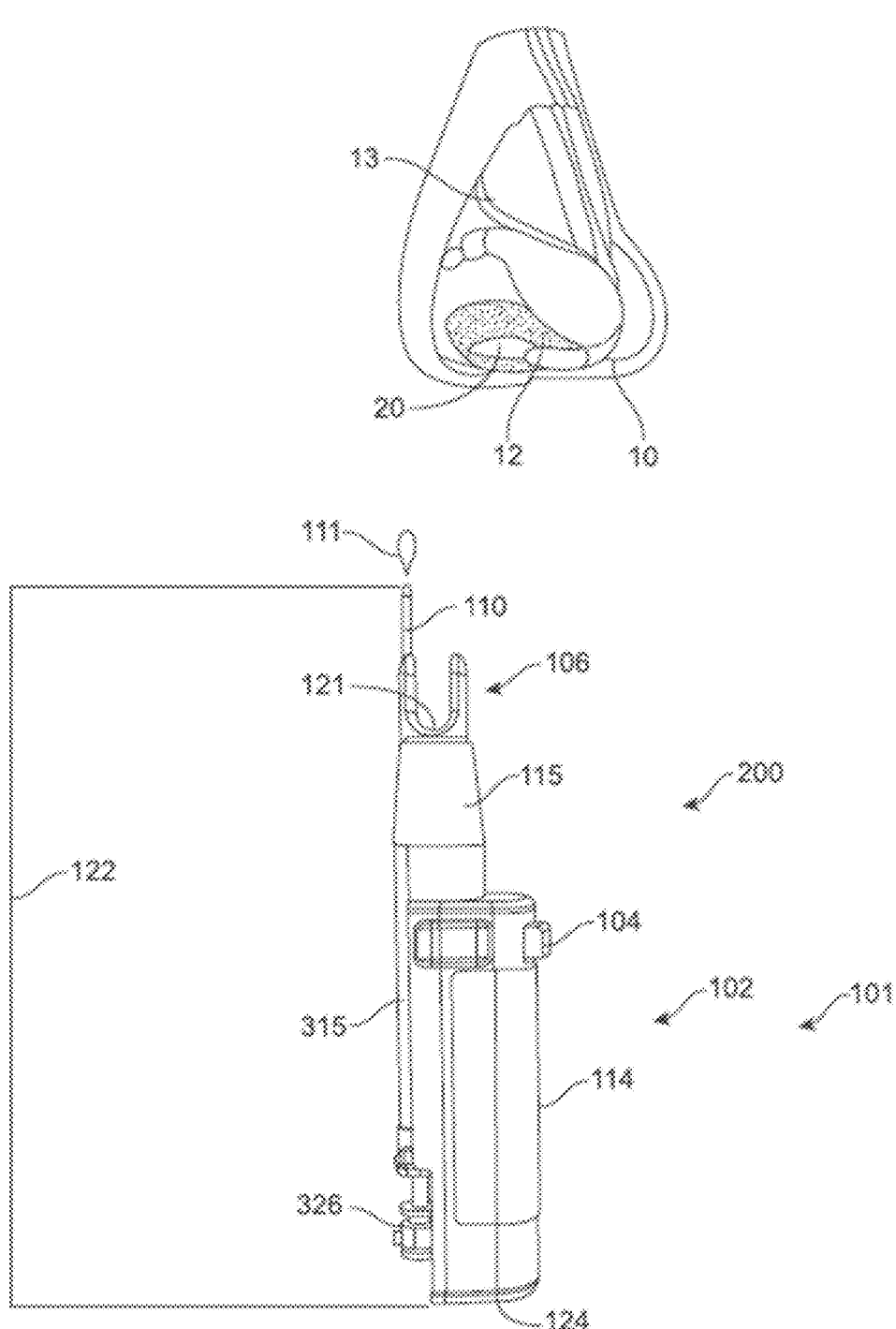
FIG. 4A depicts an exemplary embodiment of an Exemplary Device in the second configuration with one dispensing element revealed and a side view of an exemplary embodiment of a subject's nose, according to some embodiments.
Figure 4B:
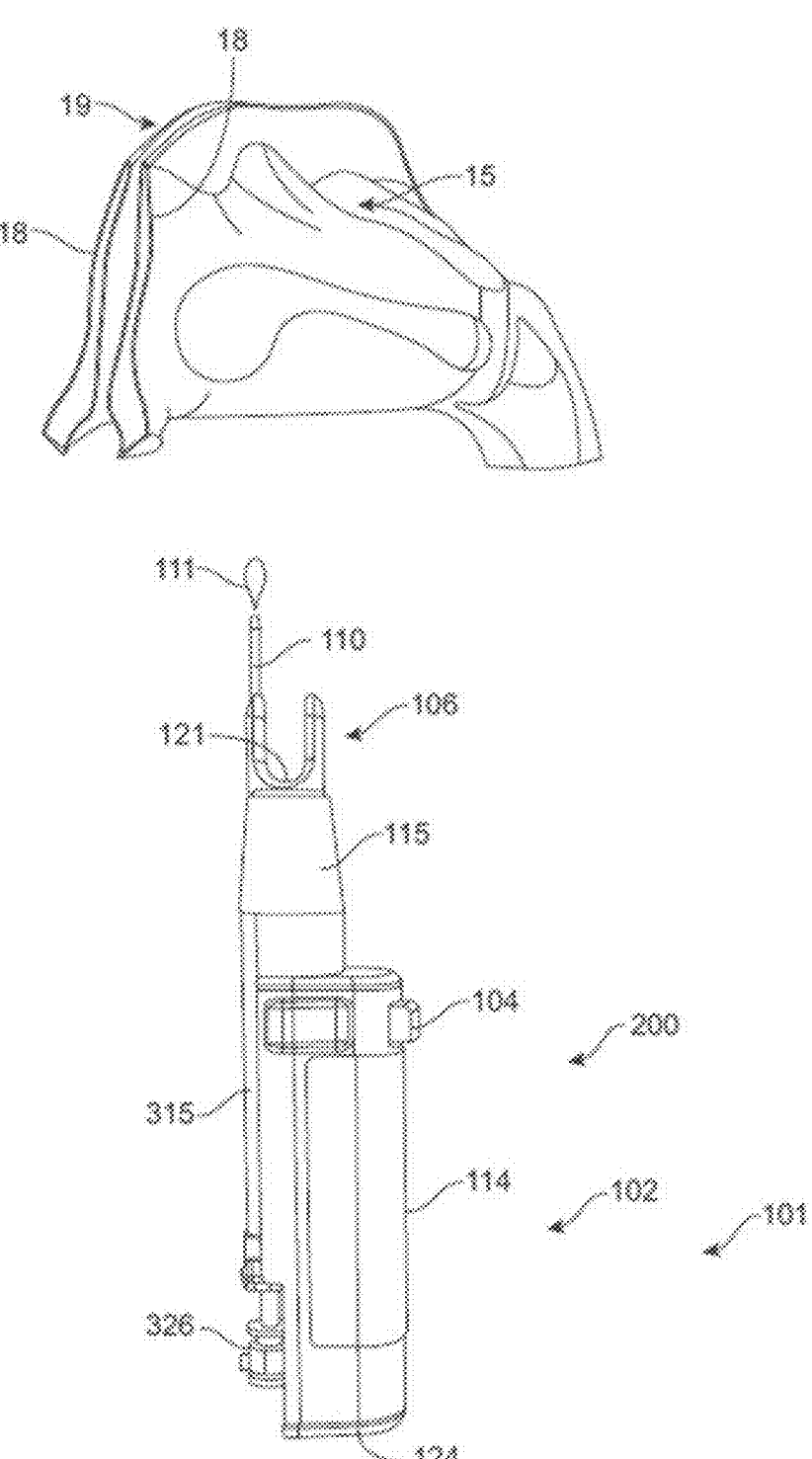
FIG. 4B depicts an exemplary embodiment of an Exemplary Device in the second configuration with one dispensing element revealing along the passageway and a side view of an exemplary embodiment of a representation subject's nasal channels from the vestibule to the olfactory cleft based on an anteriorly oriented plane, according to some embodiments

In some embodiments, the device comprises at least one dispensing element 110. In some embodiments, the device comprises at least one insertable portion 107. In some embodiments the at least one dispensing element 110 extends from or is revealed by the at least one insertable portion 107. In some embodiments, at least one insertable portion 107 comprises the at least one dispensing element 110. In some embodiments, a cannula is within an insertable portion 107, or the at least one dispensing element 110 comprises an internal diameter defining a channel. In some embodiments, the cannula is entirely contained within the dispensing element. In some embodiments, an end of the dispensing element is coextensive with the end of the insertable portion. In some embodiments, a dispensing element is entirely contained within the insertable portion when the device is actuated, or when the housing is moved from the first position to the second position (see FIGS. 2G-2J). In some embodiments, an end of the dispensing element is coextensive with an end of the insertable portion when the device is actuated, or when the housing is moved from the first position to the second position (see FIGS. 2G-2J). In some embodiments, the dispensing element does not extend or reveal from the insertable portion when the device is actuated, or when the housing is moved from the first position to the second position (see FIGS. 2G-2J). In some embodiments, the device may further include a trigger or trigger release 104 coupled to the subject engaging portion 106 on the columella saddle, and may actuate the device when pressure is applied to the trigger release 104 by a subject's columella (see FIGS. 2G-2H). In some embodiments, a dispensing element comprises a cannula.

It is demonstrated herein that the disclosed device can be used for targeted delivery to the middle turbinates, with minimal deposition at the nasal floor and/or nasopharynx. As shown herein, when a liquid is ejected from the ejection zone through a side opening on the dispensing element of the disclosed device, targeted delivery to the middle turbinate can be achieved.

In some embodiments, the dispensing element 110 is configured to dispense a composition 111 from a side opening 2010.

In some embodiments, the composition 111 comprises a liquid composition.

The device can be configured such that at least a percentage of the composition 111 ejected from the side opening 2010 is delivered to the middle turbinate 15.

In some embodiments, at least about 50% of the composition ejected from the side opening is delivered to the middle turbinate. In some embodiments, at least about 55% of the composition ejected from the side opening is delivered to the middle turbinate. In some embodiments, at least about 60% of the composition ejected from the side opening is delivered to the middle turbinate. In some embodiments, at least about 65% of the composition ejected from the side opening is delivered to the middle turbinate. In some embodiments, at least about 70% of the composition ejected from the side opening is delivered to the middle turbinate. In some embodiments, at least about 75% of the composition ejected from the side opening is delivered to the middle turbinate. In some embodiments, at least about 80% of the composition ejected from the side opening is delivered to the middle turbinate. In some embodiments, at least about 85% of the composition ejected from the side opening is delivered to the middle turbinate. In some embodiments, at least about 90% of the composition ejected from the side opening is delivered to the middle turbinate. In some embodiments, at least about 95% of the composition ejected from the side opening is delivered to the middle turbinate. In some embodiments, at least about 98% of the composition ejected from the side opening is delivered to the middle turbinate.

The device can be configured such that at most a percentage of the composition 111 ejected from the side opening 2010 is delivered to the nasopharynx.

In some embodiments, at most about 50% of the composition ejected from the side opening is delivered to the nasopharynx. In some embodiments, at most about 45% of the composition ejected from the side opening is delivered to the nasopharynx. In some embodiments, at most about 40% of the composition ejected from the side opening is delivered to the nasopharynx. In some embodiments, at most about 35% of the composition ejected from the side opening is delivered to the nasopharynx. In some embodiments, at most about 30% of the composition ejected from the side opening is delivered to the nasopharynx. In some embodiments, at most about 25% of the composition ejected from the side opening is delivered to the nasopharynx. In some embodiments, at most about 20% of the composition ejected from the side opening is delivered to the nasopharynx. In some embodiments, at most about 15% of the composition ejected from the side opening is delivered to the nasopharynx. In some embodiments, at most about 10% of the composition ejected from the side opening is delivered to the nasopharynx. In some embodiments, at most about 5% of the composition ejected from the side opening is delivered to the nasopharynx. In some embodiments, at most about 3% of the composition ejected from the side opening is delivered to the nasopharynx. In some embodiments, at most about 1% of the composition ejected from the side opening is delivered to the nasopharynx.

The device can be configured such that the insertable portion 107 is capable of being inserted into a nasal channel 20 of the subject at an insertion angle, the insertion angle being with reference to the subject's coronal plane 608.

In some embodiments, the insertion angle is at least about 25°. In some embodiments, the insertion angle is at least about 26°. In some embodiments, the insertion angle is at least about 27°. In some embodiments, the insertion angle is at least about 28°. In some embodiments, the insertion angle is at least about 29°. In some embodiments, the insertion angle is at least about 30°.

In some embodiments, the insertion angle is at most about 45°. In some embodiments, the insertion angle is at most about 44°. In some embodiments, the insertion angle is at most about 43°. In some embodiments, the insertion angle is at most about 42°. In some embodiments, the insertion angle is at most about 41°. In some embodiments, the insertion angle is at most about 40°.

In some embodiments, the insertion angle is between about 25° and about 45°. In some embodiments, the insertion angle is between about 30° and about 40°.

The dispensing element 110 can be configured such that, when said dispensing element 110 is revealed from the insertable portion 107 within the ejection zone 29, the side opening 2010 can dispense the composition 111 towards the nasal cavity away from the internal nasal dorsum.

The dispensing element can be configured such that, when said dispensing element 110 is revealed from the insertable portion 107 within the ejection zone 29, the side opening 2010 can comprise an offset angle, which is an angle about a posterior-anterior plane of the subject. For example, when the offset angle is 0°, the direction the side opening faces is parallel to the sagittal plane 603 of the subject. In some embodiments, the offset angle is less than about 25°. In some embodiments, the offset angle is less than about 20°. In some embodiments, the offset angle is less than about 15°. In some embodiments, the offset angle is less than about 10°. In some embodiments, the offset angle is less than about 5°. In some embodiments, the offset angle is about 0°.

Referring to FIGS. 24A-24D. Various shapes of the side opening are contemplated. For example, the side opening 2010 can have a generally quadrilateral shape. The side opening 2010 can be a substantially rectangular shape. The shape can have one or more rounded corners. The side opening 2010 can comprise one or more boundaries that are not defined by a straight line.

The side opening 2010 can have a generally elongate shape, comprising a length 2020 between a distal end and a proximal end that generally aligns with a longitudinal axis of the dispensing element 110.

In some embodiments, the length 2020 of the side opening 2010 is at least about 10%, at least about 10%, at least about 20%, at least about 30%, at least about 40%, at least about 50%, at least about 60%, at least about 70%, at least about 80%, at least about 90%, or at least about 95% of the length of the dispensing element 110 revealed from the insertable portion 107 upon actuation.

In some embodiments, the length 2020 of the side opening 2010 is at most about 99%, at most about 95%, at most about 90%, at most about 80%, at most about 70%, at most about 60%, at most about 50%, at most about 40%, at most about 30%, at most about 20%, or at most about 10% of the length of the dispensing element 110 revealed from the insertable portion 107 upon actuation.

The length 2020 of the side opening 2010 can be substantially the length of the dispensing element 110 revealed from the insertable portion 107 upon actuation. The length 2020 of the side opening 2010 can be shorter than the length of the dispensing element 110 revealed from the insertable portion 107 upon actuation.

In some embodiments, the side opening comprises a length from about 1 mm to about 40 mm, from about 1 mm to about 35 mm, from about 1 mm to about 30 mm, from about 1 mm to about 25 mm, from about 1 mm to about 20 mm, from about 1 mm to about 15 mm, from about 1 mm to about 13 mm, from about 1 mm to about 11 mm, from about 1 mm to about 9 mm, from about 1 mm to about 7 mm, from about 1 mm to about 5 mm, or from about 1 mm to about 3 mm. In some embodiments, the side opening comprises a length from about 2 mm to about 40 mm, from about 2 mm to about 35 mm, from about 2 mm to about 30 mm, from about 2 mm to about 25 mm, from about 2 mm to about 20 mm, from about 2 mm to about 15 mm, from about 2 mm to about 13 mm, from about 2 mm to about 11 mm, from about 2 mm to about 9 mm, from about 2 mm to about 7 mm, from about 2 mm to about 5 mm, or from about 2 mm to about 3 mm. In some embodiments, the side opening comprises a length from about 3 mm to about 40 mm, from about 3 mm to about 35 mm, from about 3 mm to about 30 mm, from about 3 mm to about 25 mm, from about 3 mm to about 20 mm, from about 3 mm to about 15 mm, from about 3 mm to about 13 mm, from about 3 mm to about 11 mm, from about 3 mm to about 9 mm, from about 3 mm to about 7 mm, or from about 3 mm to about 5 mm. In some embodiments, the side opening comprises a length from about 4 mm to about 40 mm, from about 4 mm to about 35 mm, from about 4 mm to about 30 mm, from about 4 mm to about 25 mm, from about 4 mm to about 20 mm, from about 4 mm to about 15 mm, from about 4 mm to about 13 mm, from about 4 mm to about 11 mm, from about 4 mm to about 9 mm, from about 4 mm to about 7 mm, or from about 4 mm to about 5 mm. In some embodiments, the side opening comprises a length from about 5 mm to about 40 mm, from about 5 mm to about 35 mm, from about 5 mm to about 30 mm, from about 5 mm to about 25 mm, from about 5 mm to about 20 mm, from about 5 mm to about 15 mm, from about 5 mm to about 13 mm, from about 5 mm to about 11 mm, from about 5 mm to about 9 mm, or from about 5 mm to about 7 mm. In some embodiments, the side opening comprises a length from about 6 mm to about 40 mm, from about 6 mm to about 35 mm, from about 6 mm to about 30 mm, from about 6 mm to about 25 mm, from about 6 mm to about 20 mm, from about 6 mm to about 15 mm, from about 6 mm to about 13 mm, from about 6 mm to about 11 mm, from about 6 mm to about 9 mm, or from about 6 mm to about 7 mm. In some embodiments, the side opening comprises a length from about 7 mm to about 40 mm, from about 7 mm to about 35 mm, from about 7 mm to about 30 mm, from about 7 mm to about 25 mm, from about 7 mm to about 20 mm, from about 7 mm to about 15 mm, from about 7 mm to about 13 mm, from about 7 mm to about 11 mm, or from about 7 mm to about 9 mm. In some embodiments, the side opening comprises a length from about 8 mm to about 40 mm, from about 8 mm to about 35 mm, from about 8 mm to about 30 mm, from about 8 mm to about 25 mm, from about 8 mm to about 20 mm, from about 8 mm to about 15 mm, from about 8 mm to about 13 mm, from about 8 mm to about 11 mm, or from about 8 mm to about 9 mm. In some embodiments, the side opening comprises a length from about 9 mm to about 40 mm, from about 9 mm to about 35 mm, from about 9 mm to about 30 mm, from about 9 mm to about 25 mm, from about 9 mm to about 20 mm, from about 9 mm to about 15 mm, from about 9 mm to about 13 mm, or from about 9 mm to about 11 mm. In some embodiments, the side opening comprises a length from about 10 mm to about 40 mm, from about 10 mm to about 35 mm, from about 10 mm to about 30 mm, from about 10 mm to about 25 mm, from about 10 mm to about 20 mm, from about 10 mm to about 15 mm, from about 10 mm to about 13 mm, or from about 10 mm to about 11 mm. In some embodiments, the side opening comprises a length from about 11 mm to about 40 mm, from about 11 mm to about 35 mm, from about 11 mm to about 30 mm, from about 11 mm to about 25 mm, from about 11 mm to about 20 mm, from about 11 mm to about 15 mm, or from about 11 mm to about 13 mm. In some embodiments, the side opening comprises a length from about 12 mm to about 40 mm, from about 12 mm to about 35 mm, from about 12 mm to about 30 mm, from about 12 mm to about 25 mm, from about 12 mm to about 20 mm, from about 12 mm to about 15 mm, or from about 12 mm to about 13 mm.

In some embodiments, the side opening comprises a length from about 3 mm to about 12 mm. In some embodiments, the side opening comprises a length from about 6 mm to about 12 mm. In some embodiments, the side opening comprises a length from about 9 mm to about 12 mm.

In some embodiments, the side opening comprises a length of about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, or about 40 mm.

In some embodiments, the side opening comprises a length of about 3 mm. In some embodiments, the side opening comprises a length of about 6 mm. In some embodiments, the side opening comprises a length of about 9 mm. In some embodiments, the side opening comprises a length of about 12 mm.

The side opening 2010 can be defined by a width 2030 at a widest point across the opening, perpendicular to the longitudinal axis of the dispensing element 110. Where the side opening 2010 has a shape defined by two substantially parallel sides, the width 2030 can be measured at any point along the length of the side opening. Where the side opening 2010 has a shape defined by non-parallel sides, for example, a trapezium, the width 2030 of the side opening 2010 can be defined as the width at the widest point across.

In some embodiments, the width 2030 of the side opening 2010 is at least about 10%, at least about 20%, at least about 30%, at least about 40%, at least about 50%, at least about 60%, at least about 70%, at least about 80%, at least about 90%, or at least about 95% of the width of the dispensing element 110.

In some embodiments, the width 2030 of the side opening 2010 is at most about 99%, at most about 95%, at most about 90%, at most about 80%, at most about 70%, at most about 60%, at most about 50%, at most about 40%, at most about 30%, at most about 20%, or at most about 10% of the width of the dispensing element 110.

In some embodiments, the width 2030 of the side opening 2010 is between about 20% and about 99%, between about 30% and about 99%, between about 40% and about 99%, between about 50% and about 99%, between about 60% and about 99%, between about 70% and about 99%, between about 80% and about 99%, or between about 90% and about 99% of the width of the dispensing element.

The width 2030 of the side opening 2010 can be substantially the width of the dispensing element 110. The width 2030 of the side opening 2010 can be smaller than the width of the dispensing element 110.

In some embodiments, the side opening comprises a width of between about 0.1 mm and about 2.0 mm, between about 0.1 mm and about 1.5 mm, between about 0.1 mm and about 1.0 mm, or between about 0.1 mm and about 0.5 mm. In some embodiments, the side opening comprises a width of between about 0.2 mm and about 2.0 mm, between about 0.2 mm and about 1.5 mm, between about 0.2 mm and about 1.0 mm, or between about 0.2 mm and about 0.5 mm. In some embodiments, the side opening comprises a width of between about 0.3 mm and about 2.0 mm, between about 0.3 mm and about 1.5 mm, between about 0.3 mm and about 1.0 mm, or between about 0.3 mm and about 0.5 mm. In some embodiments, the side opening comprises a width of between about 0.4 mm and about 2.0 mm, between about 0.4 mm and about 1.5 mm, or between about 0.4 mm and about 1.0 mm. In some embodiments, the side opening comprises a width of between about 0.5 mm and about 2.0 mm, between about 0.5 mm and about 1.5 mm, or between about 0.5 mm and about 1.0 mm. In some embodiments, the side opening comprises a width of between about 0.6 mm and about 2.0 mm, between about 0.6 mm and about 1.5 mm, or between about 0.6 mm and about 1.0 mm. In some embodiments, the side opening comprises a width of between about 0.7 mm and about 2.0 mm, between about 0.7 mm and about 1.5 mm, or between about 0.7 mm and about 1.0 mm. In some embodiments, the side opening comprises a width of between about 0.8 mm and about 2.0 mm, between about 0.8 mm and about 1.5 mm, or between about 0.8 mm and about 1.0 mm. In some embodiments, the side opening comprises a width of between about 0.9 mm and about 2.0 mm, between about 0.9 mm and about 1.5 mm, or between about 0.9 mm and about 1.0 mm. In some embodiments, the side opening comprises a width of between about 1.0 mm and about 2.0 mm, or between about 1.0 mm and about 1.5 mm. In some embodiments, the side opening comprises a width of between about 1.1 mm and about 2.0 mm, or between about 1.1 mm and about 1.5 mm. In some embodiments, the side opening comprises a width of between about 1.2 mm and about 2.0 mm, or between about 1.2 mm and about 1.5 mm.

In some embodiments, the side opening comprises a width of between about 0.2 mm and about 1.5 mm. In some embodiments, the side opening comprises a width of between about 0.3 mm and about 1.4 mm.

In some embodiments, the side opening comprises a width of about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, or about 2.0 mm.

In some embodiments, the side opening comprises a width of about 0.3 mm. In some embodiments, the side opening comprises a width of about 0.5 mm. In some embodiments, the side opening comprises a width of about 0.7 mm. In some embodiments, the side opening comprises a width of about 0.9 mm. In some embodiments, the side opening comprises a width of about 1.1 mm. In some embodiments, the side opening comprises a width of about 1.3 mm.

The side opening 2010 can be defined by an area of the opening.

In some embodiments, the side opening comprises an opening area of between about 0.2 $mm^2$ and about 50 $mm^2$, between about 0.3 $mm^2$ and about 40 $mm^2$, between about 0.4 $mm^2$ and about 30 $mm^2$, between about 0.5 $mm^2$ and about 25 $mm^2$, between about 1.0 $mm^2$ and about 20 $mm^2$, between about 2.0 $mm^2$ and about 20 $mm^2$, between about 3.0 $mm^2$ and about 20 $mm^2$, between about 4.0 $mm^2$ and about 20 $mm^2$, between about 5.0 $mm^2$ and about 20 $mm^2$, between about 6.0 $mm^2$ and about 20 $mm^2$, between about 7.0 $mm^2$ and about 20 $mm^2$, between about 8.0 $mm^2$ and about 20 $mm^2$, between about 9.0 $mm^2$ and about 20 $mm^2$, or between about 10 $mm^2$ and about 20 $mm^2$.

In some embodiments, the side opening comprises an opening area of between about 0.5 $mm^2$ and about 25 $mm^2$. In some embodiments, the side opening comprises an opening area of between about 1.0 $mm^2$ and about 20 $mm^2$. In some embodiments, the side opening comprises an opening area of between about 5.0 $mm^2$ and about 20 $mm^2$. In some embodiments, the side opening comprises an opening area of between about 10 $mm^2$ and about 20 $mm^2$.

It is demonstrated herein that the device can be configured so that a liquid having a viscosity can be ejected from the side opening at a velocity and/or volumetric flow rate and achieve targeted deposition at the middle turbinate with minimal off-target deposition.

In some embodiments, the device is configured to eject a liquid composition having a viscosity from the side opening.

In some embodiments, the liquid has a viscosity of between about 0.5 cP and about 50 cP. In some embodiments, the liquid has a viscosity of between about 0.5 cP and about 40 cP. In some embodiments, the liquid has a viscosity of between about 0.5 cP and about 30 cP. In some embodiments, the liquid has a viscosity of between about 0.5 cP and about 20 cP. In some embodiments, the liquid has a viscosity of between about 0.5 cP and about 10 cP. In some embodiments, the liquid has a viscosity of between about 0.5 cP and about 5 cP. In some embodiments, the liquid has a viscosity of between about 5 cP and about 10 cP. In some embodiments, the liquid has a viscosity of between about 10 cP and about 15 cP. In some embodiments, the liquid has a viscosity of between about 15 cP and about 20 cP. In some embodiments, the liquid has a viscosity of between about 20 cP and about 25 cP. In some embodiments, the liquid has a viscosity of between about 25 cP and about 30 cP. In some embodiments, the liquid has a viscosity of between about 30 cP and about 35 cP. In some embodiments, the liquid has a viscosity of between about 35 cP and about 40 cP. In some embodiments, the liquid has a viscosity of between about 40 cP and about 45 cP. In some embodiments, the liquid has a viscosity of between about 45 cP and about 50 cP. In some embodiments, the liquid has a viscosity of about 1 cP. In some embodiments, the liquid has a viscosity of about 20 cP.

In some embodiments, the device is configured to eject the composition from the side opening at a velocity.

In some embodiments, the velocity is between about 2 m/s and about 10 m/s. In some embodiments, the velocity is between about 2 m/s and about 9 m/s. In some embodiments, the velocity is between about 2 m/s and about 8 m/s. In some embodiments, t the velocity is between about 2 m/s and about 7 m/s. In some embodiments, the velocity is between about 2 m/s and about 6 m/s. In some embodiments, the velocity is between about 2 m/s and about 5 m/s. In some embodiments, the velocity is between about 2 m/s and about 4 m/s. In some embodiments, the velocity is between about 3 m/s and about 10 m/s. In some embodiments, the velocity is between about 3 m/s and about 9 m/s. In some embodiments, the velocity is between about 3 m/s and about 8 m/s. In some embodiments, the velocity is between about 3 m/s and about 7 m/s. In some embodiments, the velocity is between about 3 m/s and about 6 m/s. In some embodiments, the velocity is between about 3 m/s and about 5 m/s. In some embodiments, the velocity is between about 4 m/s and about 10 m/s. In some embodiments, the velocity is between about 4 m/s and about 9 m/s. In some embodiments, the velocity is between about 4 m/s and about 8 m/s. In some embodiments, the velocity is between about 4 m/s and about 7 m/s. In some embodiments, the velocity is between about 4 m/s and about 6 m/s. In some embodiments, the velocity is between about 5 m/s and about 10 m/s. In some embodiments, the velocity is between about 5 m/s and about 9 m/s. In some embodiments, the velocity is between about 5 m/s and about 8 m/s. In some embodiments, the velocity is between about 5 m/s and about 7 m/s. In some embodiments, the velocity is between about 6 m/s and about 10 m/s. In some embodiments, the velocity is between about 6 m/s and about 9 m/s. In some embodiments, the velocity is between about 6 m/s and about 8 m/s. In some embodiments, the velocity is between about 7 m/s and about 10 m/s. In some embodiments, the velocity is between about 7 m/s and about 9 m/s. In some embodiments, the velocity is between about 8 m/s and about 10 m/s.

In some embodiments, the device is configured to eject the composition from the side opening at a volumetric flow rate, defined as Q=V*A, where Vis velocity; A is cross-sectional area of the lumen.

In some embodiments, the volumetric flow rate is between about 1.5 ml/s and about 20 ml/s. In some embodiments, the volumetric flow rate is between about 1.5 ml/s and about 15 ml/s. In some embodiments, the volumetric flow rate is between about 1.5 ml/s and about 10 ml/s. In some embodiments, the volumetric flow rate is between about 2 ml/s and about 20 ml/s. In some embodiments, the volumetric flow rate is between about 2 ml/s and about 15 ml/s. In some embodiments, the volumetric flow rate is between about 2 ml/s and about 10 ml/s. In some embodiments, the volumetric flow rate is between about 3 ml/s and about 20 ml/s. In some embodiments, the volumetric flow rate is between about 3 ml/s and about 15 ml/s. In some embodiments, the volumetric flow rate is between about 3 ml/s and about 10 ml/s. In some embodiments, the volumetric flow rate is between about 4 ml/s and about 20 ml/s. In some embodiments, the volumetric flow rate is between about 4 ml/s and about 15 ml/s. In some embodiments, the volumetric flow rate is between about 4 ml/s and about 10 ml/s. In some embodiments, the volumetric flow rate is between about 5 ml/s and about 20 ml/s. In some embodiments, the volumetric flow rate is between about 5 ml/s and about 15 ml/s. In some embodiments, the volumetric flow rate is between about 5 ml/s and about 10 ml/s.

In some embodiments, the at least one channel 125 within an insertable portion 107, or the at least one dispensing element 110 has an inner diameter 129 of 0.3 to 3.0 mm. In some embodiments, the at least one dispensing channel 125 within an insertable portion 107, or the at least one dispensing element 110 has an inner diameter 129 of 0.3 to 0.7 mm. In some embodiments, the at least one dispensing channel 125 within an insertable portion 107, or the at least one dispensing element 110 has an inner diameter 129 of 0.5 to 1.0 mm. In some embodiments, the at least one dispensing element 110, e.g., cannula, may be adapted to deliver the composition 111 having a low, intermediate, or high viscosity along the passageway to the subject's middle meatus 30 or other areas of nasal anatomy. In some embodiments, the at least one dispensing element 110, e.g., cannula, may be adapted to deliver the composition 111 having a moderate (e.g., greater than 1 cP) or high viscosity (e.g., greater than or equal to 50 cP) to the passageway to the subject's middle meatus 30 or other areas of nasal anatomy.

In some embodiments the first portion 102 comprises a semi-ellipse outer shell 114. In some embodiments, the semi-ellipse outer shell 114 comprises the outermost portion of the first portion 102. In some embodiments, the first portion 102 comprises an at least one tiered semi-conical outer shell 115 located horizontally adjacent to the semi-ellipse outer shell 114. In some embodiments, the at least one tiered semi-conical outer shell 115 comprises two tiers of semi-conical outer shell, wherein each tier of semi-conical outer shell is vertically adjacent to the other tier or tiers of semi-conical outer shell. In some embodiments, the at least one tiered semi-conical outer shell 115 comprises a top tier of semi-conical outer shell which partially encloses a bottom tier of semi-conical outer shell. In some embodiments, the first portion 102 comprises a trigger release 104. In some embodiments, the first portion 102 comprises a rectangular cut-out opening, wherein the rectangular cut-out opening has approximately the same length and width dimensions as the trigger release 104. In some embodiments, the trigger release 104 is inserted into the housing 101 through the rectangular cut-out opening, wherein the rectangular cut-out opening has approximately a same length and width dimensions as the trigger release 104. In some embodiments, the housing comprises a second portion 103. In some embodiments, the second portion 103 comprises a chassis 116. In some embodiments, the chassis 116 comprises a chassis rectangular region 117, a chassis semi-conical region 118, and a chassis finial region 119. In some embodiments, the chassis rectangular region 117 comprises an oval shaped hole 132 revealing vertically along a horizontal center of the rectangular region 117. In some embodiments, the semi-conical region 118 is vertically adjacent to the rectangular region 117. In some embodiments, the rectangular region 117 reveals along the length of the semi-conical region 118 such that two adjacent rectangular regions are formed 120. In some embodiments, the finial region 119 is located vertically adjacent to the semi-conical region 118. In some embodiments, the finial region 119 comprises a horizontal width shorter than a horizontal width of the semi-conical region 118. In some embodiments, the chassis 116 comprises a shape for insertion into the first portion 102. In some embodiments, the chassis rectangular region 117 aligns with the at least one tiered semi-conical outer shell 115, wherein such alignment creates a bottom 124 of the housing 101. In some embodiments, the chassis finial region 119 aligns with the at least one tiered semi-conical outer shell 115, wherein such alignment creates an outer shell of the insertable portion 107 of the housing 101.

In some embodiments, the device is transitionable from a first configuration 100 to a second configuration 200. In some embodiments, the subject engaging portion 106 is engaged with the user's columella region 10 when inserting the device into the subject's nasal channel 20, where the subject engaging portion 106 recesses the columella saddle 121 into the first portion 102 of the housing 101 or the at least one tiered semi-conical outer shell 115. In some embodiments, the at least one dispensing element 110 reveals from the at least one insertable portion 107 upon transition of the device from the first configuration 100 to the second configuration 200. In some embodiments, the vertical length in the second configuration 122 is longer than the vertical length in the first configuration 123. In some embodiments, when the device is transitionable from the first configuration 100 to the second configuration 200, the housing 101 defines the first insertable portion 107, and the device further comprises the dispensing element 110 coupled to the housing 101, the dispensing element 110 revealing from the first insertable portion 107 upon transition of the device from the first configuration 100 to the second configuration 200. In some embodiments, the device comprises a bottom 124 wherein the first portion 102 and the second portion 103 interface or connect.

In some embodiments, upon insertion of one or both insertable portions 107 into one or both nasal channels 20 of the subject, the one or both insertable portions 107 engage tissue within the nasal channel 20 to open or expand one or both internal nasal valves 13, thereby positioning the one or both insertable portions 107 for delivery of a composition 111 to the subject, either simultaneously or sequentially, from one or more dispensing ports 126. In some embodiments, the device may further include a trigger or trigger release 104 coupled to the housing 101 and the subject engaging portion 106, which actuates one or both insertable portions 107, either simultaneously or sequentially, to deliver a composition 111 to one or both nasal channels 20 of the subject upon application of pressure by the subject engaging portion to the columella region 10.

In some embodiments, the insertable portion 107 may limit contamination of biome from different sub-regions of a nasal channel 20 and/or stabilize the dispensing element 110. The insertable portion 107 may allow for a shorter dispensing element 110 which is more stable and less prone to bending and deflection.

The device may comprise insertable portions 107 designed to fit snuggly with the anterior tight angle of the internal nasal valve 13 where the septum 24 meets the upper lateral cartilage 25. The device may comprise insertable portions 107 comprising a shape 130, wherein the shape comprises a wing, a foil, a wedge, an oval or oblong, or even a round form. The device may comprise one insertable portion 107, wherein the insertable portion 107 comprises one or more channels 125 leading to one or more dispensing ports 126.

Referring to FIGS. 3A-3D. In some embodiments, the device comprises an adjustable or re-configurable spring 301. In some embodiments, the device comprises a lay shaft 302. In some embodiments, the device comprises a spring core guide 306. In some embodiments, the device comprises a columella slider 307. In some embodiments, the device comprises a columella saddle 121. In some embodiments, the device comprises a guide dowel 309. In some embodiments, the device comprises a spring support 310. In some embodiments, the device comprises a travel limit 311. In some embodiments, the device comprises a trigger release 104. In some embodiments, the device comprises a turcite damper 312. In some embodiments, the device comprises a bushing support 314. In some embodiments, the device comprises a turcite preload ring 313. In some embodiments, the device comprises a syringe 315 comprising a therapeutic composition. In some embodiments, the syringe 315 comprises a syringe volume. In some embodiments the syringe volume is between 1 cc and 5 cc. In some embodiments the syringe volume is at most 10 cc. In some embodiments the syringe volume is at least 1 cc. In some embodiments the syringe volume is at least 1 cc, 2 cc, 3 cc, 4 cc, 5 cc, 6 cc, 7 cc, 8 cc, 9 cc or 10 cc. In some embodiments the syringe volume is up to 1 cc, 2 cc, 3 cc, 4 cc, 5 cc, 6 cc, 7 cc, 8 cc, 9 cc or 10 cc In some embodiments, the columella saddle 121 comprises a "U-shaped" saddle perpendicular to a columella slider insert 320. In some embodiments, the columella slider insert 320 comprises a columella saddle recessed region 321 and columella saddle semi-conical region 322. In some embodiments, the columella slider insert 320 is designed for insertion into a columella slider 307. In some embodiments, the columella slider 307 is designed for insertion into the columella slider insert 320. In some embodiments, the columella slider 307 comprises a cylinder comprising a cut-out columella slider semi-conical region 323, wherein the cut-out columella slider semi-conical region 323 comprises a larger radius than a radius of the columella saddle semi-conical region 322. In some embodiments, the columella slider 307 comprises a recessed cut-out region, wherein the recessed rectangular cut-out is about the same dimensions as the columella saddle recessed region 321. In some embodiments, the syringe 315 comprises the dispensing element 110, a syringe cylindrical barrel 324, a syringe funnel region 325, a syringe arm region 333 and a syringe actuation region 327. In some embodiments, the syringe actuation region 327 comprises two circular stoppers, wherein at least one circular stopper is configured for applying pressure to the syringe cylindrical barrel 324. In some embodiments, the syringe actuation region 327 comprises two circular stoppers, wherein at least one circular stopper is configured for stopping the movement of the syringe 315. In some embodiments, the syringe 315 is inserted into the cut-out columella slider semi-conical region 323 and into columella saddle semi-conical region 322. In some embodiments, a syringe push arm 326 comprises a circular cut-out for insertion of the syringe actuation region 327 region. In some embodiments the first portion 102 comprises a first portion backside 328, wherein the chassis 116 is inserted. In some embodiments, the backside 328 comprises a semi-cylindrical cut-out region for insertion of the syringe cylindrical barrel 324. In some embodiments, the first portion backside 328 comprises a first portion backside cut-out recessed rectangular region 330. In some embodiments, the cut-out recessed rectangular region 330 comprises a storage region, wherein the syringe actuation region 327 region and the syringe push arm 326 regions are stored. In some embodiments, the first portion backside 328 comprises a first portion backside rectangular region 331 and a first portion backside recessed rectangular region 332. In some embodiments, the first portion backside rectangular region 331 comprises a rectangular region to recessed rectangular region interface with at least one arm stopper 334. In some embodiments, the at least one arm stopper 334 is flush with a syringe arm 333. In some embodiments, the rectangular region 331 comprises two first portion backside recessed cut-out rectangular regions 335. In some embodiments, the chassis 116 comprises two chassis rectangular regions 345, wherein the two recessed cut-out rectangular regions 335 are inserted into the two rectangular regions 345. In some embodiments, the syringe push arm 326 comprises at least one syringe push arm cylindrical cutout region 336 for insertion of the lay shaft 302. In some embodiments, the lay shaft 302 comprises at least one screw hole extending across the horizontal length of the lay shaft 302, wherein the screw hole is located at a lay shaft second end 338 of the lay shaft 302. In some embodiments, the second end 338 is connected to at least one cylindrical cutout region 336 via a screw. In some embodiments, the lay shaft 302 extends from the bottom of the device 124 to the trigger release 104. In some embodiments, turcite preload ring 313 has a greater circumference than the turcite bushing 312. In some embodiments, turcite preload ring 313 is wrapped around the lay shaft 302 such that turcite preload ring 313 extends along a portion of the vertical length of the lay shaft 302. In some embodiments, turcite preload ring 313 comprises an inner surface such that the inner surface of turcite preload ring 313 contacts an outer surface of the lay shaft 302. In some embodiments, turcite bushing 312 is wrapped around turcite preload ring 313 such that turcite bushing 312 extends along approximately the same portion of the vertical length of the lay shaft 302 as turcite preload ring 313. In some embodiments, a spring support 310 is located along the vertical length of the shaft 302. In some embodiments, the lay shaft 302 comprises at least one screw hole, wherein at least one screw is inserted to affix the spring support 310 to the lay shaft 302. In some embodiments, the lay shaft 302 comprises at least one screw hole extending across the horizontal length of the lay shaft 302, wherein the screw hole is located at a lay shaft first end 337 of the lay shaft 302. In some embodiments, the first end 337 is connected to the trigger release 104 via a screw. In some embodiments, the trigger release 104 comprises a pin hole for insertion of a stainless steel dowel pin 339. In some embodiments, the spring 301 extends vertically along 302. In some embodiments, the spring 301 has a spring first end 340 and a spring second end 341. In some embodiments, the first end 340 is wrapped around the circumference of turcite bushing 312. In some embodiments, the second end 341 is wrapped around stainless steel dowel pin 339. In some embodiments, columella slider 307 comprises a guide dowel hole 342. In some embodiments, the guide dowel 309 comprises a guide dowel first end 343 and a guide dowel second end 344. In some embodiments, guide dowel first end 343 contacts the columella saddle recessed region 321. In some embodiments, the guide dowel extends along a vertical length of the device such that the guide dowel sec end 344 is located parallel to the spring 301. In some embodiments, the trigger release 104 has a recessed semi-cylindrical region, wherein actuation of the trigger release 104 presses the trigger release 104 against the guide dowel 309. In some embodiments, the device is actuated by application of force onto the trigger release 104 by the user. In some embodiments, the device is actuated by the user's application of force onto the trigger release 104 following unlocking of the trigger by application of pressure to the subject engaging portion 106 with the user's columella region 10. In some embodiments, the user may use any digit to actuate the device.

In some embodiments, the subject engaging portion 106 positions the insertable portions 107 and/or the dispensing elements 110 within the nasal channel 20 of the subject and limits the depth of insertion of the insertable portions 107 and/or the dispensing elements 110 into the nasal channel 20. In some embodiments, upon insertion of the first insertable portion 107 into a nasal channel 20 of the subject, the first insertable portion 107 opens or expands the internal nasal valve 13 by pushing the upper lateral cartilage 25 and surrounding tissue up and away 625 from the septum 24 of the subject thereby positioning at least one of the insertable portions 107 for delivery of the composition 111 to the subject. In some embodiments, the internal nasal valve 13 is located approximately 1.3 cm from the entrance to the nasal vestibule 21. In some embodiments, the internal nasal valve 13 comprises a narrowest portion of the nasal channel 20. The internal nasal valve 13 comprises an average angle in a Caucasian ranging from 9° to 15°. In some embodiments, the device is actuated by the user's application of force onto the trigger release 104. In some embodiments, the user may use any digit to actuate the device.

In some embodiments, the columella saddle 121 positions the first insertable portion 107 and the second insertable portion 107 as to align the at least one insertable portion 107 and/or dispensing element 110 with the middle meatus 30 when the device is actuated. In some embodiments, the columella saddle 121 positions the first insertable portion 107 and the second insertable portion 107 as to align the at least one insertable portion 107 and/or dispensing element 110 along the passageway to the middle meatus 30 when the device is actuated. In some embodiments, the columella saddle 121 comprises a shape 130 which matches an anatomy of the subject's columella 10 and aligns the one or more insertable portion 107 and/or dispensing element 110 with the subject's middle meatus 30. In some embodiments, the device comprises the insertable portion 107 and/or dispensing element 110 positioned proximal to the middle meatus 30 of the subject when the columella saddle 121 is engaging the columella 10 of the subject.

In some embodiments, the first and/or second insertable portion 107 opens or expands the internal nasal valve 13 by pushing the upper lateral cartilage 25 and surrounding tissue up and away 625 from the septum 24 and clearing a pathway for dispensing of the compound 111. In some embodiments, the pressure is applied to the subject engaging portion 106 by the columella region 10. In some embodiments, the at least one insertable portion 107 and/or dispensing element 110 reveals from the insertable portions 107 toward the target region, e.g., to the middle meatus 30, or other nasal anatomy, based on a second plane 18 to dispense the composition 111.

The device may comprise two insertable portions 107, wherein one insertable portion 107, has one or more channels 125 leading to one or more dispensing ports 126. The device may comprise two insertable portions 107, wherein both insertable portions 107 have one or more channels 125 leading to one or more dispensing ports 126. The device may comprise two insertable portions 107, wherein both insertable portions 107 have one or more channels 125 leading to one or more dispensing ports 126, wherein a composition 111 can be delivered at the same time or sequentially from each insertable portion 107 or the dispensing element 110. The device may comprise two insertable portions 107, wherein one insertable portion 107 includes one or more dispensing elements 110 that are fixed relative to the insertable portion 107 leading to one or more dispensing ports 126. The device may comprise two insertable portions 107, wherein both insertable portions 107 include one or more dispensing elements 110 that are fixed relative to the insertable portions 107 leading to one or more dispensing ports 126. The device may comprise two insertable portions 107, wherein both insertable portions 107 include one or more dispensing elements 110 that are fixed relative to the insertable portions 107 leading to one or more dispensing ports 126, wherein a compound 111 can be delivered at the same time or sequentially from each insertable portion 107 or the dispensing element 110. The device may comprise two insertable portions, 107 wherein one insertable portion 107 includes one or more dispensing elements 110 that are moveable relative to the insertable portion 107 with one or more dispensing ports 126. The device may comprise two insertable portions 107, wherein both insertable portions 107 include one or more dispensing elements 110 that are moveable relative to the insertable portion 107 with one or more dispensing ports 126. The device may comprise two insertable portions 107, wherein both insertable portions 107 include one or more dispensing elements that are moveable relative to the insertable portion 107 with one or more dispensing ports 126, wherein a composition 111 can be delivered at the same time or sequentially from each insertable portion 107 or the dispensing element 110. The device may further comprise two insertable portions 107, wherein the composition 111 can be delivered to a turbinate or other target regions of the nasal cavity.

In some embodiments, the one or more dispensing elements 110 are contained within a secondary tubular member. In some embodiments, the trigger release 104 comprises a button, wherein the button is pushed to actuate the device. In some embodiments, the device cannot be actuated until the device is in the second configuration 200. In some embodiments, the device cannot be actuated until the device is not in the first configuration 100. In some embodiments, the device is in the first configuration 100, wherein the trigger release 104 cannot actuate the device. In some embodiments, the device is in the second configuration 200, wherein the trigger release 104 can actuate the device. In some embodiments, the trigger release 104 can be thumb actuated. In some embodiments, the trigger release 104 can be actuated by index and middle fingers.

Figure 5:
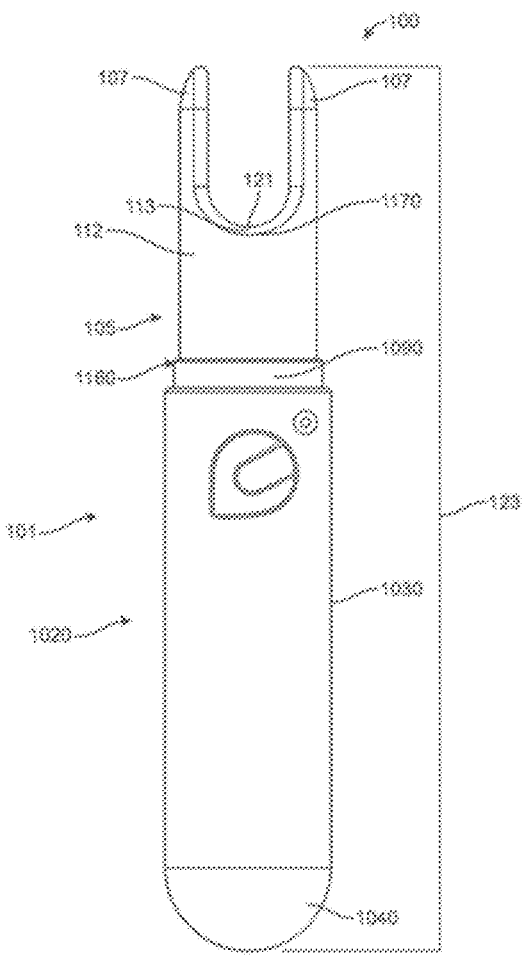
FIG. 5 depicts an exemplary embodiment of an Exemplary Device in a first configuration, according to some embodiments.

FIG. 5 depicts an exemplary embodiment of an exemplary device in a first configuration. In some embodiments, the housing 101 comprises a first portion 1020 which defines a cylindrical portion 1030 and a rounded bottom 1040. In some embodiments, the housing 101 comprises a second portion 105 which is located vertically adjacent to the first portion 1020, wherein the first portion 1020 may have a larger diameter than the second portion 105 to accommodate insertion of the second portion 105 into the first portion 1020. In some embodiments, the second portion 105 comprises the subject engaging portion 106, wherein the subject engaging portion 106 comprises a "U" or "saddle" shaped element 121. In some embodiments, the subject engaging portion 106 engages the columella region of a subject 10. In some embodiments, the second portion 105 comprises at least one insertable portion 107. In some embodiments, the second portion 105 comprises two insertable portions 107, each for insertion into a nasal channel 20 of the subject.

In some embodiments, the second portion 105 of the housing 101 comprises the subject engaging portion 106. In some embodiments, the subject engaging portion 106 comprises a recessed top portion. In some embodiments, the recessed top portion comprises the "U" or "saddle" shape element 121. In some embodiments, the "U" or "saddle" shape element 121 comprises the center of the recessed top portion. In some embodiments, the cylindrical middle portion 112 is located vertically adjacent to the "U" or "saddle" shape element 121 such that the center of the recessed top portion 106 is coplanar with a top surface of the cylindrical middle portion 112 such that they form a unilateral plane 1170. In some embodiments, the device comprises the first configuration 100 wherein the first fiducial marker 1080 is completely visible. In some embodiments, the device in the first configuration 100 comprises a vertical length in the first configuration 123. In some embodiments, the device comprises a second cylindrical fiducial marker 1090, wherein the second cylindrical fiducial marker is partially revealed from the cylindrical portion 1030 of the first portion 1020 of the housing 101. In some embodiments, the cylindrical middle portion 112 has a bottom surface substantially coplanar with a top surface of the second fiducial marker 1090 such that they form a unilateral plane 1160.

In some embodiments, the columella trigger release 104 design is configured to enable triggering only upon proper insertion and limit movement upon triggering.

In some embodiments, the columella saddle 121 comprises an anchor or depth datum 617 from which to establish insertion depth as a free-standing attribute.

In some embodiments, the columella trigger release 104 comprises a hand grip for the hand to simply grip the device without concerning any digit with the task of actuating. In some embodiments, the device comprises a grasping configuration, wherein the subject can grasp the device with the intent (i.e., grasp intention) of lifting the device to their face and not have to readjust grasp to actuate. In some embodiments, the device comprises the columella trigger release 104, wherein the columella trigger release 104 facilitates low/no cognition actuation as no judgement is required for when to actuate so the subject can focus singularly on insertion.

In some embodiments, the insertable portions 107 comprise an insertion angle configured to open the passageway between the septum 24 and nasal valve 13 and reduce cannula insertion depth appearance. In some embodiments, the columella saddle 121 reduces the insertion angle concern. In some embodiments, full insertions require proper insertion angles. In some embodiments, the width 1103 of the insertable portions 107 fills the lower aspect of the nasal channel 20, pushing hair aside minimizing the chance of a sneeze reflex as compared to the smaller diameter catheter being pushed up through the insertable portion 107. In some embodiments, the insertable portion 107 is comparable to an "ear", optionally a flat "ear". In some embodiments, the device comprises two flat ears, wherein the two flat ears help each other hug the septum 24 side of each nasal channel 20, minimizing the potential for fetching up on the nasal valve 13. In some embodiments, the device comprises at least one flat insertable portion 107, wherein the at least one flat insertable portion 107 makes it uncomfortable or awkward to twist sideways so proper insertion is not negatively impacted while the subject is holding the device when it is partially or fully inserted. In some embodiments, the device comprises the 'wedge' shape 130 at the leading edge, wherein the 'wedge' shape 130 pushes the compressible and malleable cartilage of the nasal valve 13 up and away 625 from the septum 24, giving the side opening 2010 a more direct line-of-sight to the middle meatus 30 or back of the turbinates of the nasal channel 20. In some embodiments, the device comprises the flat shape of the insertable portion 107, wherein the flat shape of the insertable portion 107 provides preferential bending to accommodate irregular surfaces along the septum 24. In some embodiments, the device comprises the flat shape of the insertable portion 107, 'wherein the flat shape of the insertable portion 107 provides preferential stiffness to minimize deflection back into the nasal channel 20 should there be irregular intrusions of, for example, the inferior nasal cartilage. In some embodiments, the device comprises the insertable portion 107, wherein the insertable portion 107 are configured to accommodate various degrees of columella flaring. In some embodiments, the various degrees of columella flaring comprise wider, closer to the face, or further from the tip of nose. In some embodiments, the device comprises the lower aspect of the insertable portion 107 joining the columella saddle 121 in a manner which allows the fully inserted insertable portion 107 to comfortably bend to the subject's columella shape 10 without affecting the overall positioning of the inserted insertable portion 107. In some embodiments, the two insertable portions 107 can hug the septum 24 and rest comfortably without handholding when fully inserted. In some embodiments, the dual insertable portion can hug the septum 24 and rest comfortably without handholding which could enable passive involvement of the subject for an independently timed actuation. In some embodiments, dosing both nasal channels 20 at the same time removes the concern of nasal cycling, for example, in lower nasal 35 delivery. In some embodiments, averaging both nasal cavities 11 should minimize dosing fluctuations related to dosing to one nasal channel 20 which may be open or congested depending on what stage that nasal channel 20 is in its cycle.

In some embodiments, the at least one cannula is configured for administration of large volumes of drug at once, minimizing time and complexity in rescue situation e.g., reducing multi-administrations for opioid reversal. In some embodiments, the cannula tip comprises a bulbous to facilitate insertion without risk of fetching (e.g., snagging on tissue in the nasal channel). In some embodiments, the cannula lumen can be made of drug compatible materials sheathed in a different material that is biocompatible with the mucus membrane, but not necessarily drug comparable. In some embodiments, the cannula lumen can be made of drug compatible materials sheathed in a different material that is biocompatible with the mucus membrane, but not necessarily drug comparable enables for lower manufacturing expense and complexity. In some embodiments, the lumen can be extruded for consistent inner diameter. In some embodiments, the manufacturing of outer aspects of the cannula can be molded, printed, etc. without concern for the tighter tolerances of the inner diameter. In some embodiments, the lumen can be made of stock material for example a cannula for drug delivery of a different route of administration e.g., hand iv cannula. In some embodiments, the lumen of a sheathed nasal cannula can provide structural strength to the outer sheath allowing the outer sheath to be made of more compliant material that is more comfortable and safer to the mucus membrane. In some embodiments, the device comprises the lumen, wherein the lumen is configured to accommodate different drugs and formulations, e.g., inner diameter, while still using the same outer sheath.

In some embodiments, the device comprises minimizing SKUs and simplifying, e.g., converting filling line from one formulation to another. In some embodiments, the cannula comprises a sheath, wherein the sheath allows for gas (air) or liquid to be simultaneously ejected along deliberate channels in the annulus between the inner lumen and the sheath. In some embodiments, the cannula comprises a cannula annulus that facilitates, e.g., an ejection of gas at the tip of the cannula to assist in liquid jet or spray patterns, or combining with a reactive component of a drug formulation at the time it is ejected an in the body of a subject. In some embodiments, the device comprises a smaller diameter cannula, wherein the cannula is configured to be introduced beyond the nasal channel 20 hairs (avoid a sneeze reflect), the outer nasal channels (avoiding cross contamination of bacteria known to occupy the biome of this aspect of the anatomy), and will not snag on the nasal valve 13 or be diverted back into lower nasal channel 35. In some embodiments, the device comprises a smaller diameter cannula, wherein the small diameter cannula enables access to the tighter space behind the nasal bone, a vantage point which provides a more direct line of sight to the middle meatus 30 or other turbinates. In some embodiments, the smaller diameter cannula is not revealed until after device is inserted.

In some embodiments, the dispensing element 110 is positioned from about 0.1 mm to about 30 mm from the middle meatus 30 or other nasal anatomy. In some embodiments, the distal aspect 131 is positioned from about 0.1 mm to about 25 mm from the middle meatus 30, or other nasal anatomy. In some embodiments, the distal aspect 131 is positioned from about 0.1 mm to about 3 mm, about 0.1 mm to about 5 mm, about 0.1 mm to about 9 mm, about 0.1 mm to about 12 mm, about 0.1 mm to about 18 mm, about 0.1 mm to about 20 mm, about 0.1 mm to about 25 mm, about 3 mm to about 5 mm, about 3 mm to about 9 mm, about 3 mm to about 12 mm, about 3 mm to about 18 mm, about 3 mm to about 20 mm, about 3 mm to about 25 mm, about 5 mm to about 9 mm, about 5 mm to about 12 mm, about 5 mm to about 18 mm, about 5 mm to about 20 mm, about 5 mm to about 25 mm, about 9 mm to about 12 mm, about 9 mm to about 18 mm, about 9 mm to about 20 mm, about 9 mm to about 25 mm, about 12 mm to about 18 mm, about 12 mm to about 20 mm, about 12 mm to about 25 mm, about 18 mm to about 20 mm, about 18 mm to about 25 mm, or about 20 mm to about 25 mm, including increments therein, from the middle meatus 30, or other nasal anatomy. In some embodiments, the tip is positioned from about 0.1 mm, about 3 mm, about 5 mm, about 9 mm, about 12 mm, about 18 mm, about 20 mm, or about 25 mm from the middle meatus 30, or other nasal anatomy. In some embodiments, the tip is positioned from at least about 0.1 mm, about 3 mm, about 5 mm, about 9 mm, about 12 mm, about 18 mm, or about 20 mm from the middle meatus 30, or other nasal anatomy. In some embodiments, the dispensing element is positioned from at most about 3 mm, about 5 mm, about 9 mm, about 12 mm, about 18 mm, about 20 mm, or about 25 mm from the middle meatus 30, or other nasal anatomy.

Figure 7A:
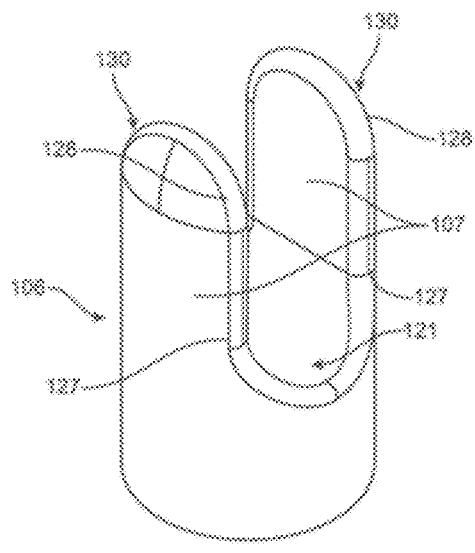
FIG. 7A depicts an exemplary embodiment perspective view of an exemplary insertable portion and a columella subject engaging portion in the first configuration, according to some embodiments.

FIG. 7A depicts an exemplary embodiment perspective view of an Exemplary Columella Saddle in the first configuration. In some embodiments, the device comprises a subject engaging portion 106, a columella saddle 121, and two insertable portions 107.

In some embodiments, the device comprises at least one insertable portion 107. In some embodiments, the device comprises two insertable portions 107. In some embodiments, the at least one insertable portion 107 comprises a shape 130, wherein the shape comprises a wing, a foil, a wedge, an oval or oblong, or even a round form. In some embodiments, the distal end 128 of the insertable portion 107 comprise a rounded shape 130. In some embodiments, the at least one insertable portion 107 comprises a shape 130 whereby an aspect of the at least one insertable portion 107 fits snuggly into the narrow "slit-like" anterior aspect of the internal nasal valve 13 where the septum 24 meets the upper lateral cartilage 25. In some embodiments, the at least one insertable portion 107 has a height of about 10 mm to about 30 mm, a depth of about 3 mm to about 15 mm, and a width of about 1 mm to 5 mm.

In some embodiments, the columella saddle 121 comprises a "U" or "saddle" shape adapted for engaging the columella region 10 of a subject. In some embodiments, the subject engaging portion 106 engages the columella region 10 of the subject about multiple sides of the columella region 10 in a concave shape.

Figure 7B:
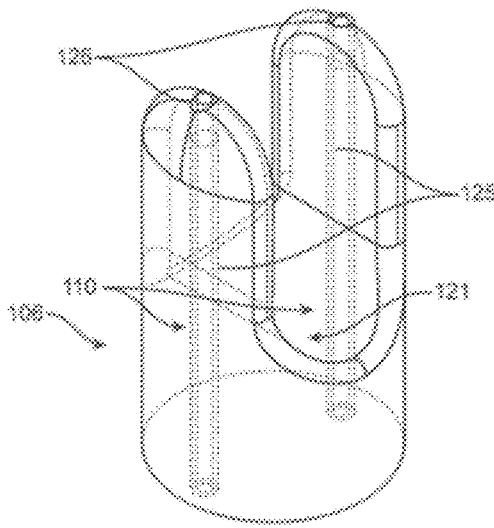
FIG. 7B depicts an exemplary embodiment perspective internal component view of an exemplary insertable portion and a columella subject engaging portion in the first configuration, according to some embodiments.

FIG. 7B depicts an exemplary embodiment perspective internal component view of an exemplary columella saddle in the first configuration. In some embodiments, the device comprises a subject engaging portion 106, the subject engaging portion 106 may function as a positioning element and may include a columella saddle 121, two insertable portions 107, and two dispensing elements or dispensing channels 125 with dispensing ports 126 positioned at the distal aspect 131 of the dispensing elements 125 for delivering a composition 111 to a targeted area of the nasal channels 20, such as the middle meatus 30, or turbinates. In some embodiments, the composition 111 is delivered from both dispensing ports 126 simultaneously. In some embodiments, the composition 111 is delivered from both dispensing ports 126 sequentially. In some embodiments, the dispensing channels 125 may be dispensing elements 110. In some embodiments, the dispensing elements 110 may be cannulas.

In some embodiments, the device comprises at least one dispensing channel 125 and at least one dispensing port 126. In some embodiments, the device comprises two dispensing channels 125 and two dispensing ports 126. In some embodiments, the at least one dispensing channel 125 is unlined. In some embodiments, the at least one dispensing channel 125 is lined with a material that is distinct from the material of the one or more insertable portions 107. In some embodiments, the at least one dispensing channel 125 has an inner diameter 129 of 0.5 mm to 3 mm. In some embodiments, the at least one dispensing channel 125 has a round cylindrical shape. In some embodiments, the at least one dispensing channel 125 has an elliptic cylindrical shape. In some embodiments, the at least one dispensing port 126 delivers a composition 111 to a targeted area of a nasal channel 20, such as the middle meatus 30, or turbinates.

Figure 7C:
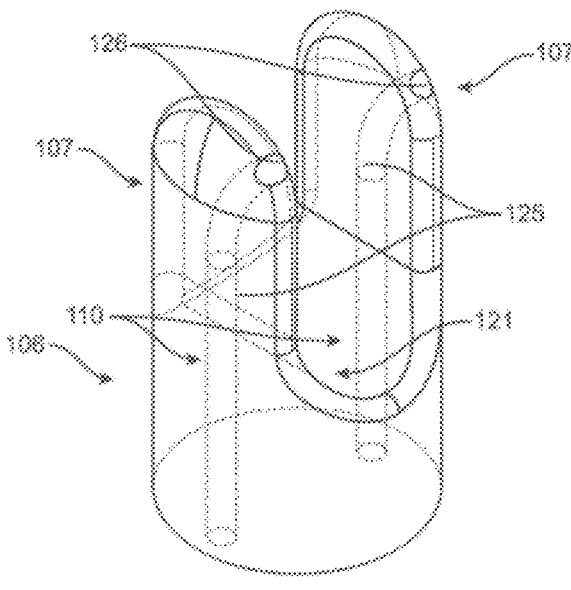
FIG. 7C depicts an exemplary embodiment perspective internal component view of an exemplary insertable portion and a columella subject engaging portion in the first configuration, according to some embodiments.

FIG. 7C depicts an exemplary embodiment perspective internal component view of an Exemplary Columella Saddle in the first configuration. In some embodiments, the device comprises a positioning element, the positioning element comprising a subject engaging portion 106, a columella saddle 121, two insertable portions 107, and two dispensing channels 125 with dispensing ports 126 positioned at a point along the edge of the insertable portions 107 for delivering a composition 111 from the device to a targeted area of the nasal channels 20, such as the middle turbinates 15, or middle meatus 30.

In some embodiments, the device is adapted to target delivery of the composition 111 to a middle meatus 30 or a portion thereof, and the subject engaging portion 106 may align at least one insertable portion 107 or one dispensing element 110 with a middle meatus 30 of the subject. In some embodiments, the at least one dispensing channel 125 within an insertable portion 107, or the at least one dispensing element 110 has an inner diameter 129 of 0.3 to 3.0 mm. In some embodiments, the at least one dispensing channel 125 within an insertable portion 107, or the at least one dispensing element 110 has an inner diameter 129 of 0.3 to 0.7 mm. In some embodiments, the at least one dispensing channel 125 within an insertable portion 107, or the at least one dispensing element 110 has an inner diameter 129 of 0.5 to 1.0 mm. In some embodiments, a wider inner diameter 129 may be used to deliver high viscosity compositions. In some embodiments, the dispensing channel 125 within an insertable portion 107, or the dispensing element 110 may be adapted to deliver a composition 111 having a low, intermediate, or high viscosity.

In some embodiments, the at least one dispensing channel 125 splits into multiple dispensing channels 125 leading to multiple dispensing ports 126 positioned at multiple locations on the at least one insertable portion 107 for delivering a composition to multiple targeted regions 19 of one or both nasal channels 20, such as the olfactory clefts 23, middle meatus 30, and the middle turbinates 15.

Figure 7D:
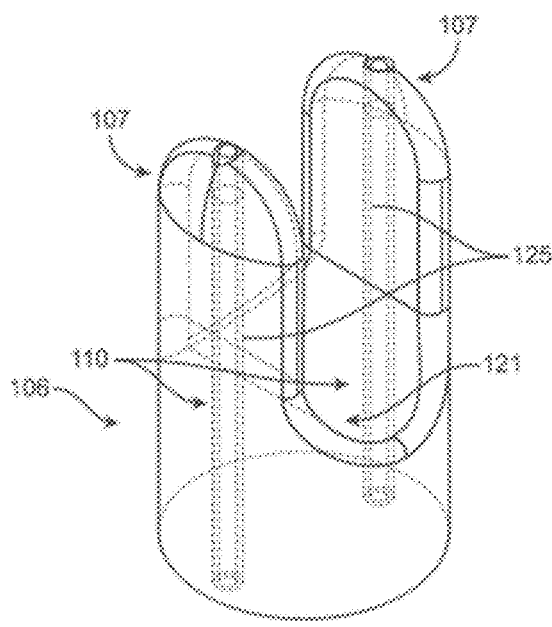
FIG. 7D depicts an exemplary embodiment perspective internal component view of an exemplary insertable portion and a columella subject engaging portion in the first configuration, according to some embodiments.
Figure 7E:
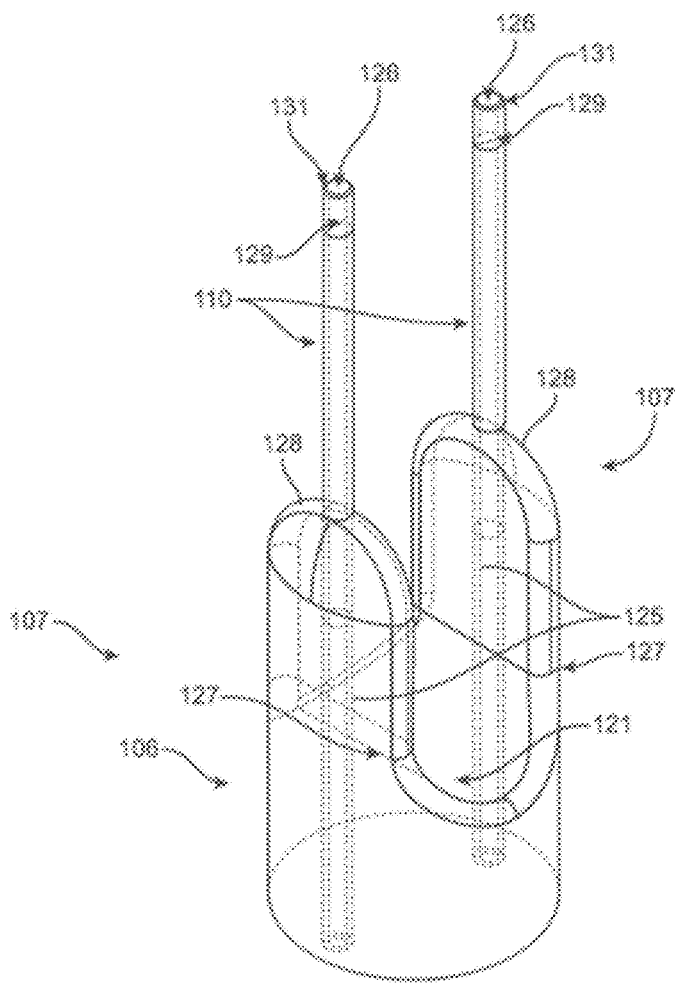
FIG. 7E depicts an exemplary embodiment perspective internal component view of an exemplary insertable portion and a columella subject engaging portion in the second configuration, according to some embodiments.

Referring to FIGS. 7D-7E. In some embodiments, the at least one dispensing element 110 emerges from or is revealed by the at least one insertable portion 107 from the distal aspect 131 of the insertable portion 107 upon transition of the device from the first configuration 100 to the second configuration 200. In some embodiments, the at least one dispensing element 110 emerges from or is revealed by the at least one insertable portion 107 from another aspect of the insertable portion 107, such as along the edge of the at least one insertable portion 107. In some embodiments, the at least one dispensing element 110 is positioned to deliver a composition 111 to a target area in one or both nasal channels 20, such as the middle meatus 30, or the turbinates. In some embodiments, the length of the portion of the at least one dispensing element 110 that extends from or is revealed by the at least one insertable portion 107 is about 5 mm to about 40 mm. In some embodiments, the composition 111 is delivered from both dispensing elements 110 simultaneously. In some embodiments, the composition 111 is delivered from both dispensing elements 110 sequentially.

Figures 25A, 25B:
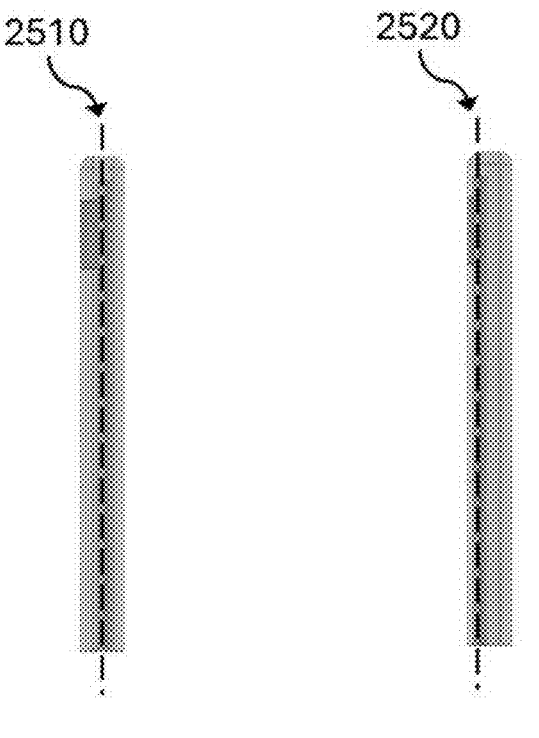
FIGS. 25A-25B depict location of the dispensing channel or lumen within the dispensing element according to some embodiments.

Referring to FIGS. 25A-25B. In some embodiments, the dispensing channel 125 is positioned substantially along a center 2510 of the dispensing element 110 (FIG. 25A). In some embodiments, the position of the dispensing channel 125 in the dispensing element 110 is offset, i.e. the dispensing channel 125 runs off-centered 2520 along the dispensing element 110 (FIG. 25B).

Figures 26A, 26B:
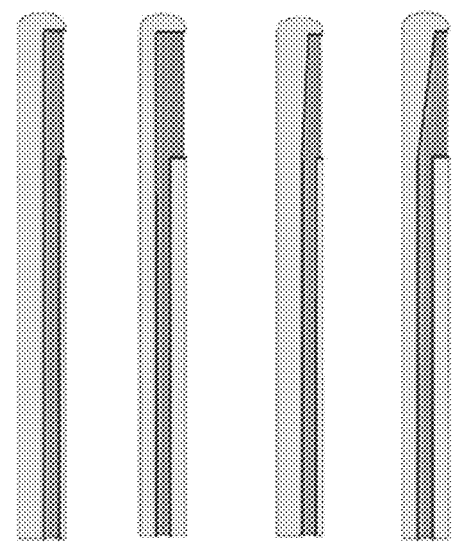
FIGS. 26A-26B depict designs of the dispensing channel according to some embodiments.

Referring to FIGS. 26A-26B. The inner shape of the dispensing channel 125 may be configured to achieve a desired ejection velocity or volumetric flow rate. For example, the dispensing channel may comprise one or more narrowed portion. The dispensing channel may be tapered at a distal end. The dispensing channel may comprise an angled wall. The dispensing channel may comprise substantially parallel walls with the dispensing element.

Referring to FIG. 26B. In some embodiments, a distal portion of the dispensing channel 125 comprises an angled wall 2610 that extends at an angle 2620 from a proximal base 2630. In some embodiments, the proximal base 2630 substantially coincides with a proximal end of the side opening 2010. In some embodiments, the proximal base 2630 does not coincide with a proximal end of the side opening.

Figure 11:
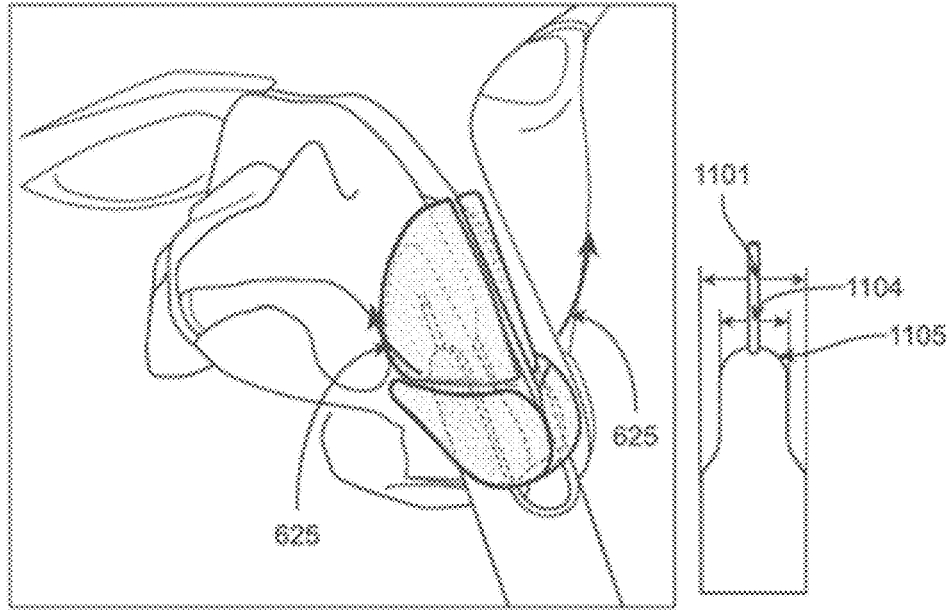
FIG. 11 depicts the anatomy of the nasal cavity in a subject and an exemplary device opening or expanding the internal nasal valve and an exemplary side view of an exemplary insertable portion and a columella subject engaging portion in the first configuration, according to some embodiments.

FIG. 11 depicts the anatomy of the nasal cavity and an exemplary device configuration opening or expanding an exemplary internal nasal valve and an exemplary embodiment side view perspective of an Exemplary Columella Saddle.

In some embodiments, the ejection zone 29 is: 0 mm to 30 mm superior to a horizontal line 627 that intersects the anterior aspect of the internal nasal valve 13, and 0 mm to 20 mm anterior to an inclined line 620 that intersects the anterior aspect of the middle turbinate 15 and the posterior aspect of the vestibule 21.

In some embodiments, the subject engaging portion 106 engages a columella region 10 of the subject to seat a distal end 128 of the insertable portion 107 within an ejection zone 29 of a nasal cavity 11 of the subject, wherein the ejection zone 29 is: 0 mm to 30 mm superior to a horizontal line 627 that intersects the anterior aspect of the internal nasal valve 13, and 0 mm to 20 mm anterior to an inclined line 620 that intersects the anterior aspect of the middle turbinate 15 and the posterior aspect of the vestibule 21, and one or more of the following: 0 mm to 40 mm inferior to a horizontal line 621 that is parallel to the inferior aspect of the olfactory cleft 23, 0 mm to 20 mm posterior to the internal nasal dorsum 622, 10 mm to 50 mm superior to a horizontal line 623 that intersects the inferior aspect of the columella 10, 0 mm to 30 mm superior to a horizontal line 624 that intersects the superior aspect of the inferior turbinate 16, 0 mm to 3 mm from the septum 24 or any combination thereof.

In some embodiments, the subject engaging portion 106 prevents movement of the distal end 128 within or away from the ejection zone 29 when the subject engaging portion 106 is seated on the columella region 10. In some embodiments, the subject engaging portion 106 is seated on the columella region 10 when the subject engaging portion 106 simultaneously contacts a downward facing lateral face of the columella, a leftward facing lateral face of the columella, and a rightward facing lateral face of the columella. In some embodiments, dispensing a composition 111 from the ejection zone 29 increases on target deposition of the composition to an aspect of a respiratory region such as the middle turbinate 15. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the target region 19 is the olfactory region 23 and the middle meatus 30. In some embodiments, the target region 19 is the olfactory region 23 and the middle meatus 30, wherein the composition is dispensed to both regions simultaneously. In some embodiments, the target region 19 is the olfactory region 23 and the middle meatus 30, and other regions of the nasal anatomy. In some embodiments, the target region 19 is the olfactory region 23 and the middle meatus 30, and other regions of the nasal anatomy, wherein the composition is dispensed to all regions simultaneously.

In one aspect, the disclosure provides a device for intra-nasal delivery to a subject, the device transitionable from a first configuration 100 to a second configuration 200, the device comprising: a housing 101 defining a first insertable portion 100 configured to be inserted into a nasal channel 20 of the subject; and a dispensing element 110 coupled to the housing 101, the dispensing element 110 revealing from the first insertable portion 107 upon transition of the device from the first configuration 100 to the second configuration 200, wherein the device is transitioned from the first configuration 100 to the second configuration 200 by applica-tion of pressure about a longitudinal axis 610 of the device, and wherein the device is simultaneously actuated upon being transitioned from the first configuration 100 to the second configuration 200. In some embodiments, the simul-taneous actuation refers to transition for the first configura-tion 100 to the second configuration 200 and actuation occurring in a single motion upon application of pressure about a longitudinal axis 610 of the device.

In some embodiments, the dispensing element 110 reveals in a linear vector parallel to the internal nasal dorsum 622 from the first insertable portion 100 at a location above an inferior turbinate 16 of the subject. In some embodiments, the device avoids contaminating the dispensing element with bacteria from the lower nasal cavity by enclosing it in the insertable portion 107 prior to revealing the dispensing element 110 upon transition from the first configuration 100 to the second configuration 200. In some embodiments, the device avoids contaminating the dispensing element 110 by concealing it within the insertable portion 107 prior to actuation.

In some embodiments, the first and second dispensing elements 110 move along a septum 24. In some embodi-ments, the two insertable portions 107 each contact opposite sides of a septum 24. In some embodiments, the two dispensing elements 110 each contact opposite sides of a septum 24. In some embodiments, the two insertable por-tions 107 each contact opposite sides of a septum 24 and apply force to a superior lateral cartilage 25 in a direction away from the septum 24. In some embodiments, the two insertable portions 107 each contact opposite sides of a septum 24 and apply force to a superior lateral cartilage 25 in a direction orthogonal to a lateral axis of the septum 24. In some embodiments, the at least one insertable portion 107 to open or expand an internal nasal valve 13 does so by moving a superior lateral cartilage 25 defining the internal nasal valve 13 away from a septum 24 of the subject. In some embodiments, the at least one insertable portion 107 to open or expand an internal nasal valve 13 does so by moving superior cartilage 25 defining the internal nasal valve 13 towards an internal nasal dorsum 622 of the subject.

Figure 6A:
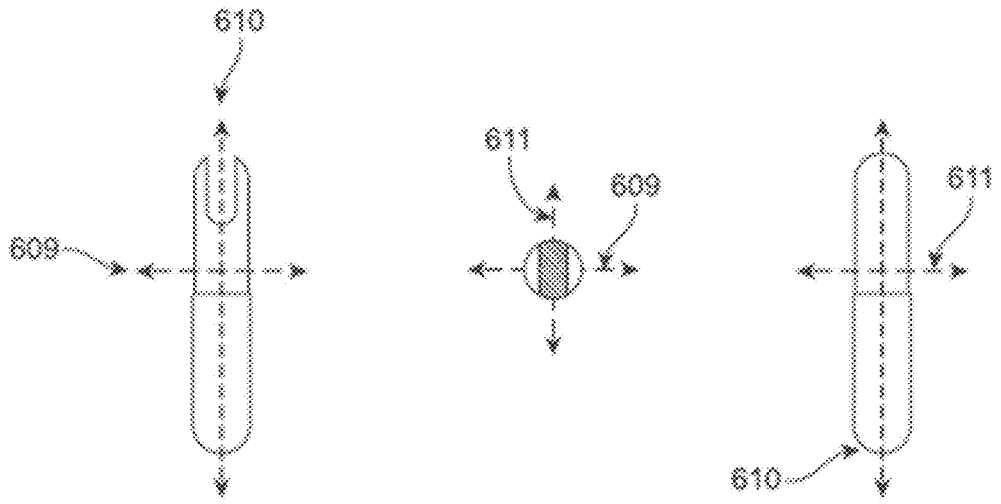
FIG. 6A depicts an exemplary embodiment of a cartesian reference plane of (left to right) a front, a top, and a side view of an Exemplary Device, according to some embodiments.
Figure 6B:
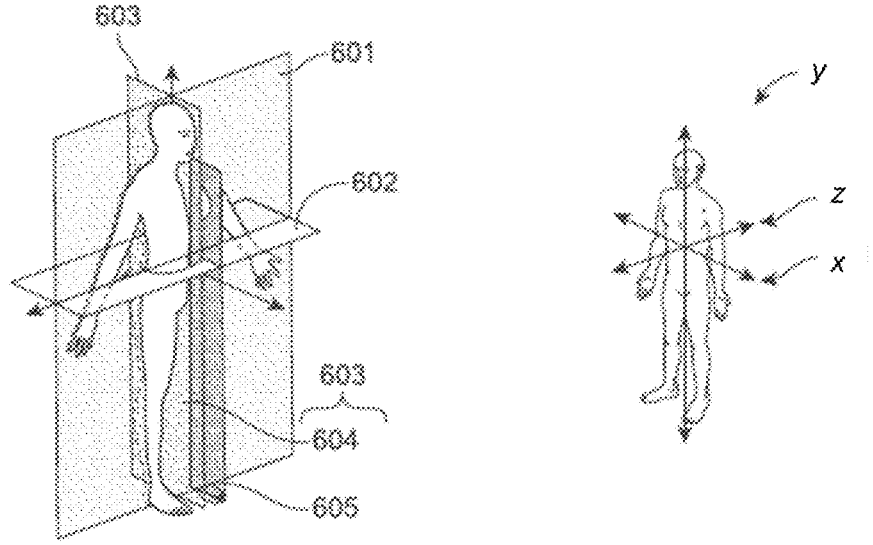
FIG. 6B depicts an exemplary embodiment of the subject plane, according to some embodiments.

Referring to FIGS. 6A-6C. In some embodiments, the device is configured for a subject having a coronal plane 601, horizontal or axial or transverse plane 602, sagittal plane 603, median plane 604, or parasagittal plane 605, or combination thereof. In some embodiments, the device comprises a relative angular coordinate system of roll on the Y-axis of the device, pitch on the device sagittal plane 607, and yaw on the device coronal plane 608. In some embodi-ments the device is configured for a subject having a subject's linear coordinate system x relative to subject's medial/lateral, y relative to subject superior/inferior, and z relative to subject anterior/posterior.

Figure 6D:
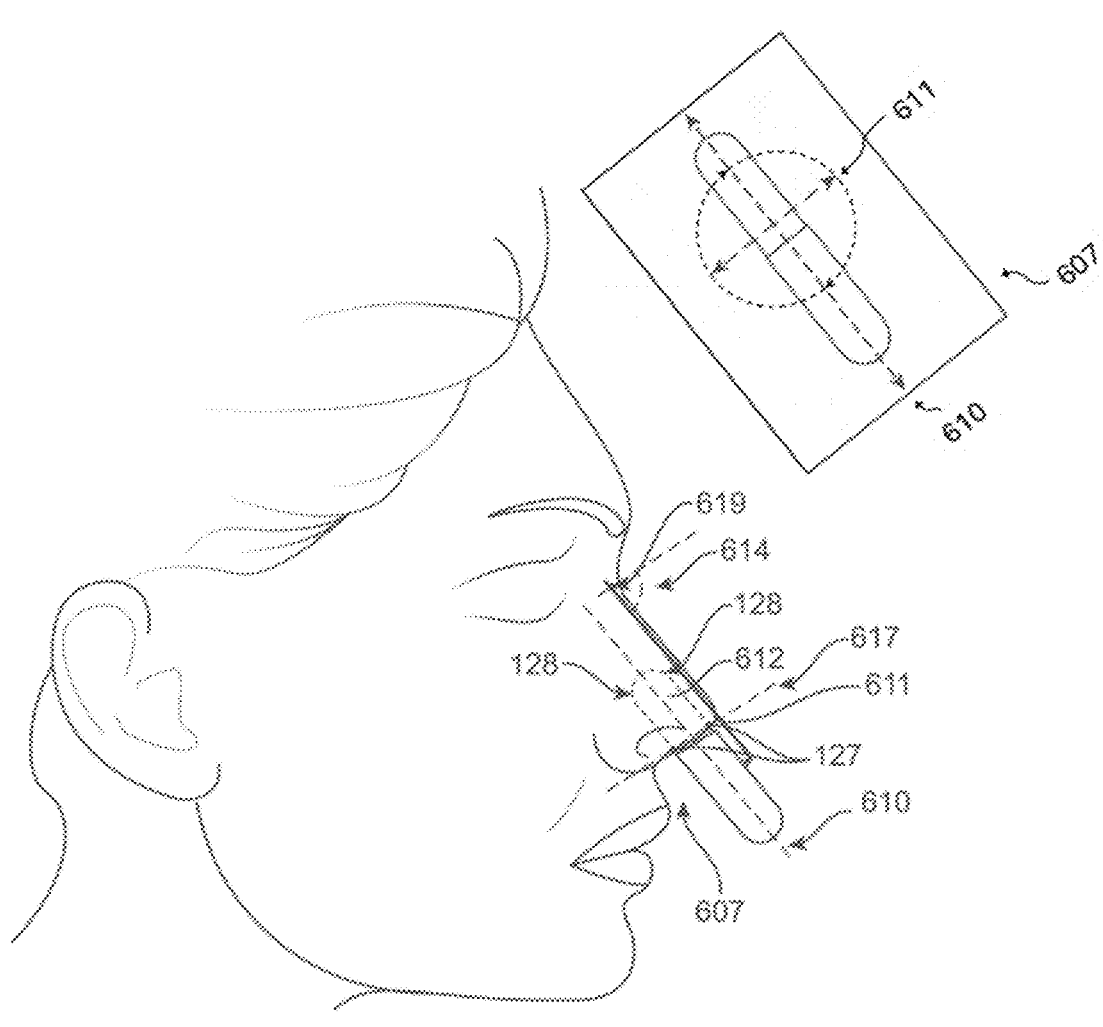
FIG. 6D depicts an exemplary embodiment of an Exemplary Device Sagittal Angle positioning in the subject, according to some embodiments.

Referring to FIG. 6D. In some embodiments, the insert-able portions 107 are positioned along its y-axis in relation to other anatomy, creating a predictable/repeatable relation-ship with regards to the devices pitch angle on the subject's sagittal plane 603. In some embodiments, from the devices predictable/repeatable relationship to other anatomy, the pitch angle can be related to known anthropometric data. In some embodiments, the insertable portions 107 are config-ured to follow the shape of the interior dorsum wall 612, and lateral aspects of the septum 24 in the nasal cavity 11, allowing it to maintain a consistent and repeatable angle on the sagittal plane 603, wherein this positioning is achieved when the insertable portions 107 are inserted past the nasal vestibule 21 and into the nasal cavity 11. In some embodi-ments, the insertable portions 107 are configured to hold it to, and guide it along, the soft tissues of the interior dorsum wall 612, ensuring that it remains parallel to these tissues. In some embodiments, as the tissues of the interior dorsum wall 612 are parallel to known anthropometric axis 613 drawn from nasion 619 to tip, used in both the nasofacial and nasofrontal angle 614, a known angler anthropometric range can be determined for the position of the inserter longitu-dinal axis 610 on the sagittal plane 603 relative to subject anatomy.

Figure 6E:
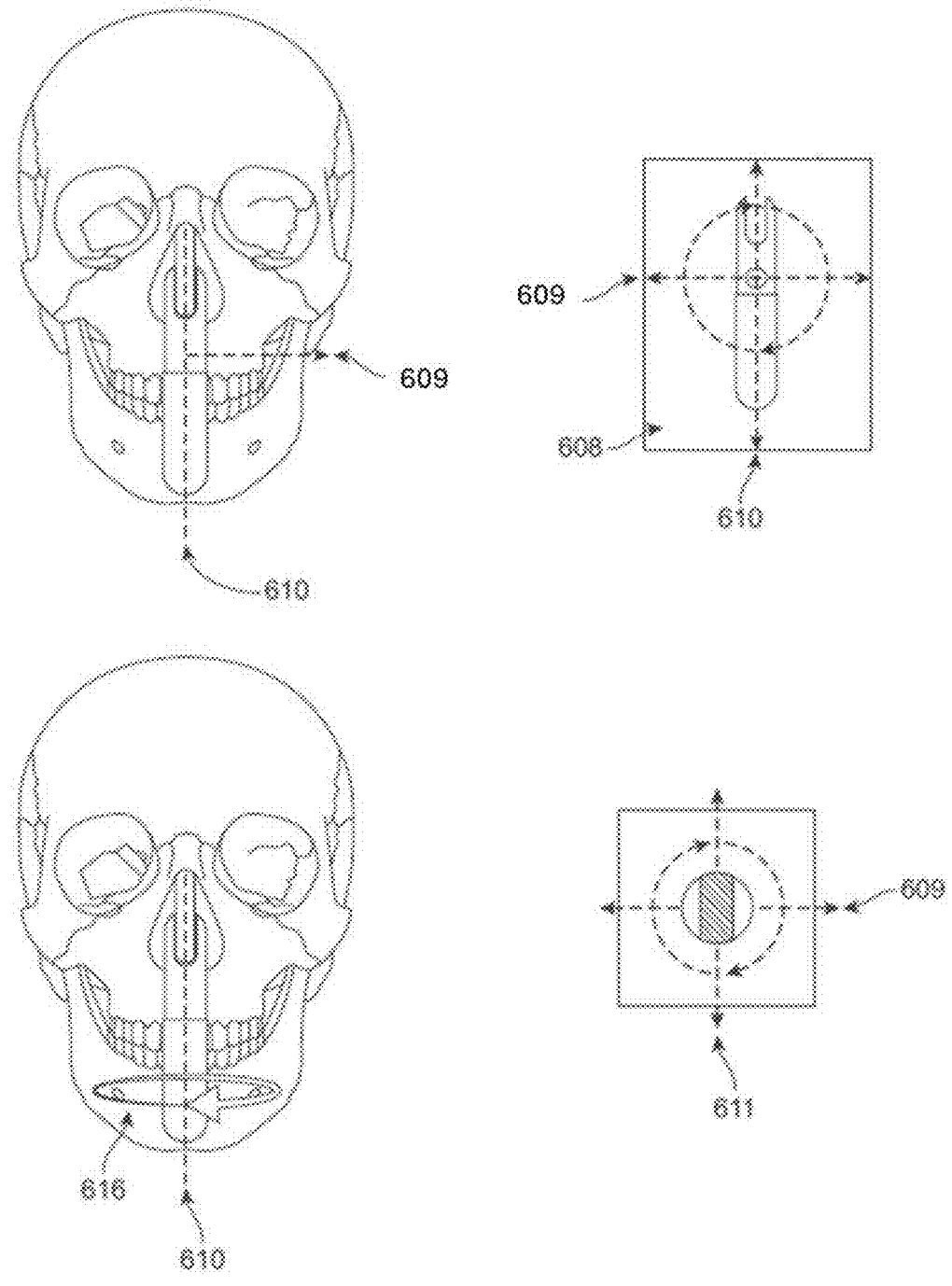
FIG. 6E depicts an exemplary embodiment of an Exemplary Device Coronal-Medial Angle positioning in the subject, along a front view of the Coronal Plane, and a top view along a transverse plane, according to some embodiments.

Referring to FIG. 6E. In some embodiments, the insert-able portions 107 are designed to interlock with the nasal cavity 11. In some embodiments, the insertable portions 107 are configured to key medial to the lateral aspects of septal cartilage, and bilaterally to the greater alar and lateral nasal cartilage, including the connective tissues of these struc-tures. In some embodiments, the insertable portions 107 are locked in the y-axis rotation along the device 616, and locked in medially/laterally 609.

Figure 6F:
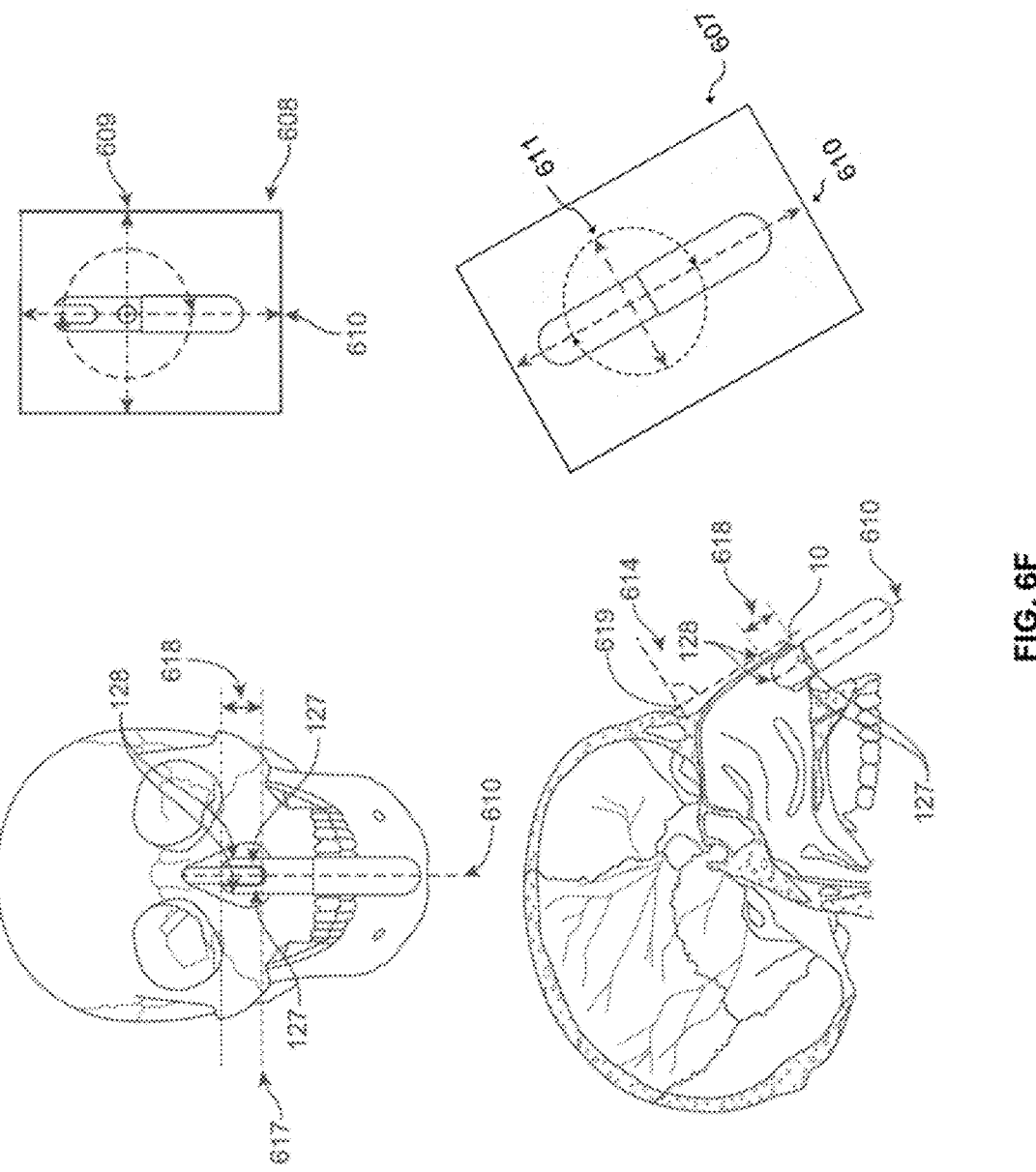
FIG. 6F depicts an exemplary embodiment of an Exemplary Device Depth positioning along a front view of the Coronal Plane, and along a side view of the Sagittal Plane in the subject, according to some embodiments.

Referring to FIG. 6F. In some embodiments, the insertable portions 107 are designed to position and interlock within the nasal cavity 11, creating a predictable/repeatable depth r 618. In some embodiments, the insertable portions 107 are designed to key and hard stop on the columella 10 its supporting structures, e.g., the nasal spine and septal carti-lage. In some embodiments, as the columella 10 comprises a depth datum 617 along the device y-axis, the ejection ports 126, e.g., along the cannulas, of the insertable portions 107 may be placed at desired and known distance from a target anatomy.

Figure 6G:
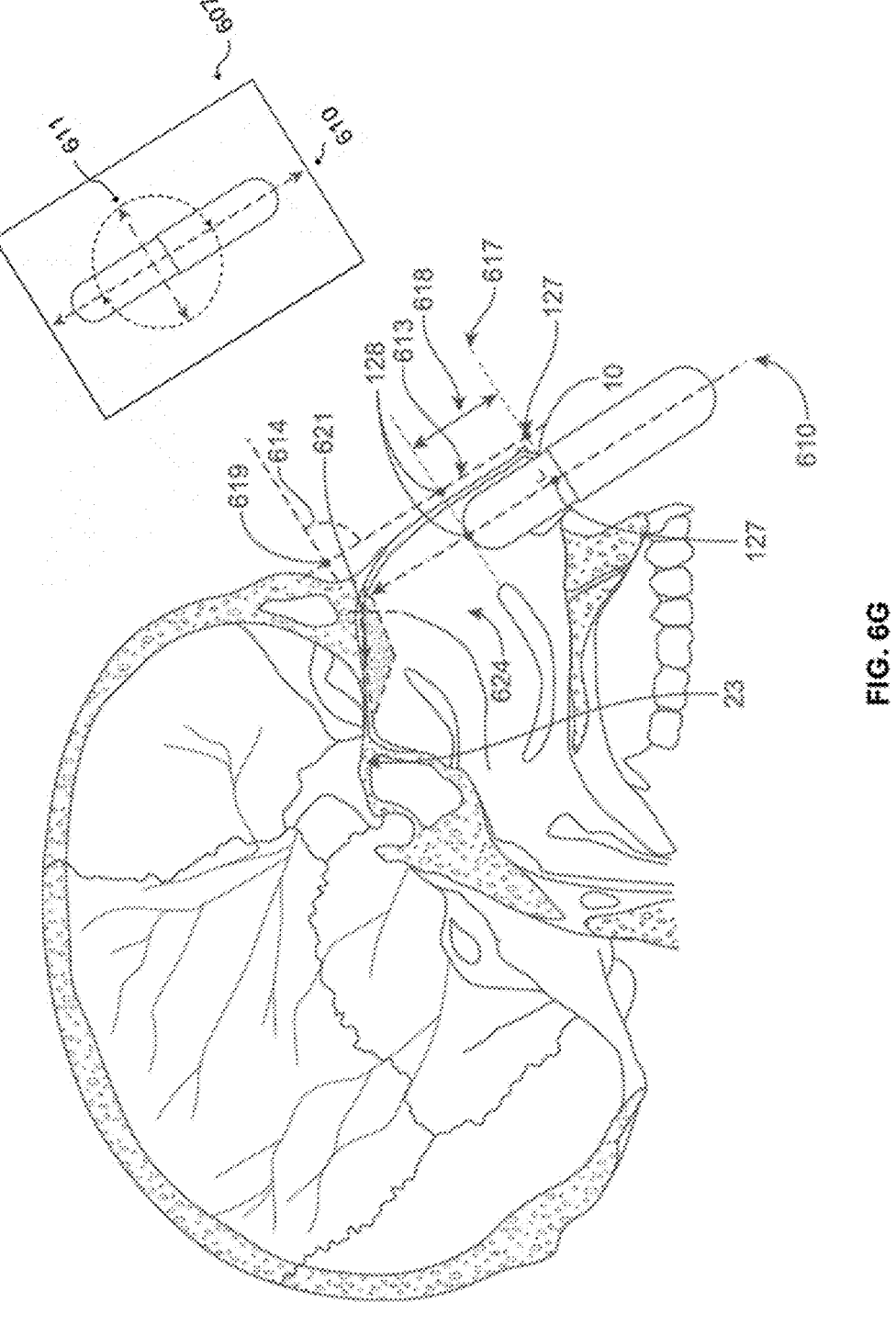
FIG. 6G depicts an exemplary embodiment of an Exemplary Device along a side view of the sagittal plane of delivery to the target region in the subject, according to some embodiments.

Referring to FIG. 6G. In some embodiments, with a known depth 618, Cartesian and angular reference of the insertable portions 107 relative to subject anatomies in the subject anatomy, exit ports, e.g., dispensing ports 126 along one or more dispensing elements 110, may be placed in a desired location to create a desired trajectory of the dose and a relative fluid profile and velocity may be chosen to deliver the composition 111 to a desired location, e.g., target region 19, repeatably and accurately. In some embodiments, a coherent jet may be formed along the z-axis of the device, creating a substantially unimpeded flow to the turbinates, e.g., superior turbinate 14, middle turbinate 15, or inferior turbinate 16, or a combination thereof.

Figure 6H:
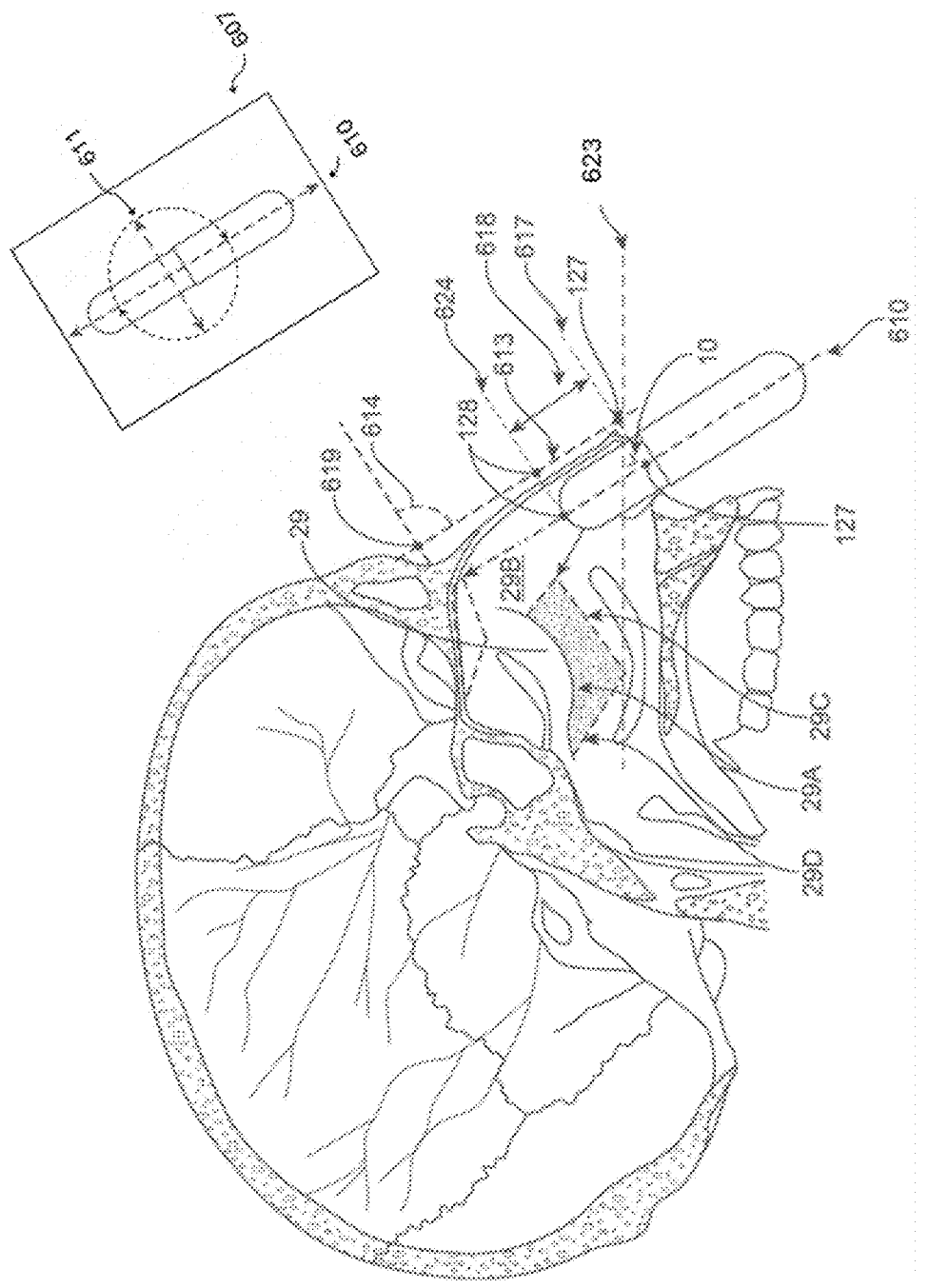
FIG. 6H depicts an exemplary embodiment of an Exemplary Device along a side view of the sagittal plane aiming from the respiratory region in the subject, according to some embodiments.

Referring to FIG. 6H. In some embodiments, the ejection zone 29 comprises a trapezium or irregular quadrilateral comprising (i) an inferior side 29A being a 10-25 mm line extending posteriorly and horizontally from the anterior aspect of the internal nasal valve 13, (ii) an anterior side 29B being a 10-35 mm line extending superiorly and parallel to the internal nasal dorsum 622 from the anterior aspect of the internal nasal valve 13, (iii) a superior side 29C being a 10-25 mm line extending posteriorly and horizontally from a point on the internal nasal dorsum 622 that is 0-10 mm inferior to the inferior aspect of the olfactory cleft 23, and (iv) a posterior line 29D being a 10-35 mm line extending vertically along a plane that intersects the anterior aspect of the middle turbinate 15

In some embodiments, the at least one insertable portion 107 fits proximal to a septal-lateral cartilage junction 27 of the subject. In some embodiments, the dispensing element 110 fits proximal to a septum 24 of the subject. In some embodiments, the dispensing element 110 comprises one or more cannulas. In some embodiments, the dispensing element 110 comprises one or more cannulas which are fixed relative to the insertable portion 107. In some embodiments, the dispensing element 110 comprises one or more cannulas which reveal from the insertable portion 107 when the device is transitioned from the first configuration 100 to the second configuration 200. In some embodiments, the insertable portion 107 comprises the dispensing element 110. In some embodiments, the insertable portion 107 is the dispensing element 110. In some embodiments, the one or more dispensing elements 110 comprises one or more cannulas, wherein the one or more cannulas comprise one or more dispensing ports 126. In some embodiments, the dispensing port 126 comprises one ejection port at its distal end. In some embodiments, the dispensing port 126 comprises one or more ejection ports 126 along its length. In some embodiments, the dispensing port 126 comprises one ejection port at its distal end, one or more ejection ports along its length, or a combination of both.

In some embodiments, the dispensing port 126 is directed at different target areas within the nasal channel 20. In some embodiments, the device ejects fluid from above the internal nasal valve 13. In some embodiments, the device ejects fluid from at least approximately 15-20 mm above the columella 10. In some embodiments, the device ejects fluid from above the area of primary high velocity/low pressure airflow. In some embodiments, the device ejects fluid from at least 25-30 mm from the columella region 10. In some embodiments, the dispensing port 126 comprises an atomizer. In some embodiments, the one or more dispensing elements are about 5-40 mm in length. In some embodiments, the one or more dispensing elements 110 reveal about 5-40 mm from the housing. In some embodiments, at least one dispensing element 110 is at least partially contained within the housing 101. In some embodiments, at least one dispensing element 110 reveals outwards from the housing 101 when in the second position 200. In some embodiments, the one or more dispensing elements 110 comprise multiple ejection ports 126. In some embodiments, the one or more dispensing elements 110 comprise multiple fluid channels 125. In some embodiments, one of the multiple fluid channels 125 are configured to dispense a gas 111. In some embodiments, one of the multiple fluid channels 125 is configured to dispense a gas 111 following dispensing a composition 111 by another fluid channel 125.

Figure 8A:
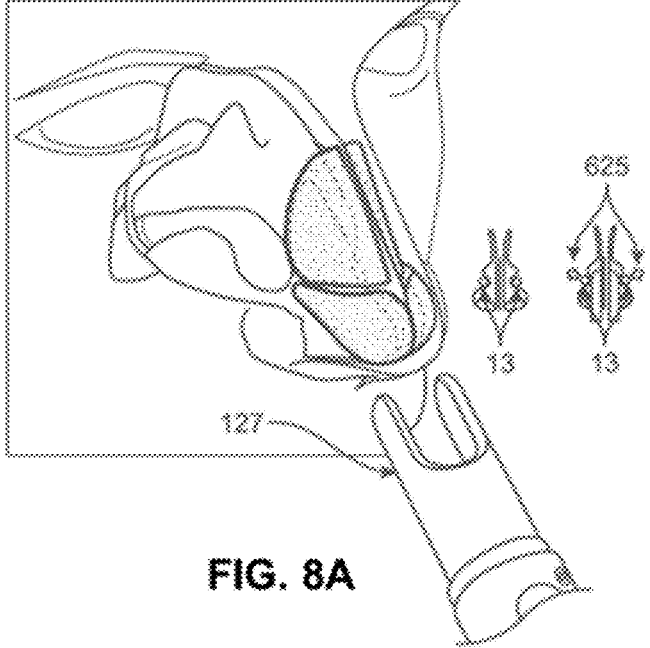
FIG. 8A depicts the anatomy of the nasal cavity in a subject and an exemplary device configuration, according to some embodiments.
Figure 8B:
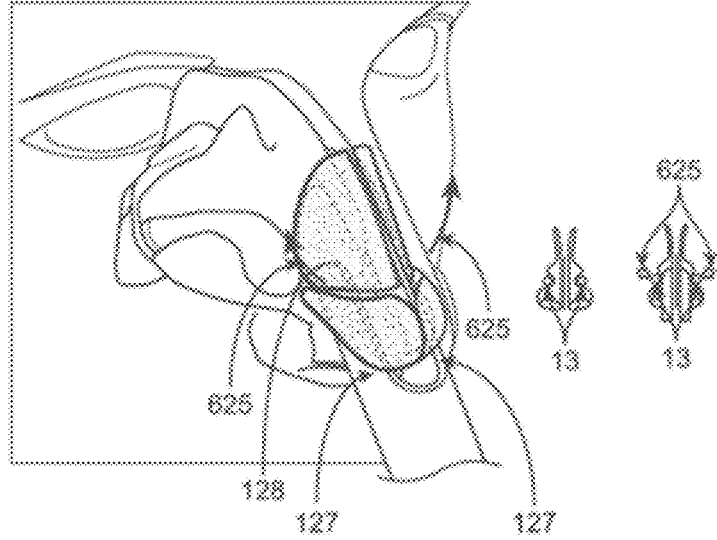
FIG. 8B depicts the anatomy of the nasal cavity in a subject and an exemplary device configuration opening or expanding an exemplary internal nasal valve, according to some embodiments.
Figure 10:
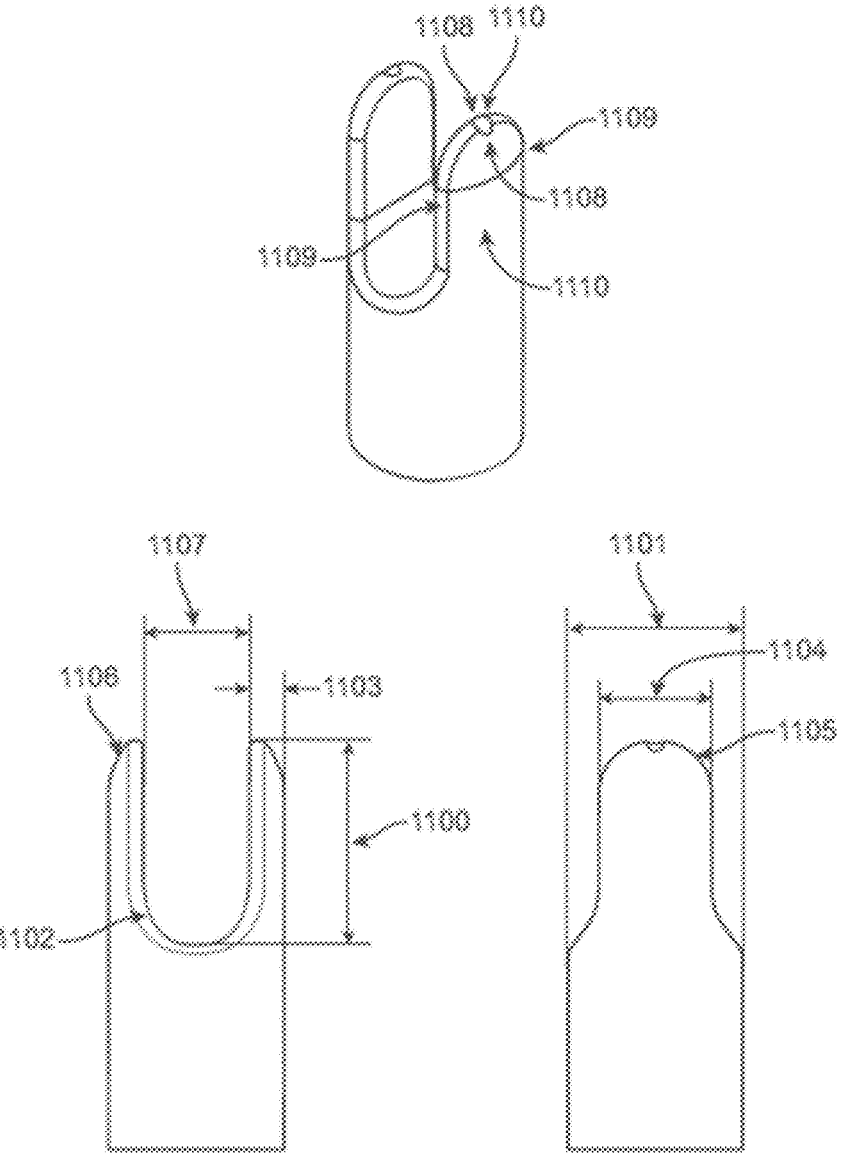
FIG. 10 depicts an exemplary embodiment perspective, front and side view of an Exemplary Columella Saddle in the first configuration, according to some embodiments.

Referring to FIGS. 8A-8B. The anatomy of the subject's nasal cavity 11 comprises the internal nasal valve 13. In some embodiments, the dispensing tip avoids the less predictable and sensitive thicker, softer tissue. FIG. 10 depicts an exemplary embodiment perspective, front and side view of an Exemplary Columella Saddle in the first configuration, according to some embodiments. In some embodiments, the device comprises a length 1100 of the insertable portions 107 from the base of the "U" shaped columella saddle 121 to the distal end 128 of the insertable portions 107. In some embodiments, the length 1100 of the insertable portions 107 from the base of the "U" shaped columella saddle 121 to the distal end 128 of the insertable portions 107 is about 20 mm. In some embodiments, the length 1100 of the insertable portions 107 from the base of the "U" shaped columella saddle 121 to the distal end 128 of the insertable portions 107 is between about 1 mm to about 20 mm. In some embodiments, the length 1100 of the insertable portions 107 from the base of the "U" shaped columella saddle 121 to the distal end 128 of the insertable portions 107 is between about 1 mm to about 25 mm. In some embodiments, the device comprises the depth 1101 of the distal end 128 of the insertable portions 107 from the base of the "U" shaped columella saddle 121. In some embodiments, the device comprises the depth 1101 of the base of the "U" shaped columella saddle 121 is about 17 mm. In some embodiments, the device comprises the depth 1101 of the base of the "U" shaped columella saddle 121 between about 1 to about 17 mm. In some embodiments, the device comprises the depth 1101 of the base of the "U" shaped columella saddle 121 between about 1 to about 22 mm. In some embodiments, the device comprises the radius 1102 of the "U" shaped s columella addle 121. In some embodiments, the radius 1102 of the "U" shaped saddle 121 is about 5 mm. In some embodiments, the radius 1102 of the "U" shaped columella saddle 121 is between about 1 mm to about 5 mm. In some embodiments, the radius 1102 of the "U" shaped columella saddle 121 is between about 1 mm to about 10 mm. In some embodiments, the device comprises the width 1103 of the insertable portions 107 at the vertical mid-point. In some embodiments, the width 1103 of the insertable portions 107 at the vertical mid-point is about 3.5 mm. In some embodiments, the width 1103 of the insertable portions 107 at the vertical mid-point is between about 1 mm to about 3.5 mm. In some embodiments, the width 1103 of the insertable portions 107 at the vertical mid-point is between about 1 mm to about 7 mm. In some embodiments, the device comprises the length 1100 of the insertable portions 107 at the vertical mid-point. In some embodiments, the length 1100 of the insertable portions 107 at the vertical mid-point is about 11 mm. In some embodiments, the length 1100 of the insertable portions 107 at the vertical mid-point is between about 1 mm to about 11 mm. In some embodiments, the length 1100 of the insertable portions 107 at the vertical mid-point is between about 1 mm to about 16 mm. In some embodiments, the device comprises the width 1104 of the insertable portions 107 at the vertical mid-point. In some embodiments, the width 1104 of the insertable portions 107 at the vertical mid-point is about 11 mm. In some embodiments, the width 1104 of the insertable portions 107 at the vertical mid-point is between about 1 mm to about 11 mm. In some embodiments, the width 1104 of the insertable portions 107 at the vertical mid-point is between about 1 mm to about 16 mm. In some embodiments, the device comprises the radius 1105 of the distal end 128 of the insertable portions 107 (along the depth). In some embodiments, the radius 1105 of the distal aspect of the insertable portions 107 (along the depth) is about 5.5 mm. In some embodiments, the radius 1105 of the distal aspect of the insertable portions 107 (along the depth) is between about 1 mm to about 5.5 mm. In some embodiments, the radius 1105 of the distal aspect of the insertable portions 107 (along the depth) is between about 1 mm to about 10 mm. In some embodiments, the device comprises the radius 1106 of the distal edge of the insertable portions 107 (along the width). In some embodiments, the device comprises the radius 1106 of the distal edge of the insertable portions 107 (along the width) is about 8.5 mm. In some embodiments, the device comprises the radius 1106 of the distal edge of the insertable portions 107 (along the width) is between about 1 mm to 8.5 mm. In some embodiments, the device comprises the radius 1106 of the distal edge of the insertable portions 107 (along the width) is between about 1 mm to 13.5 mm. In some embodiments, the device comprises the width 1107 between insertable portions 107 at the vertical mid-point. In some embodiments, the width 1107 between insertable portions 107 at the vertical mid-point is about 10 mm. In some embodiments, the width 1107 between insertable portions 107 at the vertical mid-point is between about 1 mm to about 10 mm. In some embodiments, the width 1107 between insertable portions 107 at the vertical mid-point is between about 1 mm to about 15 mm.

In some embodiments, the insertable portion 107 is configured to fit into a wedge shape of a nasal valve 13 where a septum 24 contacts a superior lateral cartilage 25. In some embodiments, the anterior aspect of the insertable portion 107 is configured to fit into the narrow anterior aspect of the internal nasal valve 13. In some embodiments, the anterior aspect of the insertable portion 107 is configured to fit into an opening comprising a 9 to 15 degree angle with reference to the septum wall. In some embodiments, the insertable portion 107 is configured to fit into the narrow anterior aspect of the internal nasal valve 13 when seated about the columella region 10. In some embodiments, the insertable portion 107 is configured to fit into an opening comprising a 9 to 15 degree angle with reference to the septum wall when seated about the columella region 10. In some embodiments, the insertable portion 107 is configured to be inserted into a wedge shaped internal nasal valve 13 of a subject. In some embodiments, the insertable portion 107 is tapered about a distal end 128 of the insertable portion 107 and is configured to be inserted into a wedge shaped internal nasal valve 13 of a subject. In some embodiments, the insertable portion 107 is tapered about a distal end 128 of the insertable portion 107 with rounded edges 130 and is configured to be inserted into a wedge shaped internal nasal valve 13 of a subject. In some embodiments, the insertable portion 107 comprises a tip portion having a width 1104 which corresponds to an average diameter of an internal nasal valve 13. In some embodiments, the insertable portion 107 comprises a flat surface on a lateral face of the insertable portion 107 which contacts the septum 24. In some embodiments, the insertable portion 107 comprises a rounded surface on a lateral face of the insertable portion which is opposite the septum 24. In some embodiments, the insertable portion 107 comprises a width 1103 up to 3 mm. In some embodiments, the insertable portion 107 comprises a width 1103 up to 3.5 mm. In some embodiments, the insertable portion 107 comprises a width 1103 up to 5 mm. In some embodiments, one or both insertable portions 107 comprises a distal end 128, wherein a dispensing element 110 reveals from the distal end 128 of the insertable portion 107. In some embodiments, the distal end 128 of an insertable portion 107 is configured for insertion into the nasal channel 20 of the subject. In some embodiments, the revealing of the dispensing element 110 from the first insertable portion 107 upon transition of the device from the first configuration 100 to the second configuration 200 comprises extending of the dispensing element 110 from the first insertable portion 107. In some embodiments, the subject engaging portion 106 engages both a right side and a left side of the columella region 10. In some embodiments, the subject engaging portion 106 comprises a concave shape. In some embodiments, the subject engaging portion 106 comprises a U shape. In some embodiments, the subject engaging portion 106 comprises a saddle shape. In some embodiments, the subject engaging portion 106 comprises a concave ellipsoidal shape. In some embodiments, the subject engaging portion 106 comprises a trench with a rounded bottom or rounded edges. In some embodiments, the subject engaging portion 106 centers the two insertable portions 107 about the subject's columella 10.

In some embodiments, a first insertable portion 107 comprises a single dispensing channel 125 leading to a dispensing port 126 positioned at the distal aspect 128 of the insertable portion 107 and a second insertable portion 107 comprises a single dispensing channel 125 leading to a dispensing port 126 positioned along the length 1100 of the insertable portion 107. In some embodiments, a first insertable portion 107 comprises a single dispensing channel 125 leading to a dispensing port 126 positioned at the distal aspect 128 of the insertable portion 107 and a second insertable portion 107 comprises two or more dispensing channels 125 leading to two or more dispensing ports 126 positioned at various aspects of the insertable portion 107.

In some embodiments, the dispensing element 110 is positioned 0 mm to about 40 mm from the inferior aspect of an olfactory cleft 23 of the subject when the subject engaging portion 106 is engaging the columella 10 of the subject. In some embodiments, the dispensing element 110 is positioned 0 mm to about 40 mm from the middle meatus 30 of the subject when the subject engaging portion 106 is engaging the columella 10 of the subject. In some embodiments, the dispensing element 110 is positioned 0 mm to about 40 mm from the middle turbinate 15 of the subject when the subject engaging portion 106 is engaging the columella 10 of the subject. In some embodiments, the saddle 121 comprises an impression of the subject's columella 10.

In some embodiments, the subject engaging portion 106 comprises dimension of about 20 mm by about 17 mm.

In some embodiments, the columella saddle 121 engages the columella 10 of the subject about multiple sides of the columella 10. In some embodiments, the subject engaging portion 106 depresses a trigger release 104 coupled to the subject engaging portion 106 to actuate the device. In some embodiments, the first and/or second insertable portion 107 limits a sagittal angle or an anterior-posterior 611 angle of the device. In some embodiments, the first and/or second insertable portion 107 limits a coronal angle or a medial-lateral 609 angle of the device. In some embodiments, the first and/or second insertable portion 107 limits a sagittal angle or an anterior-posterior 611 angle of the device. In some embodiments, the first and/or second insertable portion 107 and subject engaging portion 106 limits a sagittal angle, an anterior-posterior 611 angle of the device, a coronal angle or a medial-lateral 609 angle of the device, a sagittal angle or an anterior-posterior 611 angle of the device, or any combination thereof.

In some embodiments, an internal nasal valve 13 of the subject is bounded medially by the septum 24, laterally by the caudal portion of the upper lateral cartilage 25 and inferiorly by the head of the inferior turbinate 16. In some embodiments, the first and/or second insertable portion 107 displaces the upper lateral cartilage 25 thereby opening or enlarging at least a portion of the internal nasal valve 13 of the subject.

In some embodiments, the first and/or second insertable portion 107 is torsionally flexible. In some embodiments, the first and/or second insertable portion 107 is tortionally flexible so as to adjust to the angle of an anterior aspect or wedge of the internal nasal valve 13. In some embodiments, the at least one insertable portion 107 comprises the following flexibility characteristics: a medial-lateral flexibility 1108 along a width 1103 orthogonal to a length 1100 of the insertable portion; a lack of anterior-posterior flexibility 1109 about a length 1100 of the insertable portion 107; an inferior-superior flexibility 1110 about a rotational axis orthogonal to a length 1100 of the insertable portion, or a combination thereof.

In some embodiments, the first and/or second insertable portion 107 comprises dimension of about 20 mm by about 3.5 mm.

In some embodiments, the first and/or second insertable portion 107 are shaped 130, wherein the shape comprises a wedge-shaped, paddle-shaped, cylindrical, bulbous, cone-shaped, spherical, hemispherical, or any combination thereof.

In some embodiments, the housing 101 is movable from a first position to the second position. In some embodiments, the housing 101 comprises a first portion 1020 and a second portion 105, wherein the second portion 105 is pushed relative to the first portion 1020 to actuate the device when the housing 101 is transitioned from the first configuration 100 to the second configuration 200. In some embodiments, the first portion 1020 is inserted into the second portion 105 when the housing 101 is transitioned from the first configuration 100 to the second configuration 200. In some embodiments, upon transition from the first configuration 100 to the second configuration 200, the second portion 105 moves relative to the subject, while the first portion 1020 remains stationary relative to the subject, wherein the first portion 1020 is coupled to the dispensing element 110. In some embodiments, upon transition from the first configuration 100 to the second configuration 200, the dispensing element 110 reveals outward from the first portion 1020.

In some embodiments, the one or more dispensing elements 110 are 20 mm to 50 mm in length. In some embodiments, the one or more dispensing elements 110 reveal 0 mm to 40 mm from the insertable portion 107. In some embodiments, the one or more dispensing elements 110 comprise multiple dispensing ports 126. In some embodiments, the one or more dispensing elements 110 comprise multiple fluid channels 125. In some embodiments, the one or more dispensing elements 110 comprise a dispensing port 126. In some embodiments, one of the multiple fluid channels 125 is configured to dispense a gas. In some embodiments, one of the multiple fluid channels 125 is configured to dispense a gas following dispensing a composition 111 by another fluid channel 125. In some embodiments, the target region 19 is the middle meatus 30, and wherein dispensing the composition 111 from a posterior end of the dispensing element 110 increases on target delivery of the composition 111 to the target region 19.

In some embodiments, the one or more dispensing elements 110 comprise a first tubular section which surrounds the dispensing element 110. In some embodiments, the first tubular section remains within a first insertable portion 107 when the device is actuated to the second position 200. In some embodiments, the insertable portion 107 is flexible. In some embodiments, the one or more dispensing elements 110 are flexible. In some embodiments, the device further comprises a reservoir fluidically connected to the one or more insertable portions 107. In some embodiments, the device further comprises a reservoir fluidically connected to the one or more dispensing elements 110.

In some embodiments, the compound 111 comprises a therapeutic agent. In some embodiments, the compound 111 comprises a liquid, or gas, or a combination thereof.

In some embodiments, the actuator is spring loaded. In some embodiments, the actuator dispenses approximately equal amounts of fluid 111 from each insertable portion 107. In some embodiments, the actuator dispenses approximately equal amounts of fluid from each dispensing element 110. In some embodiments, the actuator dispenses fluid from only one insertable portion 107. In some embodiments, the actuator dispenses fluid from only one dispensing element 110. In some embodiments, dispensing the fluid 111 comprises propelling the fluid 111 out of the dispensing element 110 with compressed air. In some embodiments, the one or more dispensing elements 110 are contained with a secondary tubular member 324. In some embodiments, the reservoir is removable. In some embodiments, the reservoir is comprised within a removable cartridge. In some embodiments, the positioned trigger depresses a switch 104 underneath the positioning trigger to actuate the device.

In some embodiments, the device comprises a central tube fluidically connected to the one or more insertable portions 107, wherein the central tube is inserted into the reservoir when the device is actuated. In some embodiments, the device further comprises a central tube fluidically connected to the one or more dispensing elements 110, wherein the central tube is inserted into the reservoir when the device is actuated. In some embodiments, the device comprises a central tube fluidically connected to two insertable portions 107, wherein the central tube is inserted into the reservoir when the device is actuated. In some embodiments, the device comprising a central tube fluidically connected to two dispensing elements 110, wherein the central tube is inserted into the reservoir when the device is actuated. In some embodiments, the device further comprises a one or more bases connected to the bottom of the one or more dispensing elements 110 which move the one or more dispensing elements 110 upon actuation of the device.

Method

In one aspect, the disclosure provides a method for intranasal delivery to a subject with a device, the method comprising: positioning an insertable portion 107 of the device within an ejection zone 29 of a nasal cavity 11 of the subject by engaging a columella region 10 of the subject with a subject engaging portion 106 of the device, seating the insertable portion 107 within the ejection zone 29 of the subject's nasal cavity 11, wherein the ejection zone 29 is: 0 mm to 30 mm superior to a horizontal line 627 that intersects the anterior aspect of the internal nasal valve 13, and 0 mm to 20 mm anterior to an inclined line 620 that intersects the anterior aspect of the middle turbinate 15 and the posterior aspect of the vestibule 21, and one or more of the following: 0 mm to 40 mm inferior to a horizontal line 621 that is parallel to the inferior aspect of the olfactory cleft 23, 0 mm to 20 mm posterior to the internal nasal dorsum 622, 10 mm to 50 mm superior to a horizontal line 623 that intersects the inferior aspect of the columella 10, 0 mm to 30 mm superior to a horizontal line 624 that intersects the superior aspect of the inferior turbinate 16, 0 mm to 3 mm from the septum 24 or any combination thereof.

In one aspect, the disclosure provides a method for intranasal delivery to a subject with a device, the method comprising: inserting two insertable portions 107 into nasal channels 20 of the subject, wherein upon the inserting at least one of the insertable portion 107 engages tissue within the nasal channel 20 thereby opening or expanding an opening of an internal nasal valve 13 of the subject, thereby positioning at least one of the insertable portions 107 for delivery of a composition 111 to the subject.

In one aspect, the disclosure provides a method for intranasal delivery to a subject with a device, the method comprising: positioning an insertable portion 107 of the device within a nasal channel 20 of the subject; and transitioning the device from a first configuration 100 to a second configuration 200 by applying pressure about a longitudinal axis 610 of the device, thereby revealing a dispensing element 110 from the first insertable portion 107 and simultaneously actuating the device to deliver the composition 111 to the subject.

In one aspect, the disclosure provides a method for intranasal delivery of a composition 111 to a target region 19 of the nasal cavity 11 of a subject, the method comprising: inserting a dispensing element 110 into an ejection zone 29 of a nasal cavity 11, wherein the ejection zone 29 is: 0 mm to 30 mm superior to a horizontal line 627 that intersects the anterior aspect of the internal nasal valve 13, and 0 mm to 20 mm anterior to an inclined line 620 that intersects the anterior aspect of the middle turbinate 15 and the posterior aspect of the vestibule 21, and one or more of the following: 0 mm to 40 mm inferior to a horizontal line 621 that is parallel to the inferior aspect of the olfactory cleft 23, 0 mm to 20 mm posterior to the internal nasal dorsum 622, 10 mm to 50 mm superior to a horizontal line 623 that intersects the inferior aspect of the columella 10, 0 mm to 30 mm superior to a horizontal line 624 that intersects the superior aspect of the inferior turbinate 16, 0 mm to 3 mm from the septum 24 or any combination thereof, and dispensing the composition 111 from the dispensing element 110 to contact the target region 19 with the composition 111, wherein dispensing the composition 111 from the ejection zone 29: a) increases on target delivery of the composition 111 to the target region 19, b) decreases off target delivery of the composition 111 to the nasal cavity 11, or c) both.

In one aspect, the disclosure provides a method for intranasal delivery to a subject with a device, the method comprising: positioning an insertable portion 107 of the device within a nasal channel 20 of the subject by engaging a columella region 10 of the subject with a subject engaging portion 106 of the device, thereby limiting a depth of insertion of the insertable portion 107 into the subject's nasal channel 20 and aligning the insertable portion 107 within the nasal channel 20 of the subject.

In one aspect, this disclosure provides for a method for intranasal delivery to a subject with a device, the method comprising: inserting two insertable portions 107 into nasal channels 20 of the subject, wherein upon the inserting at least one of the insertable portion 107 opens or expands the internal nasal valve 13 by pushing the upper lateral cartilage 25 and surrounding tissue up and away 625 from the septum 24 of the subject thereby positioning at least one of the insertable portions 107 for delivery of the compound 111, e.g., drugs, small and large molecules, medicaments in liquid, or gas form, or a combination thereof to the subject.

In one aspect this disclosure provides, a method for intranasal delivery to a subject with a device, the method comprising: positioning an insertable portion 107 of the device within a nasal channel 20 of the subject; and transitioning the device from a first configuration 100 to a second configuration 200, thereby extending from or revealing from a dispensing element 110 from the first insertable portion 107.

In one aspect, the disclosure provides a method for intranasal delivery to a subject with a device, the method comprising: positioning a dispensing element 110 within an ejection zone 29 of a nasal cavity 11 of the subject; and dispensing a composition 111 from a side opening 2010 of the dispensing element 110.

The method can be used for targeted delivery to the middle turbinate 15.

The method can deliver at least a percentage of the composition 111 ejected from the side opening 2010 to the middle turbinate 15. The method can deliver at most a percentage of the composition 111 ejected from the side opening 2010 to the nasopharynx.

In some embodiments, the composition is a liquid composition.

The method can comprise ejecting the composition from the side opening at a velocity.

In some embodiments, positioning the dispensing element 110 within the ejection zone 29 comprises positioning an insertable portion 107 of the device within the ejection zone 29 by engaging a columella region 10 of the subject with a subject engaging portion 106 of the device. In some embodiments, positioning the insertable portion 107 of the device within the ejection zone 29 comprises inserting the insertable portion 107 at an insertion angle.

In some embodiments, the method further comprises actuating the device by applying pressure to the columella region 10 of the subject with the subject engaging portion 106 of the device. In some embodiments, the positioning the insertable portion 107 of the device comprises positioning two insertable portions 107 into two nasal channels 20 of the subject, thereby opening or expanding an opening of an internal nasal valve 13 of the subject. In some embodiments, the positioning the dispensing element 110 of the device comprises positioning two dispensing elements 110 of the device into a nasal channel 20 of the subject, wherein the two dispensing elements 110 reveal from the insertable portion 107. In some embodiments, the method further comprises transitioning the device from a first configuration 100 to a second configuration 200, wherein the dispensing element 110 reveals from the insertable portion 107 upon transition of the device from the first configuration 100 to the second configuration 200.

In some embodiments, the method further comprises positioning the insertable portions 107 into nasal channels 20 of the subject by engaging a columella region 10 of the subject with a subject engaging portion 106 of the device, thereby limiting a depth of insertion of the device into the subject's nasal channel 20 and aligning the insertable portions 107 within the nasal channel 20 of the subject. In some embodiments, the two insertable portions 107 comprise at least one dispensing element 110. In some embodiments, the at least one dispensing element 110 reveals outwards from at least one of the two insertable portions 107. In some embodiments, the inserting two insertable portions 107 advances the two insertable portions 107 along the internal nasal dorsum 622 and/or on along either side of the septum 24 until a columella 10 engaging region of the device contacts a columella 10 of the subject, preventing further insertion, and establishing a depth datum 617. In some embodiments, a dispensing port 126 is positioned at a targeted region or subregion in the nasal cavity 11. In some embodiments, the targeted region is the middle turbinate, inferior turbinate, superior turbinate, superior middle inferior meatuses, or combinations thereof.

In some embodiments, the inserting two insertable portions 107 uses the nasofrontal angle 614 as an angular reference to position the insertable portions 107 within the nasal channels 20. In some embodiments, a dispensing port 126 is positioned at a targeted region or subregion in the nasal cavity 20. In some embodiments, the inserting two insertable portions 107 advances the two insertable portions 107 along the internal nasal dorsum 622 until a columella engaging region 106 of the device contacts a columella 10 of the subject, preventing further insertion, and establishing a depth datum 617, and wherein the inserting two insertable portions 107. uses the nasofrontal angle 614 as an angular reference to position the insertable portions 107 within the nasal channels 20, thereby positioning the two insertable portions 107 within the nasal cavity 20 at known position.

In some embodiments, the inserting two insertable portions 107 comprises inserting the two insertable portions 107 past a nasal vestibule 21. In some embodiments, the inserting two insertable portions 107 comprises inserting the two insertable portions 107 along soft tissues of a interior dorsum wall 612 in an orientation parallel to the soft tissues. In some embodiments, the inserting two insertable portions 107 prevents rotation of the device about an axis parallel to the subject's height. In some embodiments, the inserting two insertable portions 107 creates a yaw angle on a reference coronal plane 608 relative to a y-axis of the device. In some embodiments, the inserting two insertable portions 107 creates a substantially unimpeded flow channel to the target region 19. In some embodiments, the inserting two insertable portions 107 creates a substantially unimpeded flow to a nasal turbinate. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the target region 19 is the olfactory region 23 and the middle meatus 30. In some embodiments, the target region 19 is the olfactory region 23 and the middle meatus 30, wherein the composition is dispensed to both regions simultaneously. In some embodiments, the target region 19 is the olfactory region 23 and the middle meatus 30, and other regions of the nasal anatomy. In some embodiments, the target region 19 is the olfactory region 23 and the middle meatus 30, and other regions of the nasal anatomy, wherein the composition is dispensed to all regions simultaneously.

Figure 9A:
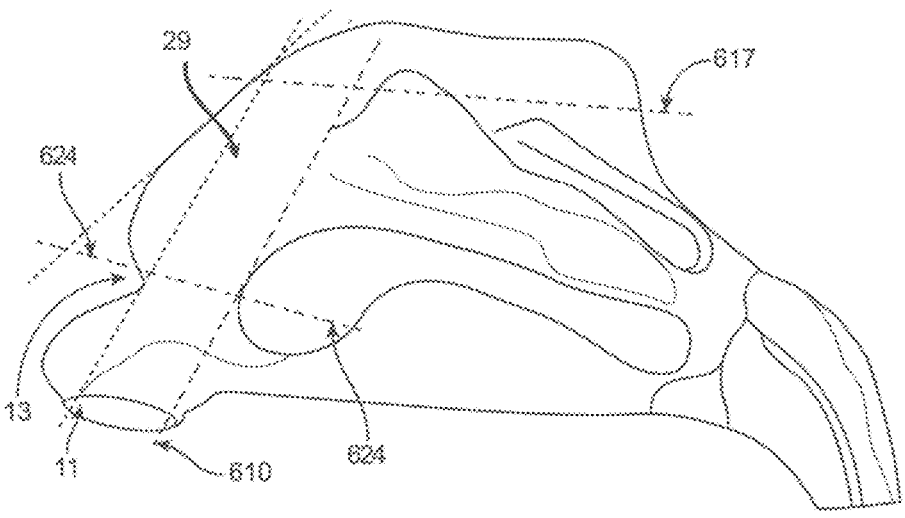
FIG. 9A depicts a side view of an ejection zone, according to some embodiments.

In some embodiments, the simultaneous actuation refers to transition for the first configuration 100 to the second configuration 200 and actuation occurring in a single motion upon application of pressure about a longitudinal axis 610 of the device. FIG. 9A depicts a side view of an exemplary embodiment of a representation subject's target ejection point.

The devices, systems and methods disclosed herein are advantageous over currently available intranasal delivery devices, in that the disclosed devices are well-matched for placement with respect to the internal nasal valve.

In some embodiments, the internal nasal valve is located approximately 10 mm-15 mm from the nostril opening, depending on individual variations. In some embodiments, the inferior (lower) aspect of the nasal valve, which is closer to the nostril, is towards the lower end of this range. In some embodiments, the superior (upper) aspect of the internal nasal valve is on average 2 cm-2.5 cm from the nostril opening.

The devices, systems and methods disclosed herein are advantageous over currently available intranasal delivery devices, in that the disclosed devices are configured for proper placement with respect to the nostril opening.

In some embodiments, the exemplary devices disclosed herein are designed to eject a composition within or above the nasal valve.

The devices, systems and methods disclosed herein are advantageous over currently available intranasal delivery devices, in that the disclosed devices comprise a vantage point well-matched for ejection in the patient nasal anatomy. In some embodiments, the device comprises an increased composition to target delivery due to the vantage point being within or above the internal nasal valve.

The devices, systems and methods disclosed herein are advantageous over currently available intranasal delivery devices, in that the disclosed devices comprise an ejection trajectory well-matched for patient nasal anatomy, wherein the device bypasses anatomical obstructions. In some embodiments, the device disclosed herein is configured so that part of the device can be inserted within the nasal valve (intra-internal), or above the level of the internal nasal valve (supra-internal). In some embodiments, the device positioning allows for an increased ejection trajectory. In some embodiments, the device positioning allows for a superior/anterior tendency. In some embodiments, the device positioning also allows for a direct anterior to an inferior/anterior formulation delivery-over stepping anatomical obstructions experienced by other devices.

In some embodiments, the ejection zone 29 is: 0 mm to 30 mm superior to a horizontal line 627 that intersects the anterior aspect of the internal nasal valve 13, and 0 mm to 20 mm anterior to an inclined line 620 that intersects the anterior aspect of the middle turbinate 15 and the posterior aspect of the vestibule 21, and one or more of the following: 0 mm to 40 mm inferior to a horizontal line 621 that is parallel to the inferior aspect of the olfactory cleft 23, 0 mm to 20 mm posterior to the internal nasal dorsum 622, 10 mm to 50 mm superior to a horizontal line that intersects the inferior aspect of the columella 623, 0 mm to 30 mm superior to a horizontal line 624 that intersects the superior aspect of the inferior turbinate 16, 0 mm to 3 mm from the septum 24, or any combination thereof. In some embodiments, the subject engaging portion 106 prevents movement of the distal end 128 within or away from the ejection zone 29 when the subject engaging portion 106 is seated on the columella region 10.

In some embodiments, dispensing a composition 111 from the ejection zone 29 increases on target deposition of the composition 111 to a turbinate, such as the middle turbinate 15. In some embodiments, the subject engaging portion 106 is seated on the columella region 10 when the subject engaging portion 106 simultaneously contacts a downward facing lateral face of the columella 10, a leftward facing lateral face of the columella 10, and a rightward facing lateral face of the columella 10. In some embodiments, the ejection zone 29 comprises a trapezium or irregular quadrilateral comprising (i) an inferior side 29A being a 10-25 mm horizontal line 627 extending posteriorly and horizontally from the anterior aspect of the internal nasal valve 13, (ii) an anterior side 29B being a 10-35 mm line extending superiorly and parallel to the internal nasal dorsum 622 from the anterior aspect of the internal nasal valve 13, (iii) a superior side 29C being a 10-25 mm line extending posteriorly and horizontally from a point on the internal nasal dorsum 622 that is 0-10 mm inferior to the inferior aspect of the olfactory cleft 23, and (iv) a posterior line 29D being a 10-35 mm line extending vertically along a plane that intersects the anterior aspect of the middle turbinate 15. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the target region 19 is the middle meatus 30, and wherein dispensing the composition 111 from a posterior end of the dispensing element 110 increases on target delivery of the composition 111 to the target region 19. In some embodiments, the ejection zone 29 is further: parallel with a middle turbinate 15 of the subject, and not within the middle meatus 30. In some embodiments, the target region 19 is one or both olfactory clefts 23, or a sub-area thereof. In some embodiments, the target region 19 is the olfactory region 23 and the middle meatus 30. In some embodiments, the target region 19 is the olfactory region 23 and the middle meatus 30, wherein the composition is dispensed to both regions simultaneously. In some embodiments, the target region 19 is the olfactory region 23 and the middle meatus 30, and other regions of the nasal anatomy. In some embodiments, the target region 19 is the olfactory region 23 and the middle meatus 30, and other regions of the nasal anatomy, wherein the composition 111 is dispensed to all regions simultaneously.

In one aspect, the disclosure provides a method for intranasal delivery to a subject with a device, the method comprising: positioning an insertable portion 107 of the device within a nasal channel 20 of the subject by engaging a columella region 10 of the subject with a subject engaging portion 106 of the device, thereby limiting a depth of insertion of the insertable portion 107 into the subject's nasal channel 20 and aligning the insertable portion 107 within the nasal channel 20 of the subject. In some embodiments, the method further comprises actuating the device by applying pressure to the columella region 10 of the subject with the subject engaging portion 106 of the device. In some embodiments, the positioning the insertable portion 107 of the device comprises positioning two insertable portions 107 into two nasal channels 20 of the subject, thereby opening or expanding the internal nasal valve 13 by pushing the upper lateral cartilage 25 and surrounding tissue up and away from the septum 24 of the subject thereby positioning the two insertable portions 107 for delivery of the compound 111, e.g., drugs, small and large molecules, medicaments in liquid or gas form, or a combination thereof to the subject. In some embodiments, the positioning the dispensing element 110 of the device comprises positioning at least one dispensing element 110 of the device into a nasal channel 20 of the subject, wherein the at least one dispensing element 110 reveal from the insertable portion 107. In some embodiments, the method further comprises transitioning the device from a first configuration 100 to a second configuration 200, wherein the dispensing element 110 reveals from the insertable portion 107 upon transition of the device from the first configuration 100 to the second configuration 200.

In one aspect, this disclosure provides for a method for intranasal delivery to a subject with a device, the method comprising: inserting two insertable portions 107 into nasal channels 20 of the subject, wherein upon the inserting at least one of the insertable portion 107 opens or expands the internal nasal valve 13 by pushing the upper lateral cartilage 25 and surrounding tissue up and away 625 from the septum 24 of the subject thereby positioning at least one of the insertable portions 107 for delivery of the compound 111, e.g., drugs, small and large molecules, medicaments in liquid or gas form, or a combination thereof to the subject. In some embodiments, the method further comprises positioning the insertable portions 107 into nasal channels 20 of the subject by engaging a columella region 10 of the subject with a subject engaging portion 106 of the device, thereby limiting a depth of insertion of the device into the subject's nasal channel 20 and aligning the insertable portions 107 within the nasal channel 20 of the subject. In some embodiments, the method further comprises actuating the device by applying pressure to the subject engaging portion 106 of the device with the columella region 10 of the subject. In some embodiments, the method comprises the two insertable portions 107, wherein the two insertable portions 107 comprise at least one dispensing element 110. In some embodiments, the method comprises the at least one dispensing element 110, wherein the at least one dispensing element 110 is configured to reveal outwards from the at least one of the two insertable portions 107. In some embodiments, the method further comprises transitioning the device from a first configuration 100 to a second configuration 200, wherein the dispensing element 110 reveals from the insertable portion 107 upon transition of the device from the first configuration 100 to the second configuration 200.

In one aspect this disclosure provides, a method for intranasal delivery to a subject with a device, the method comprising: positioning an insertable portion 107 of the device within a nasal channel 20 of the subject; and transitioning the device from a first configuration 100 to a second configuration 200, thereby extending from or revealing from a dispensing element 110 from the first insertable portion 107. In some embodiments, the method comprises the positioning the insertable portion 107 of the device within the nasal channel 20 of the subject occurs by engaging a columella region 10 of the subject with a subject engaging portion 106 of the device. In some embodiments, the method further comprises actuating the device by applying pressure to the subject engaging portion 106 of the device with the columella region 10 of the subject. In some embodiments, the method comprises positioning the insertable portion 107 of the device within the nasal channel 20 of the subject, wherein the insertable portion 107 opens or expands the internal nasal valve 13 by pushing the upper lateral cartilage 25 and surrounding tissue up and away 625 from the septum 24 of the subject thereby positioning at least one of the insertable portions 107 for delivery of the compound 111, e.g., drugs, small and large molecules, medicaments in liquid or gas form, or a combination thereof to the subject. In some embodiments, the method comprises two insertable portions 107, each for insertion into a nasal channel 20 of the subject.

In one aspect this disclosure provides, a method of using the columella 10 as an anchor to control insertion depth and angle, and to trigger the device.

In one aspect this disclosure provides, a method of using the columella 10 as a (fixed) reference as part of anthropometric calculation(s) to establish proper cannula length.

Referring to FIGS. 6A-6H. In some embodiments, the method further comprises creating a predictable/repeatable relationship of an inserter to subject anatomy. In some embodiments, the method further comprises the subject having a coronal plane 601, horizontal or axial or transverse plane 602, sagittal plane 603, medial plane 604, or parasagittal plane 605, or combination thereof. In some embodiments, the method further comprises creating a relative angular coordinate system of roll on the Y-axis of the device, pitch on the device sagittal plane 607, and yaw on the device coronal plane 608. In some embodiments, the method further comprises creating a subject linear coordinate system x relative to subject medial/lateral, y relative to subject superior/inferior, and z relative to subject anterior/posterior.

In some embodiments, the method further comprises positioning the insertable portions 107 along its y-axis in relation to other anatomy, creating a predictable/repeatable relationship with regards to the devices pitch angle on the subject's sagittal plane. In some embodiments, the method further comprises, from the devices predictable/repeatable relationship to other anatomy, the pitch angle can be related to known anthropometric data. In some embodiments, the method further comprises the insertable portions 107 configured to follow the shape of the interior dorsum wall 612, and lateral aspects of the septum 24 in the nasal cavity 11, allowing it to maintain a consistent and repeatable angle on the sagittal plane 603, wherein this positioning is achieved when the insertable portions 107 are inserted past the nasal vestibule 21 and into the nasal cavity 11. In some embodiments, the method further comprises the insertable portions 107 configured to hold it to, and guide it along the soft tissues of the interior dorsum wall 612, ensuring that it remains parallel to these tissues. In some embodiments, the method further comprises, as the tissues of the interior dorsum wall 612 are parallel to known anthropometric axis 613 drawn from nasion 619 to tip 128, used in both the nasofacial and nasofrontal angle 614, a known angler anthropometric range can be determined for the position of the inserter longitudinal axis 610 on the sagittal plane 603 relative to subject anatomy.

In some embodiments, the method further comprises the insertable portions 107 are designed to interlock with the nasal cavity 11. In some embodiments, the method further comprises the insertable portions 107 are designed to key medial to the lateral aspects of septal cartilage, and bilaterally to the greater alar and lateral nasal cartilage, including the connective tissues of these structures. In some embodiments, the method further comprises the insertable portions 107 locked in the y-axis rotation along the device 616, and locked in medially/laterally 609.

In some embodiments, the method further comprises the insertable portions 107 configured to position and interlock within the nasal cavity 11, creating a predictable/repeatable depth 618. In some embodiments, the method further comprises the insertable portions 107 configured to key and hard stop on the columella 10 its supporting structures, e.g., the nasal spine and septal cartilage. In some embodiments, the method further comprises, as the columella 10 comprises a depth datum 617 along the device y-axis, the ejection ports, e.g., the dispensing elements 110, of the insertable portions 107 may be placed at desired and known distance from a target anatomy.

In some embodiments, the method further comprises, with a known depth, Cartesian and angular reference of the insertable portions 107 relative to subject anatomies in the subject anatomy, exit ports, e.g., dispensing port(s) 126 along one or more dispensing elements 110, may be placed in a desired location to create a desired trajectory of the dose and a relative fluid profile and velocity may be chosen to deliver the composition to a desired location, e.g., target region 19, repeatably and accurately. In some embodiments, the method further comprises, a coherent jet may be formed along the z-axis of the device, creating a substantially unimpeded flow to the turbinates, e.g., superior turbinate 14, middle turbinate 15, or inferior turbinate 16, or a combination thereof.

In some embodiments, the ejection zone is superior to a horizontal line that intersects the anterior aspect of the internal nasal valve by about 1 mm to about 30 mm. In some embodiments, the ejection zone is superior to a horizontal line that intersects the anterior aspect of the internal nasal valve by about 1 mm to about 2 mm, about 1 mm to about 4 mm, about 1 mm to about 6 mm, about 1 mm to about 8 mm, about 1 mm to about 10 mm, about 1 mm to about 14 mm, about 1 mm to about 18 mm, about 1 mm to about 22 mm, about 1 mm to about 26 mm, about 1 mm to about 30 mm, about 2 mm to about 4 mm, about 2 mm to about 6 mm, about 2 mm to about 8 mm, about 2 mm to about 10 mm, about 2 mm to about 14 mm, about 2 mm to about 18 mm, about 2 mm to about 22 mm, about 2 mm to about 26 mm, about 2 mm to about 30 mm, about 4 mm to about 6 mm, about 4 mm to about 8 mm, about 4 mm to about 10 mm, about 4 mm to about 14 mm, about 4 mm to about 18 mm, about 4 mm to about 22 mm, about 4 mm to about 26 mm, about 4 mm to about 30 mm, about 6 mm to about 8 mm, about 6 mm to about 10 mm, about 6 mm to about 14 mm, about 6 mm to about 18 mm, about 6 mm to about 22 mm, about 6 mm to about 26 mm, about 6 mm to about 30 mm, about 8 mm to about 10 mm, about 8 mm to about 14 mm, about 8 mm to about 18 mm, about 8 mm to about 22 mm, about 8 mm to about 26 mm, about 8 mm to about 30 mm, about 10 mm to about 14 mm, about 10 mm to about 18 mm, about 10 mm to about 22 mm, about 10 mm to about 26 mm, about 10 mm to about 30 mm, about 14 mm to about 18 mm, about 14 mm to about 22 mm, about 14 mm to about 26 mm, about 14 mm to about 30 mm, about 18 mm to about 22 mm, about 18 mm to about 26 mm, about 18 mm to about 30 mm, about 22 mm to about 26 mm, about 22 mm to about 30 mm, or about 26 mm to about 30 mm, including increments therein.

In some embodiments, the ejection zone is superior to a horizontal line that intersects the anterior aspect of the internal nasal valve by about 1 mm, about 2 mm, about 4 mm, about 6 mm, about 8 mm, about 10 mm, about 14 mm, about 18 mm, about 22 mm, about 26 mm, or about 30 mm.

In some embodiments, the ejection zone is superior to a horizontal line that intersects the anterior aspect of the internal nasal valve by at least about 1 mm, about 2 mm, about 4 mm, about 6 mm, about 8 mm, about 10 mm, about 14 mm, about 18 mm, about 22 mm, or about 26 mm.

In some embodiments, the ejection zone is superior to a horizontal line that intersects the anterior aspect of the internal nasal valve by at most about 2 mm, about 4 mm, about 6 mm, about 8 mm, about 10 mm, about 14 mm, about 18 mm, about 22 mm, about 26 mm, or about 30 mm.

In some embodiments, the ejection zone is anterior to an inclined line that intersects the anterior aspect of the middle turbinate and the posterior aspect of the vestibule by about 1 mm to about 20 mm. In some embodiments, the ejection zone is anterior to an inclined line that intersects the anterior aspect of the middle turbinate and the posterior aspect of the vestibule by about 1 mm to about 2 mm, about 1 mm to about 4 mm, about 1 mm to about 6 mm, about 1 mm to about 8 mm, about 1 mm to about 10 mm, about 1 mm to about 12 mm, about 1 mm to about 14 mm, about 1 mm to about 16 mm, about 1 mm to about 18 mm, about 1 mm to about 20 mm, about 2 mm to about 4 mm, about 2 mm to about 6 mm, about 2 mm to about 8 mm, about 2 mm to about 10 mm, about 2 mm to about 12 mm, about 2 mm to about 14 mm, about 2 mm to about 16 mm, about 2 mm to about 18 mm, about 2 mm to about 20 mm, about 4 mm to about 6 mm, about 4 mm to about 8 mm, about 4 mm to about 10 mm, about 4 mm to about 12 mm, about 4 mm to about 14 mm, about 4 mm to about 16 mm, about 4 mm to about 18 mm, about 4 mm to about 20 mm, about 6 mm to about 8 mm, about 6 mm to about 10 mm, about 6 mm to about 12 mm, about 6 mm to about 14 mm, about 6 mm to about 16 mm, about 6 mm to about 18 mm, about 6 mm to about 20 mm, about 8 mm to about 10 mm, about 8 mm to about 12 mm, about 8 mm to about 14 mm, about 8 mm to about 16 mm, about 8 mm to about 18 mm, about 8 mm to about 20 mm, about 10 mm to about 12 mm, about 10 mm to about 14 mm, about 10 mm to about 16 mm, about 10 mm to about 18 mm, about 10 mm to about 20 mm, about 12 mm to about 14 mm, about 12 mm to about 16 mm, about 12 mm to about 18 mm, about 12 mm to about 20 mm, about 14 mm to about 16 mm, about 14 mm to about 18 mm, about 14 mm to about 20 mm, about 16 mm to about 18 mm, about 16 mm to about 20 mm, or about 18 mm to about 20 mm, including increments therein.

In some embodiments, the ejection zone is anterior to an inclined line that intersects the anterior aspect of the middle turbinate and the posterior aspect of the vestibule by about 1 mm, about 2 mm, about 4 mm, about 6 mm, about 8 mm, about 10 mm, about 12 mm, about 14 mm, about 16 mm, about 18 mm, or about 20 mm. In some embodiments, the ejection zone is anterior to an inclined line that intersects the anterior aspect of the middle turbinate and the posterior aspect of the vestibule by at least about 1 mm, about 2 mm, about 4 mm, about 6 mm, about 8 mm, about 10 mm, about 12 mm, about 14 mm, about 16 mm, or about 18 mm. In some embodiments, the ejection zone is anterior to an inclined line that intersects the anterior aspect of the middle turbinate and the posterior aspect of the vestibule by at most about 2 mm, about 4 mm, about 6 mm, about 8 mm, about 10 mm, about 12 mm, about 14 mm, about 16 mm, about 18 mm, or about 20 mm.

In some embodiments, the ejection zone is inferior to a horizontal line that is parallel to the inferior aspect of the olfactory cleft by about 1 mm to about 35 mm. In some embodiments, the ejection zone is inferior to a horizontal line that is parallel to the inferior aspect of the olfactory cleft by about 1 mm to about 2 mm, about 1 mm to about 3 mm, about 1 mm to about 4 mm, about 1 mm to about 5 mm, about 1 mm to about 12 mm, about 1 mm to about 15 mm, about 1 mm to about 18 mm, about 1 mm to about 21 mm, about 1 mm to about 25 mm, about 1 mm to about 30 mm, about 1 mm to about 35 mm, about 2 mm to about 3 mm, about 2 mm to about 4 mm, about 2 mm to about 5 mm, about 2 mm to about 12 mm, about 2 mm to about 15 mm, about 2 mm to about 18 mm, about 2 mm to about 21 mm, about 2 mm to about 25 mm, about 2 mm to about 30 mm, about 2 mm to about 35 mm, about 3 mm to about 4 mm, about 3 mm to about 5 mm, about 3 mm to about 12 mm, about 3 mm to about 15 mm, about 3 mm to about 18 mm, about 3 mm to about 21 mm, about 3 mm to about 25 mm, about 3 mm to about 30 mm, about 3 mm to about 35 mm, about 4 mm to about 5 mm, about 4 mm to about 12 mm, about 4 mm to about 15 mm, about 4 mm to about 18 mm, about 4 mm to about 21 mm, about 4 mm to about 25 mm, about 4 mm to about 30 mm, about 4 mm to about 35 mm, about 5 mm to about 12 mm, about 5 mm to about 15 mm, about 5 mm to about 18 mm, about 5 mm to about 21 mm, about 5 mm to about 25 mm, about 5 mm to about 30 mm, about 5 mm to about 35 mm, about 12 mm to about 15 mm, about 12 mm to about 18 mm, about 12 mm to about 21 mm, about 12 mm to about 25 mm, about 12 mm to about 30 mm, about 12 mm to about 35 mm, about 15 mm to about 18 mm, about 15 mm to about 21 mm, about 15 mm to about 25 mm, about 15 mm to about 30 mm, about 15 mm to about 35 mm, about 18 mm to about 21 mm, about 18 mm to about 25 mm, about 18 mm to about 30 mm, about 18 mm to about 35 mm, about 21 mm to about 25 mm, about 21 mm to about 30 mm, about 21 mm to about 35 mm, about 25 mm to about 30 mm, about 25 mm to about 35 mm, or about 30 mm to about 35 mm, including increments therein. In some embodiments, the ejection zone is inferior to a horizontal line that is parallel to the inferior aspect of the olfactory cleft by about 1 mm, about 2 mm, about 3 mm, about 4 mm, about 5 mm, about 12 mm, about 15 mm, about 18 mm, about 21 mm, about 25 mm, about 30 mm, or about 35 mm. In some embodiments, the ejection zone is inferior to a horizontal line that is parallel to the inferior aspect of the olfactory cleft by at least about 1 mm, about 2 mm, about 3 mm, about 4 mm, about 5 mm, about 12 mm, about 15 mm, about 18 mm, about 21 mm, about 25 mm, or about 30 mm. In some embodiments, the ejection zone is inferior to a horizontal line that is parallel to the inferior aspect of the olfactory cleft by at most about 2 mm, about 3 mm, about 4 mm, about 5 mm, about 12 mm, about 15 mm, about 18 mm, about 21 mm, about 25 mm, about 30 mm, or about 35 mm.

In some embodiments, the ejection zone is posterior to the internal nasal dorsum by about 1 mm to about 20 mm. In some embodiments, the ejection zone is posterior to the internal nasal dorsum by about 1 mm to about 2 mm, about 1 mm to about 3 mm, about 1 mm to about 4 mm, about 1 mm to about 6 mm, about 1 mm to about 8 mm, about 1 mm to about 10 mm, about 1 mm to about 12 mm, about 1 mm to about 14 mm, about 1 mm to about 16 mm, about 1 mm to about 18 mm, about 1 mm to about 20 mm, about 2 mm to about 3 mm, about 2 mm to about 4 mm, about 2 mm to about 6 mm, about 2 mm to about 8 mm, about 2 mm to about 10 mm, about 2 mm to about 12 mm, about 2 mm to about 14 mm, about 2 mm to about 16 mm, about 2 mm to about 18 mm, about 2 mm to about 20 mm, about 3 mm to about 4 mm, about 3 mm to about 6 mm, about 3 mm to about 8 mm, about 3 mm to about 10 mm, about 3 mm to about 12 mm, about 3 mm to about 14 mm, about 3 mm to about 16 mm, about 3 mm to about 18 mm, about 3 mm to about 20 mm, about 4 mm to about 6 mm, about 4 mm to about 8 mm, about 4 mm to about 10 mm, about 4 mm to about 12 mm, about 4 mm to about 14 mm, about 4 mm to about 16 mm, about 4 mm to about 18 mm, about 4 mm to about 20 mm, about 6 mm to about 8 mm, about 6 mm to about 10 mm, about 6 mm to about 12 mm, about 6 mm to about 14 mm, about 6 mm to about 16 mm, about 6 mm to about 18 mm, about 6 mm to about 20 mm, about 8 mm to about 10 mm, about 8 mm to about 12 mm, about 8 mm to about 14 mm, about 8 mm to about 16 mm, about 8 mm to about 18 mm, about 8 mm to about 20 mm, about 10 mm to about 12 mm, about 10 mm to about 14 mm, about 10 mm to about 16 mm, about 10 mm to about 18 mm, about 10 mm to about 20 mm, about 12 mm to about 14 mm, about 12 mm to about 16 mm, about 12 mm to about 18 mm, about 12 mm to about 20 mm, about 14 mm to about 16 mm, about 14 mm to about 18 mm, about 14 mm to about 20 mm, about 16 mm to about 18 mm, about 16 mm to about 20 mm, or about 18 mm to about 20 mm, including increments therein. In some embodiments, the ejection zone is posterior to the internal nasal dorsum by about 1 mm, about 2 mm, about 3 mm, about 4 mm, about 6 mm, about 8 mm, about 10 mm, about 12 mm, about 14 mm, about 16 mm, about 18 mm, or about 20 mm. In some embodiments, the ejection zone is posterior to the internal nasal dorsum by at least about 1 mm, about 2 mm, about 3 mm, about 4 mm, about 6 mm, about 8 mm, about 10 mm, about 12 mm, about 14 mm, about 16 mm, or about 18 mm. In some embodiments, the ejection zone is posterior to the internal nasal dorsum by at most about 2 mm, about 3 mm, about 4 mm, about 6 mm, about 8 mm, about 10 mm, about 12 mm, about 14 mm, about 16 mm, about 18 mm, or about 20 mm.

In some embodiments, the ejection zone is superior to a horizontal line that intersects the inferior aspect of the columella by about 10 mm to about 50 mm. In some embodiments, the ejection zone is superior to a horizontal line that intersects the inferior aspect of the columella by about 10 mm to about 12 mm, about 10 mm to about 16 mm, about 10 mm to about 20 mm, about 10 mm to about 24 mm, about 10 mm to about 28 mm, about 10 mm to about 32 mm, about 10 mm to about 36 mm, about 10 mm to about 40 mm, about 10 mm to about 45 mm, about 10 mm to about 50 mm, about 12 mm to about 16 mm, about 12 mm to about 20 mm, about 12 mm to about 24 mm, about 12 mm to about 28 mm, about 12 mm to about 32 mm, about 12 mm to about 36 mm, about 12 mm to about 40 mm, about 12 mm to about 45 mm, about 12 mm to about 50 mm, about 16 mm to about 20 mm, about 16 mm to about 24 mm, about 16 mm to about 28 mm, about 16 mm to about 32 mm, about 16 mm to about 36 mm, about 16 mm to about 40 mm, about 16 mm to about 45 mm, about 16 mm to about 50 mm, about 20 mm to about 24 mm, about 20 mm to about 28 mm, about 20 mm to about 32 mm, about 20 mm to about 36 mm, about 20 mm to about 40 mm, about 20 mm to about 45 mm, about 20 mm to about 50 mm, about 24 mm to about 28 mm, about 24 mm to about 32 mm, about 24 mm to about 36 mm, about 24 mm to about 40 mm, about 24 mm to about 45 mm, about 24 mm to about 50 mm, about 28 mm to about 32 mm, about 28 mm to about 36 mm, about 28 mm to about 40 mm, about 28 mm to about 45 mm, about 28 mm to about 50 mm, about 32 mm to about 36 mm, about 32 mm to about 40 mm, about 32 mm to about 45 mm, about 32 mm to about 50 mm, about 36 mm to about 40 mm, about 36 mm to about 45 mm, about 36 mm to about 50 mm, about 40 mm to about 45 mm, about 40 mm to about 50 mm, or about 45 mm to about 50 mm, including increments therein. In some embodiments, the ejection zone is superior to a horizontal line that intersects the inferior aspect of the columella by about 10 mm, about 12 mm, about 16 mm, about 20 mm, about 24 mm, about 28 mm, about 32 mm, about 36 mm, about 40 mm, about 45 mm, or about 50 mm. In some embodiments, the ejection zone is superior to a horizontal line that intersects the inferior aspect of the columella by at least about 10 mm, about 12 mm, about 16 mm, about 20 mm, about 24 mm, about 28 mm, about 32 mm, about 36 mm, about 40 mm, or about 45 mm. In some embodiments, the ejection zone is superior to a horizontal line that intersects the inferior aspect of the columella by at most about 12 mm, about 16 mm, about 20 mm, about 24 mm, about 28 mm, about 32 mm, about 36 mm, about 40 mm, about 45 mm, or about 50 mm.

In some embodiments, the ejection zone is superior to a horizontal line that intersects the superior aspect of the inferior turbinate by about 1 mm to about 30 mm. In some embodiments, the ejection zone is superior to a horizontal line that intersects the superior aspect of the inferior turbinate by about 1 mm to about 2 mm, about 1 mm to about 4 mm, about 1 mm to about 6 mm, about 1 mm to about 8 mm, about 1 mm to about 10 mm, about 1 mm to about 12 mm, about 1 mm to about 15 mm, about 1 mm to about 18 mm, about 1 mm to about 21 mm, about 1 mm to about 25 mm, about 1 mm to about 30 mm, about 2 mm to about 4 mm, about 2 mm to about 6 mm, about 2 mm to about 8 mm, about 2 mm to about 10 mm, about 2 mm to about 12 mm, about 2 mm to about 15 mm, about 2 mm to about 18 mm, about 2 mm to about 21 mm, about 2 mm to about 25 mm, about 2 mm to about 30 mm, about 4 mm to about 6 mm, about 4 mm to about 8 mm, about 4 mm to about 10 mm, about 4 mm to about 12 mm, about 4 mm to about 15 mm, about 4 mm to about 18 mm, about 4 mm to about 21 mm, about 4 mm to about 25 mm, about 4 mm to about 30 mm, about 6 mm to about 8 mm, about 6 mm to about 10 mm, about 6 mm to about 12 mm, about 6 mm to about 15 mm, about 6 mm to about 18 mm, about 6 mm to about 21 mm, about 6 mm to about 25 mm, about 6 mm to about 30 mm, about 8 mm to about 10 mm, about 8 mm to about 12 mm, about 8 mm to about 15 mm, about 8 mm to about 18 mm, about 8 mm to about 21 mm, about 8 mm to about 25 mm, about 8 mm to about 30 mm, about 10 mm to about 12 mm, about 10 mm to about 15 mm, about 10 mm to about 18 mm, about 10 mm to about 21 mm, about 10 mm to about 25 mm, about 10 mm to about 30 mm, about 12 mm to about 15 mm, about 12 mm to about 18 mm, about 12 mm to about 21 mm, about 12 mm to about 25 mm, about 12 mm to about 30 mm, about 15 mm to about 18 mm, about 15 mm to about 21 mm, about 15 mm to about 25 mm, about 15 mm to about 30 mm, about 18 mm to about 21 mm, about 18 mm to about 25 mm, about 18 mm to about 30 mm, about 21 mm to about 25 mm, about 21 mm to about 30 mm, or about 25 mm to about 30 mm, including increments therein. In some embodiments, the ejection zone is superior to a horizontal line that intersects the superior aspect of the inferior turbinate by about 1 mm, about 2 mm, about 4 mm, about 6 mm, about 8 mm, about 10 mm, about 12 mm, about 15 mm, about 18 mm, about 21 mm, about 25 mm, or about 30 mm. In some embodiments, the ejection zone is superior to a horizontal line that intersects the superior aspect of the inferior turbinate by at least about 1 mm, about 2 mm, about 4 mm, about 6 mm, about 8 mm, about 10 mm, about 12 mm, about 15 mm, about 18 mm, about 21 mm, or about 25 mm. In some embodiments, the ejection zone is superior to a horizontal line that intersects the superior aspect of the inferior turbinate by at most about 2 mm, about 4 mm, about 6 mm, about 8 mm, about 10 mm, about 12 mm, about 15 mm, about 18 mm, about 21 mm, about 25 mm, or about 30 mm.

In some embodiments, the ejection zone is away from the septum by about 0.1 mm to about 3 mm. In some embodiments, the ejection zone is away from the septum by about 0.1 mm to about 0.2 mm, about 0.1 mm to about 0.4 mm, about 0.1 mm to about 0.6 mm, about 0.1 mm to about 0.8 mm, about 0.1 mm to about 1 mm, about 0.1 mm to about 1.25 mm, about 0.1 mm to about 1.5 mm, about 0.1 mm to about 1.75 mm, about 0.1 mm to about 2 mm, about 0.1 mm to about 2.5 mm, about 0.1 mm to about 3 mm, about 0.2 mm to about 0.4 mm, about 0.2 mm to about 0.6 mm, about 0.2 mm to about 0.8 mm, about 0.2 mm to about 1 mm, about 0.2 mm to about 1.25 mm, about 0.2 mm to about 1.5 mm, about 0.2 mm to about 1.75 mm, about 0.2 mm to about 2 mm, about 0.2 mm to about 2.5 mm, about 0.2 mm to about 3 mm, about 0.4 mm to about 0.6 mm, about 0.4 mm to about 0.8 mm, about 0.4 mm to about 1 mm, about 0.4 mm to about 1.25 mm, about 0.4 mm to about 1.5 mm, about 0.4 mm to about 1.75 mm, about 0.4 mm to about 2 mm, about 0.4 mm to about 2.5 mm, about 0.4 mm to about 3 mm, about 0.6 mm to about 0.8 mm, about 0.6 mm to about 1 mm, about 0.6 mm to about 1.25 mm, about 0.6 mm to about 1.5 mm, about 0.6 mm to about 1.75 mm, about 0.6 mm to about 2 mm, about 0.6 mm to about 2.5 mm, about 0.6 mm to about 3 mm, about 0.8 mm to about 1 mm, about 0.8 mm to about 1.25 mm, about 0.8 mm to about 1.5 mm, about 0.8 mm to about 1.75 mm, about 0.8 mm to about 2 mm, about 0.8 mm to about 2.5 mm, about 0.8 mm to about 3 mm, about 1 mm to about 1.25 mm, about 1 mm to about 1.5 mm, about 1 mm to about 1.75 mm, about 1 mm to about 2 mm, about 1 mm to about 2.5 mm, about 1 mm to about 3 mm, about 1.25 mm to about 1.5 mm, about 1.25 mm to about 1.75 mm, about 1.25 mm to about 2 mm, about 1.25 mm to about 2.5 mm, about 1.25 mm to about 3 mm, about 1.5 mm to about 1.75 mm, about 1.5 mm to about 2 mm, about 1.5 mm to about 2.5 mm, about 1.5 mm to about 3 mm, about 1.75 mm to about 2 mm, about 1.75 mm to about 2.5 mm, about 1.75 mm to about 3 mm, about 2 mm to about 2.5 mm, about 2 mm to about 3 mm, or about 2.5 mm to about 3 mm, including increments therein. In some embodiments, the ejection zone is away from the septum by about 0.1 mm, about 0.2 mm, about 0.4 mm, about 0.6 mm, about 0.8 mm, about 1 mm, about 1.25 mm, about 1.5 mm, about 1.75 mm, about 2 mm, about 2.5 mm, or about 3 mm. In some embodiments, the ejection zone is away from the septum by at least about 0.1 mm, about 0.2 mm, about 0.4 mm, about 0.6 mm, about 0.8 mm, about 1 mm, about 1.25 mm, about 1.5 mm, about 1.75 mm, about 2 mm, or about 2.5 mm. In some embodiments, the ejection zone is away from the septum by at most about 0.2 mm, about 0.4 mm, about 0.6 mm, about 0.8 mm, about 1 mm, about 1.25 mm, about 1.5 mm, about 1.75 mm, about 2 mm, about 2.5 mm, or about 3 mm.

Definitions

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure can be described in the context of a single embodiment, the features can also be provided separately or in any suitable combination. Conversely, although the present disclosure can be described herein in the context of separate embodiments for clarity, the disclosure can also be implemented in a single embodiment.

Reference in the specification to "some embodiments," "an embodiment," "one embodiment" or "other embodiments" means that a feature, structure, or characteristic described in connection with the embodiments is included in at least some embodiments, but not necessarily all embodiments, of the present disclosure.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the disclosure, and vice versa. Furthermore, compositions of the disclosure can be used to achieve methods of the disclosure.

The term "about" or "approximately" as used herein when referring to a measurable value such as a parameter, an amount, a temporal duration, and the like, is meant to encompass variations of +/−10% or less from the specified value, insofar such variations are appropriate to perform in the present disclosure. It is to be understood that the value to which the modifier "about" or "approximately" refers is itself also specifically disclosed.

The "columella" is the firm tissue bridge that separates the nostrils at the base of the nose. The "columella" is the most anteroinferior portion of the nasal septum. The term "columella" or "columella region" is the subnasale, or an anterior *nasale* spine, or a combination thereof. The columella region may comprise a subnasale, or a combination thereof. The columella shape may be defined by an anterior nasal spine located posteriorly to the columella e.g., 1 cm.

The term "composition" or "compound" or "therapeutic" or "sampling compound" or "sampling fluid" is therapeutics, medicaments, drugs, small and large molecules, medicaments in liquid, powder, or gas form, or a combination thereof having a low, intermediate, or high viscosity.

The "introduction pathway" is, in sequence, the vestibule, the anterior aspect of the internal nasal valve, and the anterior aspect of the respiratory region-anterior of the turbinates.

The "internal nasal valve" (INV) is a space bounded medially by the dorsal septum 24 (or just septum), laterally by the caudal portion of the upper lateral cartilage, and inferiorly by the head of the inferior turbinate.

The term "nasal cavity" includes two nasal channels, each comprising a vestibule, respiratory region and olfactory cleft, and a nasopharynx.

The term "trigger" refers to the part of the device that actuates the ejection mechanism, which in turn (through a variety of possible mechanism designs), delivers a compound from the device.

The term "turbinates" refers to superior turbinate, middle turbinate, or inferior turbinate, or a combination thereof.

Nasal Cavity: This is the large, air-filled space behind the nose, where air passes on its way to the throat during inhalation.

Internal Nasal Valve: This is the narrowest part of the nasal airway, located just beyond the nostril. It's formed by the edge of the nasal septum, the upper lateral cartilage, and the floor of the nose. The internal nasal valve plays a critical role in regulating airflow through the nose. The area of interest is superior (above) to this structure.

Nasal Septum: This is the thin wall of bone and cartilage that separates the right and left nostrils. It forms the medial (towards the middle) boundary of the region of interest.

Lateral Nasal Wall: This is the side wall of the nasal cavity, which is opposite to the nasal septum. It's a complex structure that includes the turbinates (long, curled bones that protrude into the nasal cavity) and the meatuses (grooves or channels between the turbinates). The lateral nasal wall forms the lateral (towards the side) boundary of the region of interest.

Middle and Superior Meatuses: These are the spaces within the nasal cavity located between the turbinates. The middle meatus is located beneath the middle turbinate and above the inferior turbinate, and the superior meatus is located beneath the superior turbinate. The region of interest encompasses parts of these spaces.

Nostrils (External Nares): These are the two openings of the nose where air enters.

Nasal Vestibule: The nasal vestibule is the most anterior part of the nasal cavity, just inside the nostrils. It's the area of the nose that protrudes outside the face predominantly. This area is lined with skin and contains hair follicles, and it acts as the initial filtering and warming area for inhaled air before it moves deeper into the nasal cavity. The nasal vestibule extends posteriorly to the nasal valve, which is the narrowest part of the nasal airway and located just beyond the nostril.

Turbinates (Nasal Conchae): These are three pairs of bony projections (inferior, middle, and superior) covered in mucous membrane that protrude into the nasal cavity from the lateral walls. They increase the surface area of the nasal cavity, aiding in the warming, humidification, and filtration of inhaled air.

Olfactory Region: This is a small area located at the top of the nasal cavity, where the sense of smell is located.

EXAMPLES

The following illustrative examples are representative of embodiments, of the compositions and methods described herein and are not meant to be limiting in any way.

Example 1: Ejection Targeting the Middle Turbinate

FIGS. 12A-12I show images of an exemplary nasal cavity of a subject during pre-ejection, ejection and post-ejection of a composition with the exemplary device from various positions and angles at the middle turbinate.

The tests performed utilized a low-speed tunable actuator, 3D printed nasal cavity model, syringe filled with 200 μL and 1 cP viscosity, dispensing element (cannula), magnetic support structure for nasal cavity model, magnetic base for support structure, high-speed camera and flashlight.

The fluid was ejected from the dispensing element at a volumetric flow rate of 2.1 mL/s (1 cP). The low-speed tunable actuator was set up to eject and deliver fluid at 1.5 m/s into the middle turbinate of the nasal cavity model. The 3D printed nasal cavity model was mounted on the magnetic support structure and attached to the magnetic base. The syringe was loaded with 200 ul of the 1 cP fluid. The cannula and syringe were mounted to the low-speed tunable actuator to achieve desired velocity. Each ejection was recorded using the high-speed camera. The cannula was inserted into the nasal cavity model at a depth of 37.5 mm from the columella point and positioned to aim at the front side of the middle turbinate in the nasal cavity model. It was observed that the ejected fluid entered the middle turbinate region and flowed down. The angle of the cannula was changed to roughly 5 degrees posterior to the back side of the middle turbinate, then the fluid was ejected again using the same parameters. It was observed that the ejected fluid split when it hit the center bottom of the middle turbinate, where half of it went up to the olfactory region and the other half went inside the middle turbinate. The ejection test was repeated with the cannula angle changed roughly 5 degrees again. It was observed that the fluid landed at the back of the olfactory region.

Figure 12A:
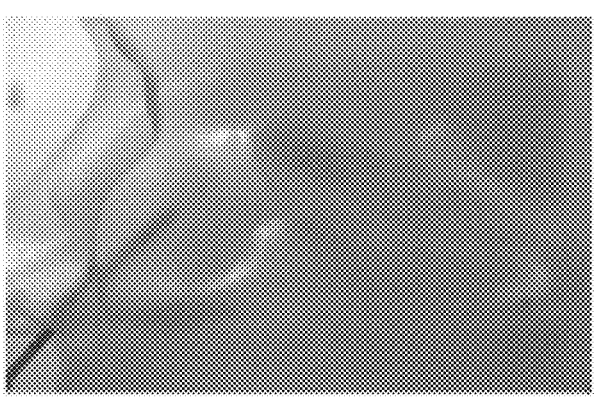
FIGS. 12A-12C, show images of an exemplary nasal cavity of a subject during pre-ejection (left), during ejection (middle) and post-ejection (right) of a composition with the exemplary device from a position where the ejected fluid is aimed at the front part of the middle turbinate, and illustrates that dispensing a composition from outside the ejection zone in this position prevents deposition of the composition to a target region.
Figure 12B:
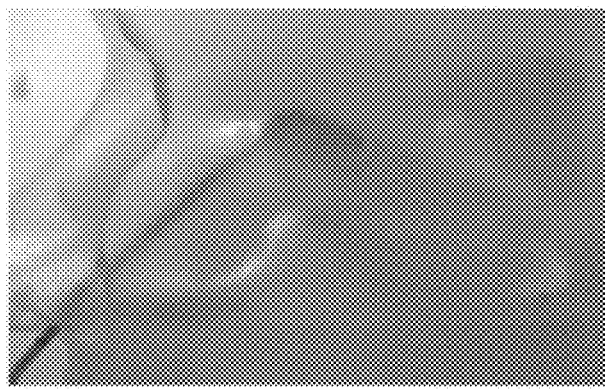
Figure 12C:
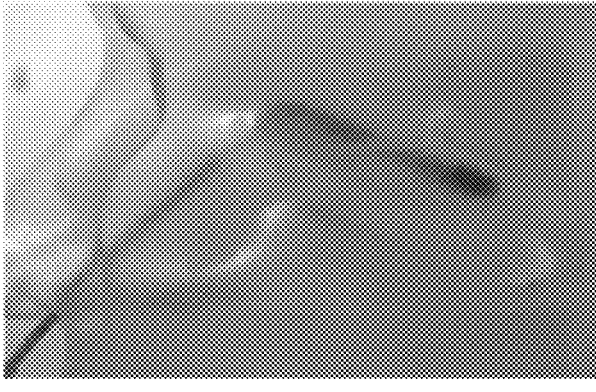

FIGS. 12A-12C, show images of an exemplary nasal cavity of a subject during pre-ejection (FIG. 12A), during ejection (FIG. 12B) and post-ejection (FIG. 12C) of a composition with the exemplary device from a position where the ejected fluid was aimed at the front part of the middle turbinate. The images show that no deposit of the composition was made in the olfactory cleft.

Figure 12D:
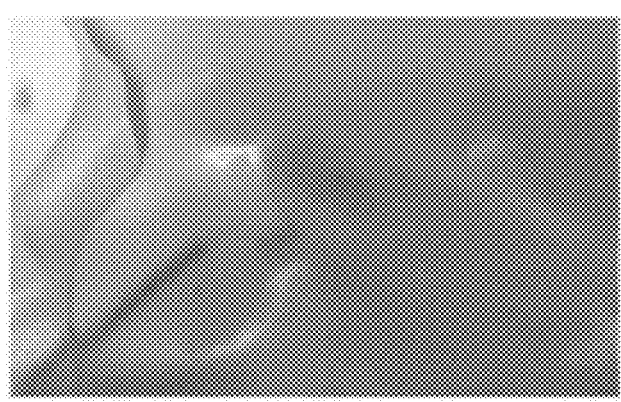
FIGS. 12D-12F, show images of an exemplary nasal cavity of a subject during pre-ejection (left), during ejection (middle) and post-ejection (right) of a composition with the exemplary device from a position where the angle is increased 10 degrees towards the posterior side, and illustrates that dispensing a composition from this position prevents deposition of the composition to a target region.
Figure 12E:
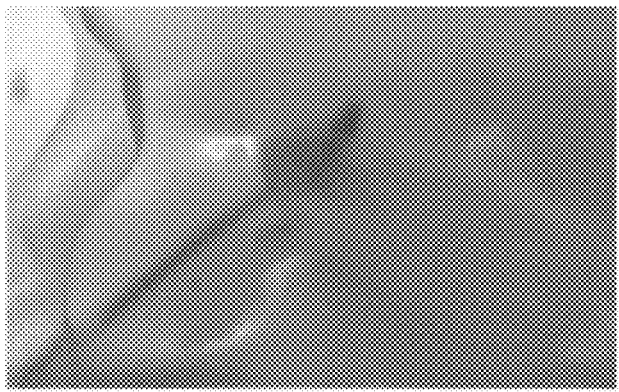
Figure 12F:
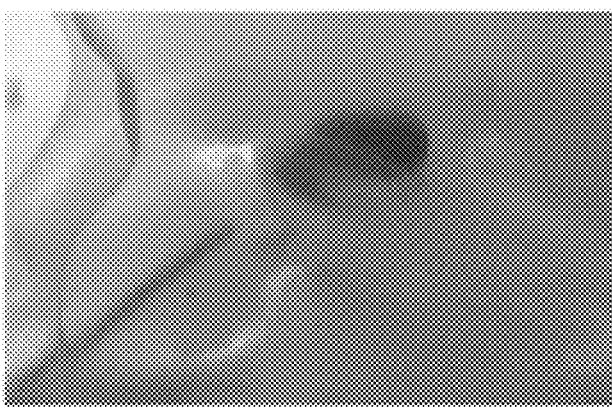

FIGS. 12D-12F, show images of an exemplary nasal cavity of a subject during pre-ejection (FIG. 12D), during ejection (FIG. 12E) and post-ejection (FIG. 12F) of a composition with the exemplary device from a position where the angle was increased 10 degrees towards the posterior side. The dispensing element comprised a composition volume of 200 μL and 1 cP viscosity. The composition was ejected from the dispensing element at a velocity of 2 m/s (1 cP). The images show that about one half of the composition was deposited in the olfactory cleft, however, in the olfactory cleft's lower aspect (not against the cribriform plate).

Figure 12G:
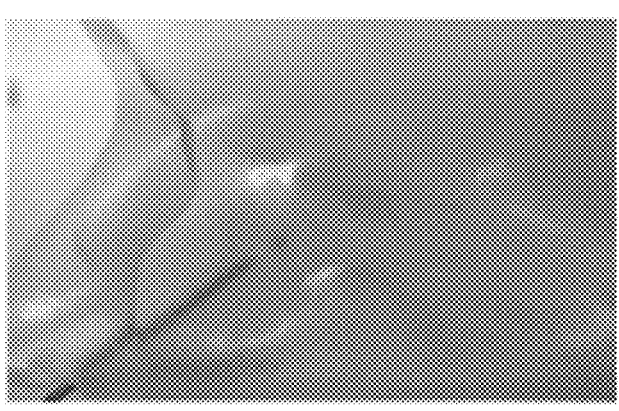
FIGS. 12G-12I, show images of an exemplary nasal cavity of a subject during pre-ejection (left), during ejection (middle) and post-ejection (right) of a composition with the exemplary device from a position where the angle is increased 20 degrees towards the posterior side, and illustrates that dispensing a composition from outside the ejection zone in this position prevents deposition of the composition to a target region.
Figure 12H:
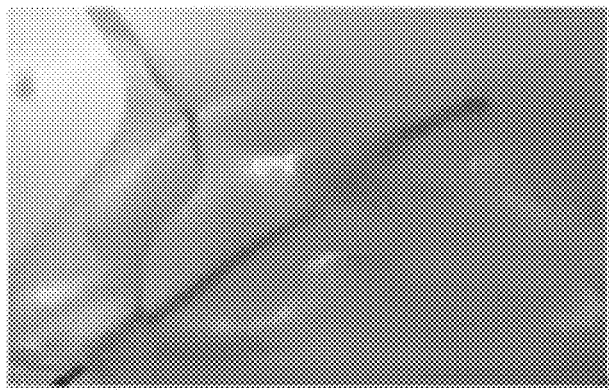
Figure 12I:
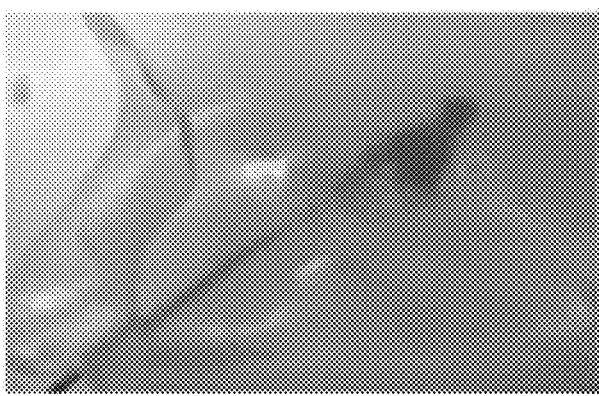
Figure 13A:
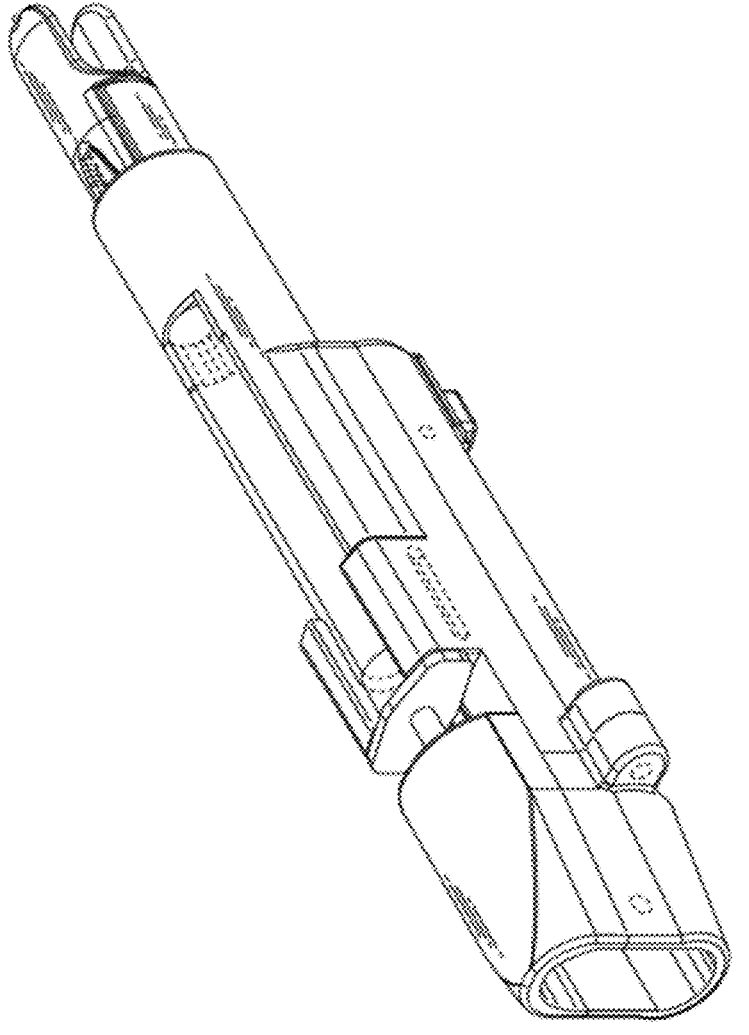
FIG. 13A shows a perspective view of an exemplary intranasal delivery device, showing an ornamental design.
Figures 13B, 13C:
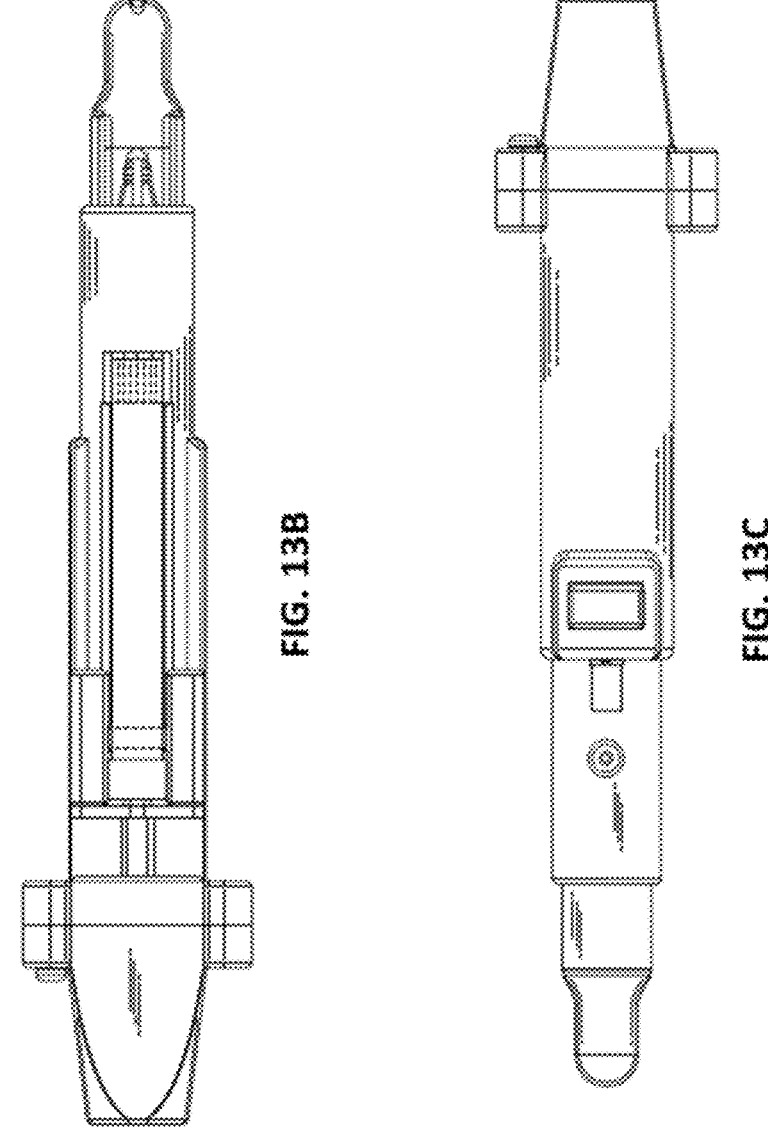
FIG. 13B shows a side view of an exemplary intranasal delivery device, showing an ornamental design.
FIG. 13C shows a side view of an exemplary intranasal delivery device, showing an ornamental design.
Figure 13D:
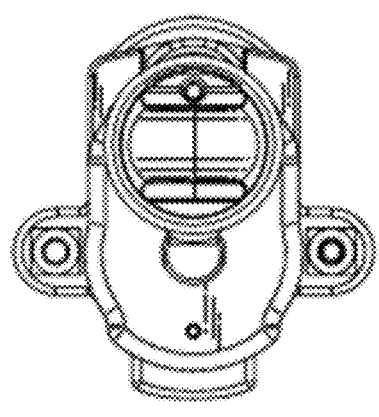
FIG. 13D shows a top view of an exemplary intranasal delivery device, showing an ornamental design.
Figure 13E:
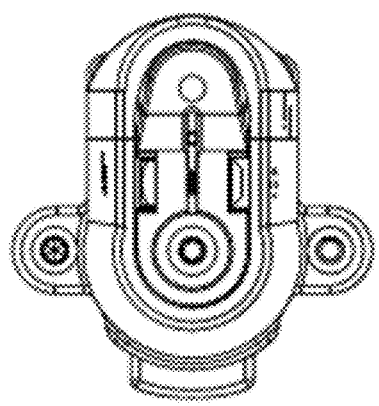
FIG. 13E shows a bottom view of an exemplary intranasal delivery device, showing an ornamental design.
Figure 13F:
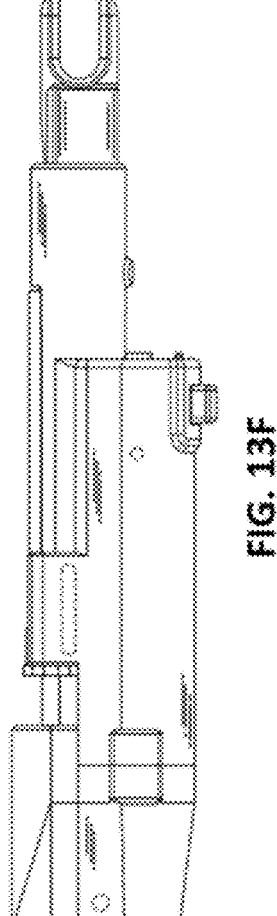
FIG. 13F shows a front view of an exemplary intranasal delivery device, showing an ornamental design.
Figure 13G:
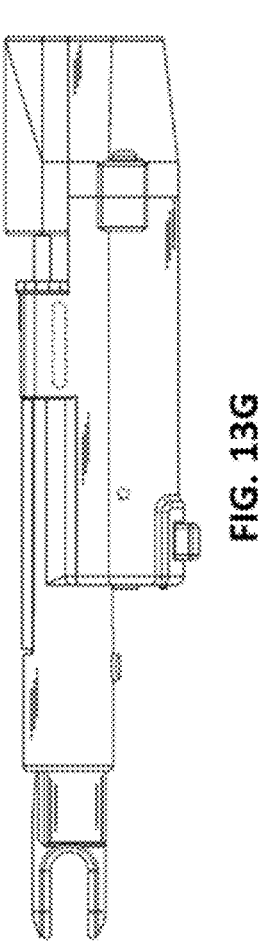
FIG. 13G shows a back view of an exemplary intranasal delivery device, showing an ornamental design.
Figure 14A:
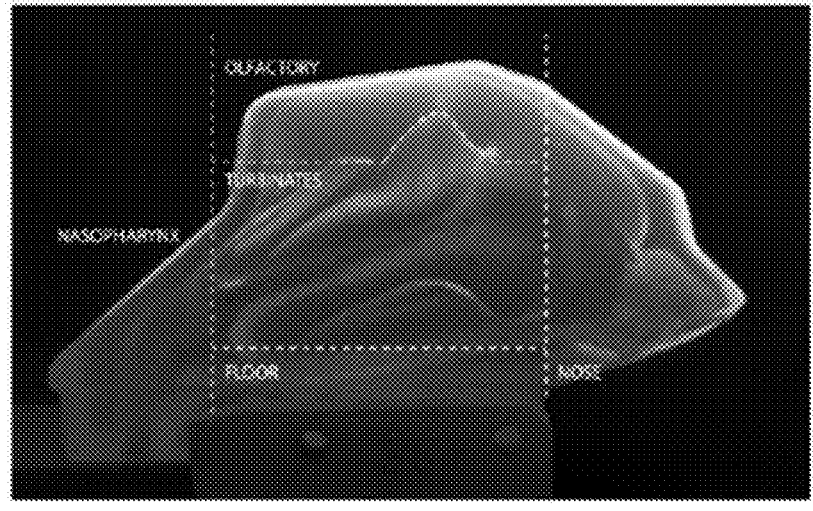
FIG. 14A depicts an illustration of the nasal cavity with deposition regions including the olfactory region, the turbinates, the nasal floor, and the nasopharynx. Deposition may target any region, subregion, or combination thereof. For example, deposition may target the turbinates only, the turbinates and the nasopharynx together, or the nasopharynx only.
Figure 14B:
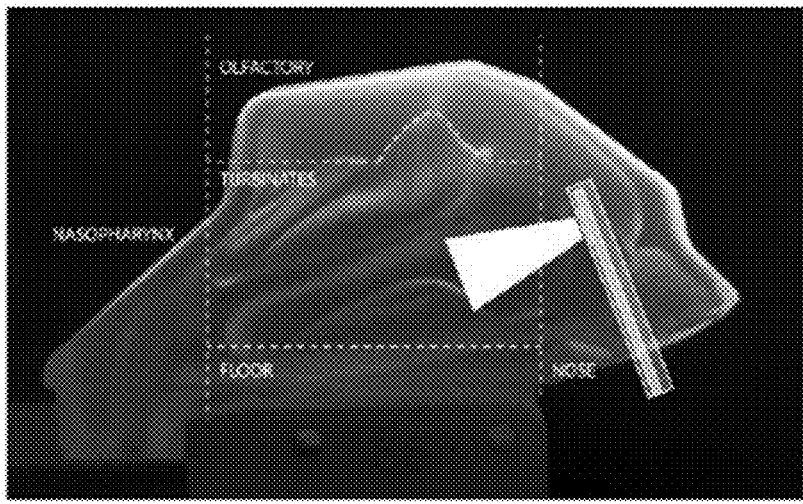
FIG. 14B depicts an illustration of an off-axis deposition trajectory from cannula dispensing from a vantage point above the nasal valve. Dispensing from above the nasal valve enables ejection trajectories which are unachievable from below the nasal valve. Devices described herein provide the ability to fire off-axis from the central device axis and dispense fluid at an angle past the nasal valve, thereby enabling beneficial deposition profiles targeting various regions of the lower nasal cavity.
Figure 17:
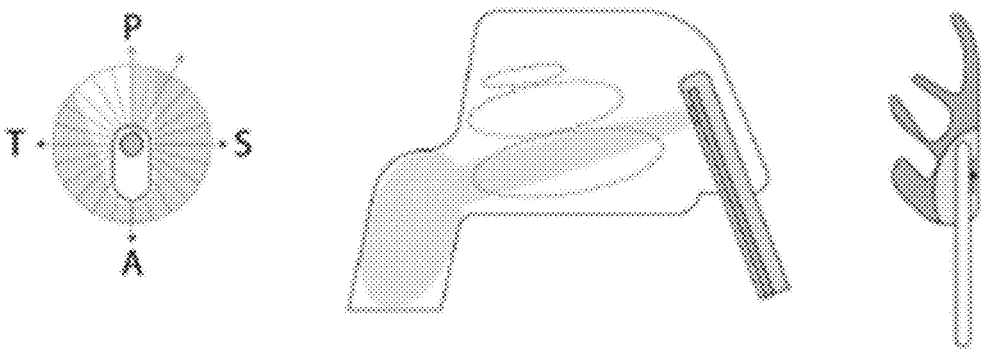
FIG. 17 depicts schematic illustrations of an example of nasopharynx deposition. A lateral ejection port is cut in a septal side of a cannula from about 0 to 30 degrees. The length of the cut is about 1 to 5 mm. The fluid velocity is about 0.5 to 6 m/s. The position of the ejection port is about 30 mm from the columella. The deposition type is bolus or surfacer. The impingement type is one which runs the septum with late formation/distribution.
Figure 18:
FIG. 18 depicts a photograph of an off-axis deposition example in a nasal cast.
Figure 19A:
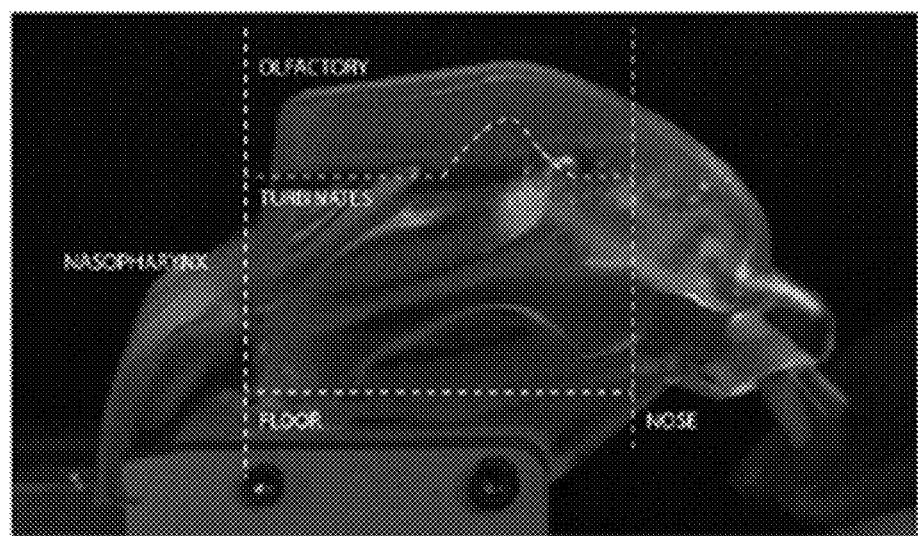
FIG. 19A depicts a still image of a spray deposition in a nasal cast.
Figure 19B:
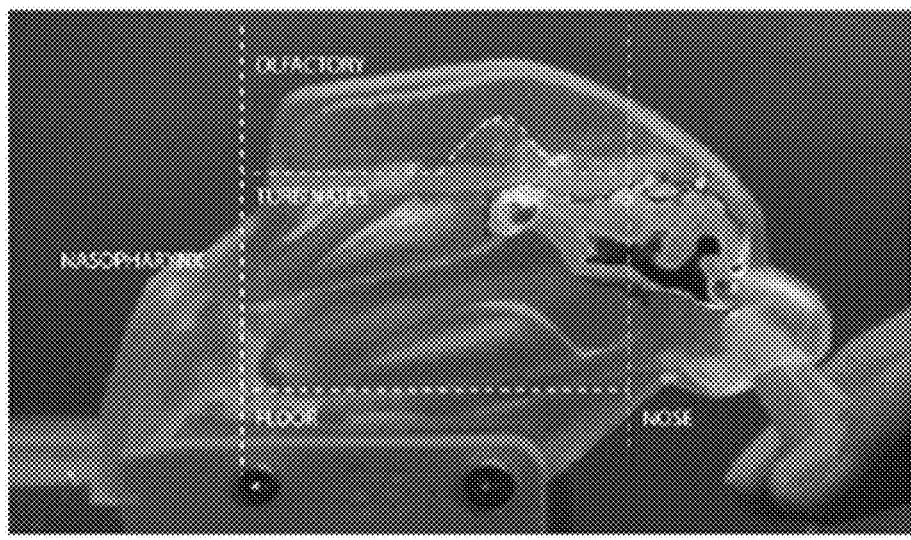
FIG. 19B depicts an image analysis of the spray deposition in a nasal cast shown in FIG. 19A.
Figure 20A:
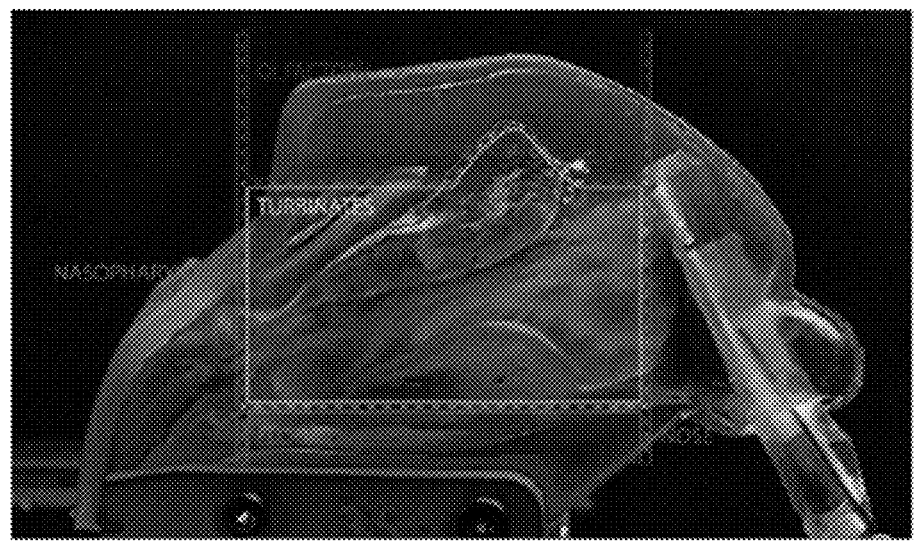
FIG. 20A depicts a still image of an example deposition having a turbinate only target region. The example deposition was via an example device of the present invention.
Figure 20B:
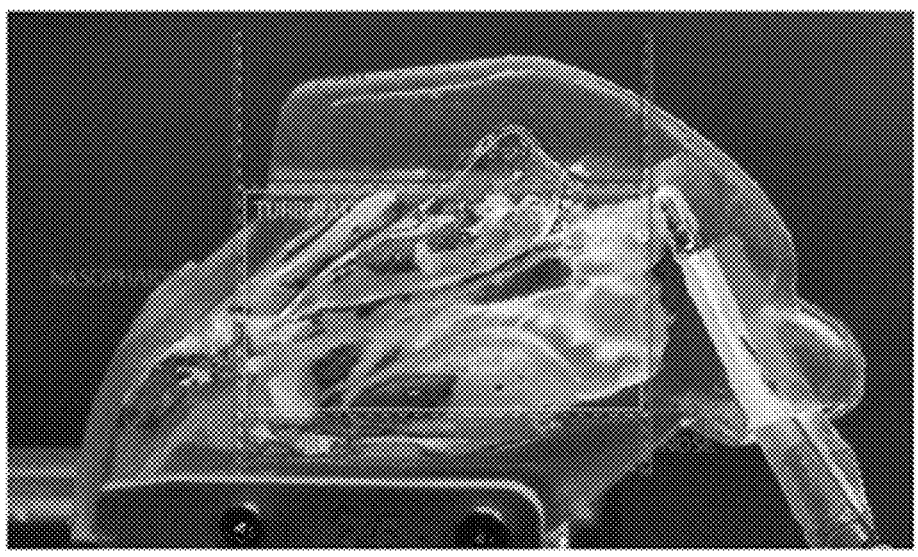
FIG. 20B depicts an image analysis of the turbinate only deposition in a nasal cast shown in FIG. 20A.
Figure 21A:
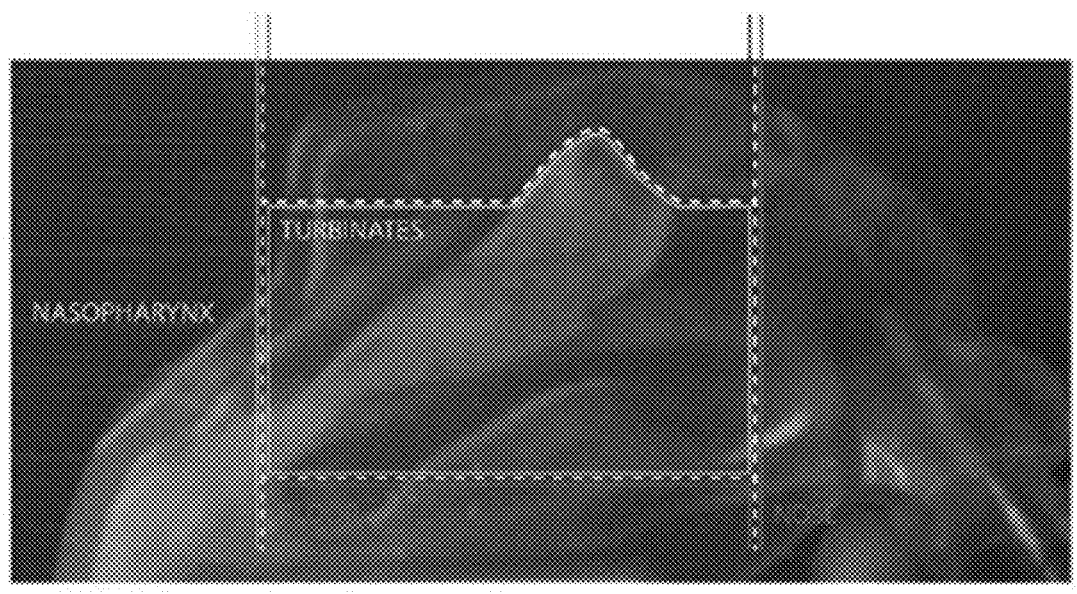
FIG. 21A depicts a still image of an example deposition having a turbinate/nasopharynx target region. The example deposition was via an example device of the present invention.
Figure 21B:
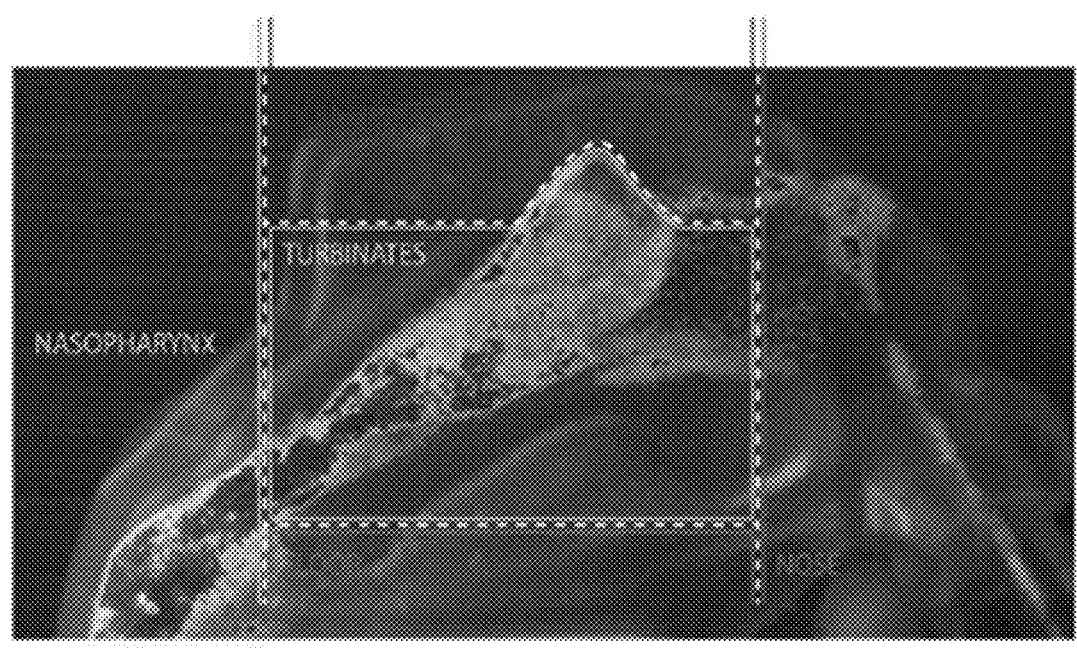
FIG. 21B depicts an image analysis of the turbinate/nasopharynx target deposition in a nasal cast shown in FIG. 21A.
Figure 22A:
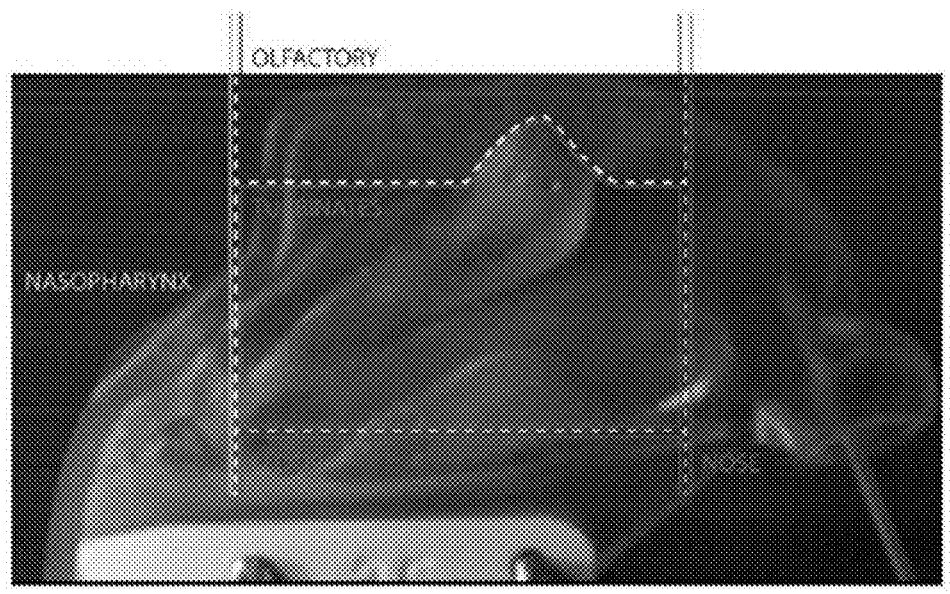
FIG. 22A depicts a still image of example deposition having a nasopharynx target region. The example deposition was via an example device of the present invention.
Figure 22B:
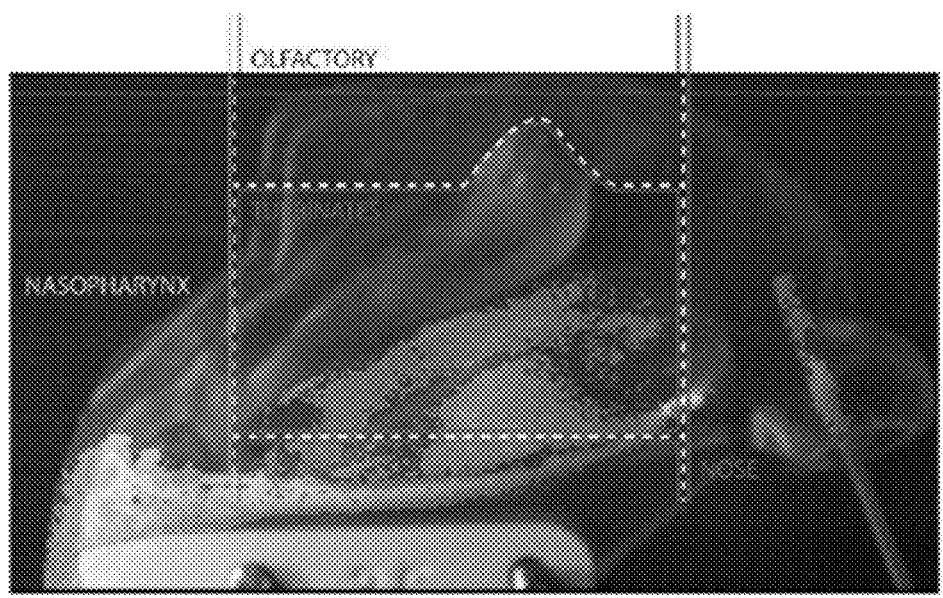
FIG. 22B depicts an image analysis of the nasopharynx target deposition in a nasal cast shown in FIG. 22A.

FIGS. 12G-12I, show images of an exemplary nasal cavity of a subject during pre-ejection (left), during ejection (middle) and post-ejection (right) of a composition with the exemplary device from a position where the angle was increased 20 degrees towards the posterior side. The dispensing element comprised a composition volume of 200 uL and 1 cP viscosity. The composition was ejected from the dispensing element at a velocity of 2 m/s (1 cP). The images show that most of the composition was deposited in the olfactory cleft, however, mostly in the back of the olfactory cleft and only a small portion against the cribriform plate.

By going from anterior to posterior angles, FIGS. 12A-12C illustrate that the fluid did not deposit in the olfactory cleft, FIGS. 12D-12F illustrate that about half the fluid deposited in the olfactory cleft, but in its lower aspect (not against the cribriform plate), and FIGS. 12G-12I illustrate that most of the fluid deposited in the olfactory cleft, but only in the back of the olfactory cleft and only a small portion against the cribriform plate.

Example 2: Device Position with Respect to Target Patient Anatomy

In some embodiments, the position where the proximal tip of exemplary devices disclosed herein is designed to be within the nasal vestibule, and any placement of ejection port on the device including extendable ports such as a cannula, is described below relative to patient anatomy.

Figure 9B:
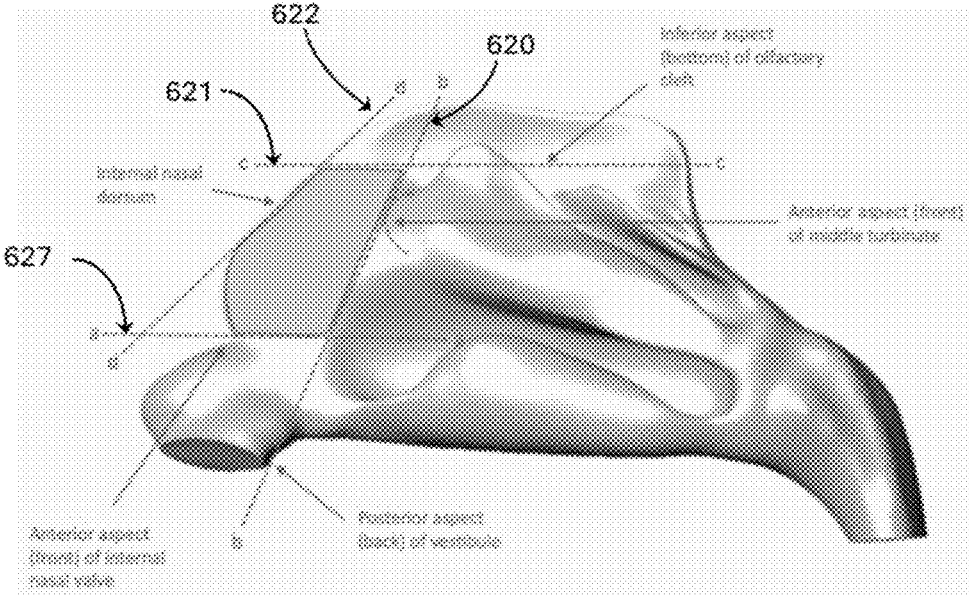
FIG. 9B depicts a side view of an ejection zone with respect to other nasal cavity anatomy, according to some embodiments.

FIG. 9B depicts a side view of an ejection zone with respect to other nasal cavity anatomy. In some embodiments, the nasal anatomy outlined herein creates a boundary region plane for the ejection zone. In some embodiments, the device tips may be present in all or a portion of the boundary regions.

In some embodiments, the superior boundary of exemplary devices disclosed herein is designed to be within the nasal vestibule and is bounded by the inferior aspect of the olfactory cleft, as depicted in plane c-c. In some embodiments, the superior boundary and depth guide is achieved by utilizing the structures of the columella as a datum or hard stop coming in contact with the columella saddle and choosing a specific length of the device tip relative to anthropometric variables.

In some embodiments, the inferior boundary of exemplary devices disclosed herein is designed to be positioned within the nasal vestibule, either intra-internal nasal valve (within), or supra-internal nasal valve (above the level of the internal nasal valve), as depicted in plane a-a. In some embodiments, the inferior boundary and depth guide is achieved by utilizing the structures of the columella as a datum or hard stop, and choosing specific lengths of the device tip relative to anthropometric variables.

In some embodiments, the anterior boundary of exemplary devices disclosed herein is designed to be positioned within the nasal vestibule, and is bounded by the internal dorsum of the nasal cavity, as depicted in plane d-d. In some embodiments, the anterior boundary is achieved by utilizing the ridge/trough-like structures of the internal dorsum as a hard stop and trajectory guide and having a corresponding edge design on the device tips that follow and is bounded by this anatomy. In some embodiments, the edge design on the device tips that follows and is bounded by the internal dorsum may be used as a known offset for positioning ejection ports.

In some embodiments, the medial boundary of exemplary devices disclosed herein is designed to be positioned within the nasal vestibule, lateral of the nasal septum, and is bounded by the thin wall of bone, cartilage, and mucosa that separates the right and left nostrils. In some embodiments, the medial boundary forms the medial (towards the middle) boundary of the region of interest. In some embodiments, the medial boundary is achieved by utilizing the structures of the septum as a hard stop and trajectory guide and has a corresponding internal face design on the device tips that follows and is bounded by this anatomy.

In some embodiments, the lateral boundary of exemplary devices disclosed herein is designed to be positioned within the nasal vestibule, medial of the soft tissue of the lateral internal nasal wall. In some embodiments, the lateral boundary is achieved by utilizing the structures of the lateral internal nasal wall as a hard stop and trajectory guide and has a corresponding external face design on the device tips that follows and is bounded by this anatomy.

In some embodiments, the angular position of exemplary devices disclosed herein is achieved by utilizing the corresponding edge design on the device tips as a trajectory guide that follows and is bounded by the internal nasal dorsum, as described in the anterior boundary. In some embodiments, the angular position may also be aided by the inferior, posterior, medial, and lateral boundaries and the corresponding design features of the device tips as described above.

Example 3: Device Position with Respect to Patient Nasal Anatomy

The devices, systems and methods disclosed herein are advantageous over currently available intranasal delivery devices, in that the disclosed devices are configured for placement with respect to the internal nasal valve.

In some embodiments, the internal nasal valve is located approximately 10 mm-15 mm from the nostril opening, depending on individual variations. In some embodiments, the inferior (lower) aspect of the nasal valve, which is closer to the nostril, is towards the lower end of this range. In some embodiments, the superior (upper) aspect of the internal nasal valve is on average 2 cm-2.5 cm from the nostril opening.

The devices, systems and methods disclosed herein are advantageous over currently available intranasal delivery devices, in that the disclosed devices are configured for placement with respect to the nostril opening.

In some embodiments, upon insertion, a distal end of an insertable portion of the exemplary devices disclosed herein are configured to locate more than 10 mm-15 mm from the nostril opening.

In some embodiments, upon insertion, a distal end of an insertable portion of the exemplary devices disclosed herein are configured to be within or above the nasal valve.

The devices, systems and methods disclosed herein are advantageous over currently available intranasal delivery devices, in that the disclosed devices comprise a vantage point well-matched for ejection in the patient nasal anatomy. In some embodiments, the device comprises an increased composition to target delivery due to the vantage point being within or above the internal nasal valve.

The devices, systems and methods disclosed herein are advantageous over currently available intranasal delivery devices, in that the disclosed devices are configured to eject a composition with an ejection trajectory well-matched for patient nasal anatomy, wherein the device bypasses anatomical obstructions in some embodiments, exemplary devices disclosed herein are located intra-internal nasal valve (within), or supra-internal nasal valve (above the level of the internal nasal valve). In some embodiments, the device positioning allows for an increased ejection trajectory. In some embodiments, the device positioning allows for a superior/anterior tendency. In some embodiments, the device positioning also allows for a direct anterior to an inferior/anterior formulation delivery-over stepping anatomical obstructions experienced by other devices.

Example 4: Intranasal Delivery with Cannula with a Slit Opening—Experimental Plan The performance of various cannula designs for fluid deposition in nasal models on the bench was evaluated. Studies were performed to: (1) Assess the impact of variables (e.g., viscosity, velocity, slit cut geometry) on fluid spread and targeting; (2) Quantify fluid distribution across specific regions of a nasal cavity model using a sectional nasal model; and (3) Adjust cannula designs to maximize middle turbinate deposition and minimize off-target deposition.

Figure 23A:
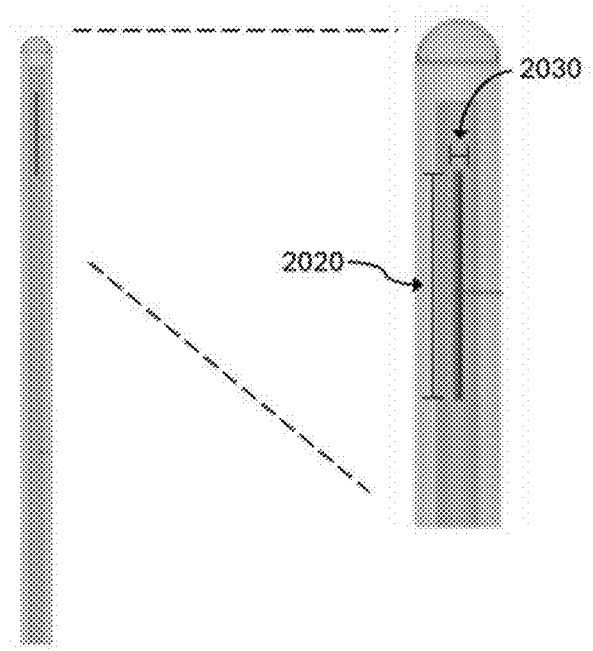
FIGS. 23A-23B depict cannula designs with a side opening according to some embodiments.
Figure 23B:
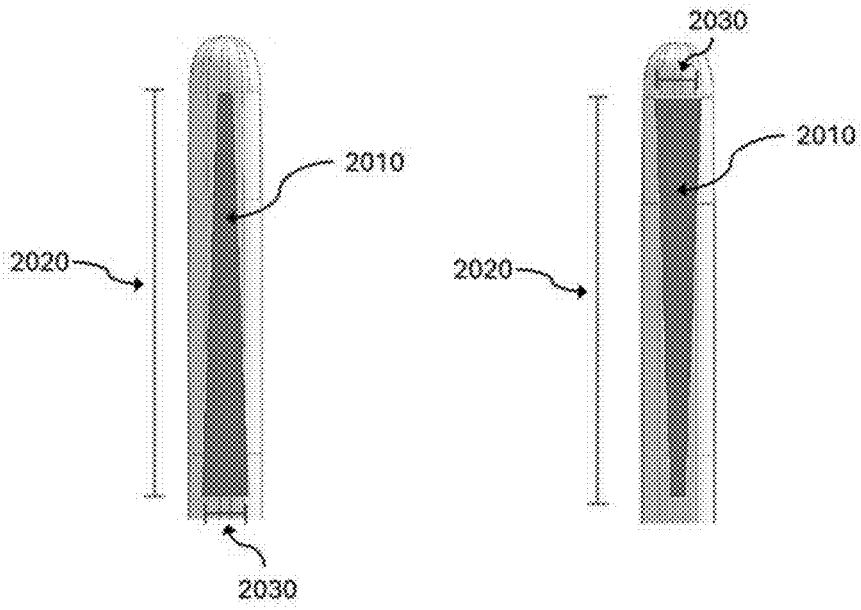
Figure 24A:
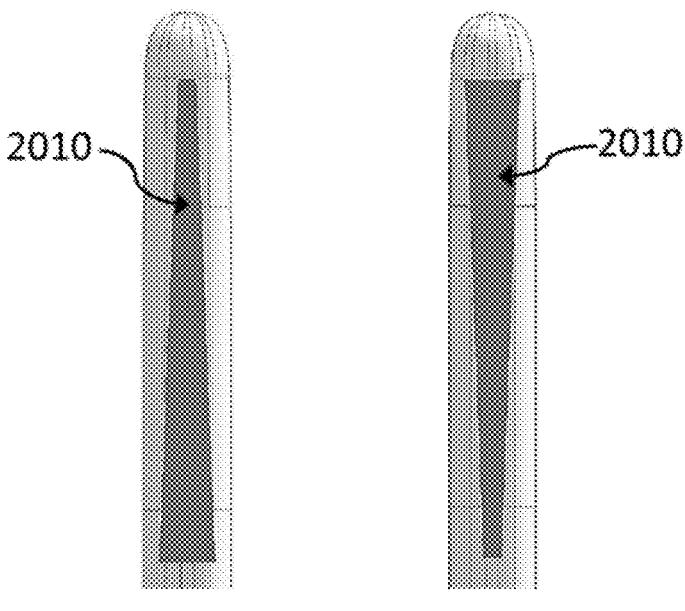
FIGS. 24A-24D depict various shapes of a side opening according to some embodiments.
Figure 24B:
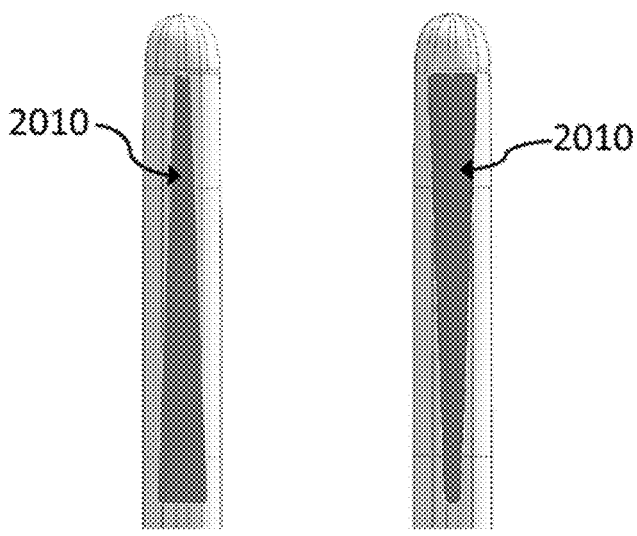
Figures 24C, 24D:
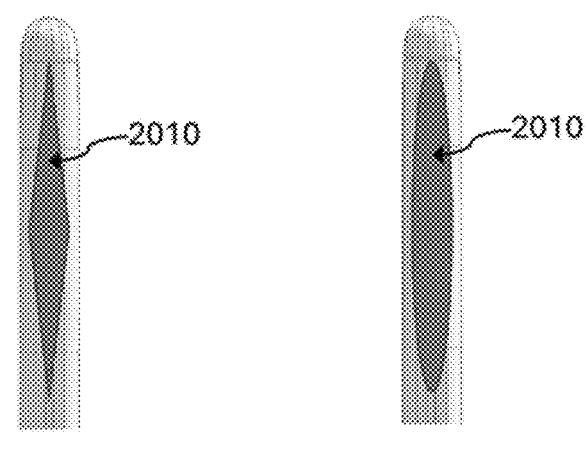

Study Parameters Included:
    (1) Cannula Design Variations (FIGS. 23A-23B):
        (i) Slit lengths: 3 mm, 6 mm, 9 mm, 12 mm.
        (ii) Slit widths: 0.3 mm, 0.5 mm, 0.75 mm, 1 mm, 1.3 mm.
        (iii) Offset angles: 0° and 20°.
    (2) Two viscosities were tested: 1 cP (baseline) and 20 cP (higher viscosity).
    (3) Insertion depths 20 mm and 32.5 mm.
    (4) Volumetric flow rates: 7.2 ml/s, 8.6 ml/s, 10 ml/s.

Figure 27:
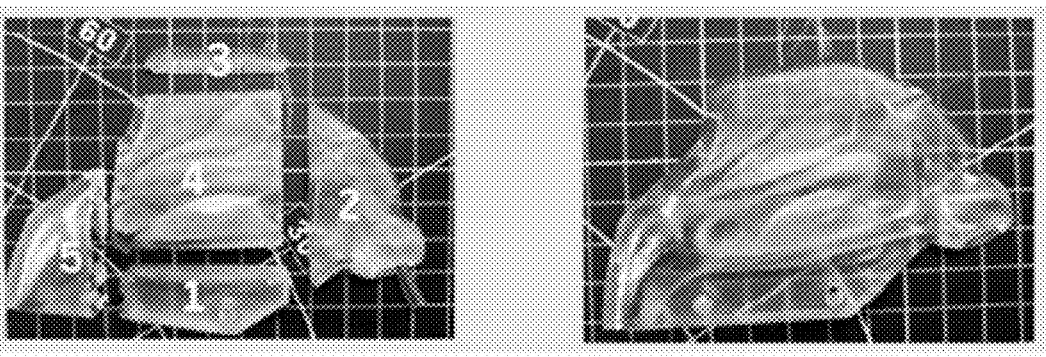
FIG. 27 depicts an average nasal model. The left panel depicts a sectional model and the right panel depicts a normal model according to some embodiments.

Study materials: Average nasal model—Sectional and Non-sectional (with secondary camera insert) (FIG. 27).

Bench Test Setup for:
    (i) Open-space ejection testing for visual assessments (side and front views).
    (ii) Sensitivity testing for insertion angles (30° and) 40°.
    (iii) Quantitative assessments using a sectioned nasal cavity model.

Figure 28A:
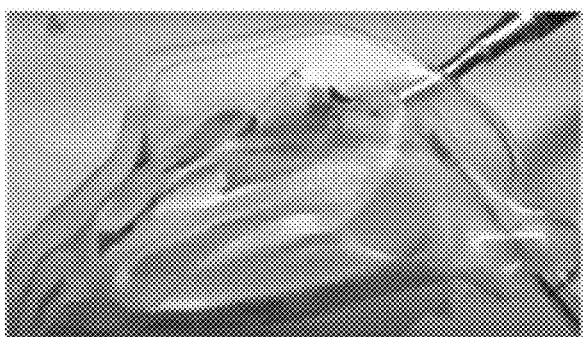
FIGS. 28A-28C depict representative deposition. (A) Maximal middle turbinate surface area coverage with minimal overshooting. (B) Slight overshooting. (C) Considerable off-target deposition.
Figure 28B:
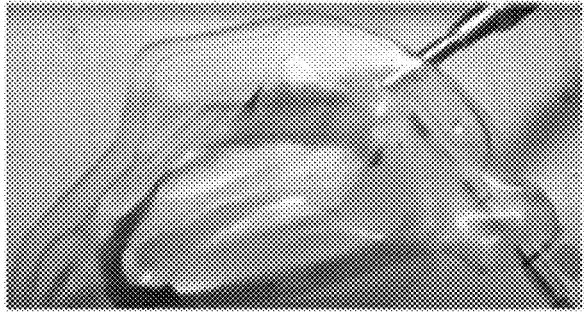
Figure 28C:
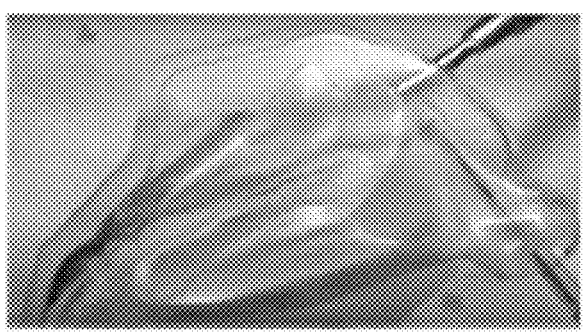

Nasal Model Testing Method:
    Stage 1: Initial screening of cannula designs to assess deposition performance and classify results (Class 1, Class 2, Class 3).
    Stage 2: Repeatability testing (conducted only for 1 cP).
    Stage 3: Sensitivity testing to evaluate deposition across different insertion angles (30° and) 40°.
    Stage 4: Quantitative analysis using a sectioned nasal model to measure deposition in distinct regions.
    Assessment: Results from non-sectional model were primarily visual, with images captured from side and front views to aid in qualitative assessments and down-selection of designs. Quantitative measurements were taken using a sectioned nasal model to calculate fluid distribution in different regions.
    Qualitative Evaluation Criteria: The deposition results for each cannula were categorized into three levels: (1) Class 1: Maximal middle turbinate surface area coverage with minimal overshooting (FIG. 28A). (2) Class 2: Slight overshooting but acceptable deposition (FIG. 28B). (3) Class 3: Considerable off-target deposition (FIG. 28C).

Example 5—Effects of Slit-Cut Shapes in Cannula on Velocity, Droplet Behavior, and Dispersal Angle of the Ejected Fluid in Open Space Ejection Purpose: The purpose of this study was to evaluate how the length and width of slit-cut shapes in cannula influence the velocity, droplet behavior, and dispersal angle of ejected fluid. The side and top views of the ejection provide complementary perspectives: Side view for predicting the spread and penetration of the fluid along the nasal cavity. Top view for highlighting the dispersal angle, indicating how the fluid disperses laterally to reach broader surfaces.

This study followed generally the experimental plan described in Example 4.

Results:

Impact of Cannula Geometry on Velocity and Droplet Behavior: Narrower widths (e.g. 0.3 mm) resulted in higher velocities due to fluid constriction, producing a concentrated spray. They produced smaller, focused droplets. Higher velocity increased shear forces, leading to finer droplet formation. Wider widths (e.g. 1.3 mm) resulted in lower velocities due to reduced constriction, leading to broader dispersion. They produced droplets and a broader spray pattern. Lower velocity allowed droplets to coalesce, increasing their size. The shortest length (3 mm) produced the highest velocities due to minimal resistance along the short path. It resulted in smaller droplets when paired with narrow widths but more focused coverage overall. The longest length (12 mm) produced the lowest velocities. It resulted in larger droplets and broader dispersion, supporting wider surface coverage.

Dispersal angle: 3 mm (length)-0.3 mm (width) configuration gave a dispersal angle of 20° (Concentrated delivery, minimal lateral dispersion). 12 mm (length)-0.3 mm (width) configuration gave a dispersal angle of 41° (Slightly broader coverage). 3 mm (length)-1.3 mm (width) configuration gave a dispersal angle of 69° (Broad lateral dispersion). 12 mm (length)-1.3 mm (width) configuration gave a dispersal angle of 73° (Widest dispersion, maximal surface coverage).

Spread and Penetration: Wider and longer configurations (e.g., 12 mm (length)-1.3 mm (width)) demonstrated broader lateral spread, suggesting that these designs can maximize surface area coverage in the nasal cavity.

Top View (Dispersal Angle): Wider plume angles, as seen in configurations like 12 mm (length)-1.3 mm (width) (73°), suggest the fluid's ability to disperse laterally for coverage of the turbinate surfaces. Narrow dispersal angles, such as 3 mm (length)-0.3 mm (width) (20°), offer focused delivery. Side View (Spread and Penetration): Greater spread observed in longer and wider configurations, such as 12 mm (length)-1.3 mm (width), supports the idea of fluid reaching deeper and broader regions of the turbinates. Narrower configurations like 3 mm (length)-0.3 mm (width) deliver high volumetric flow rate (9 ml/s) and are more focused, but potentially reduces surface area coverage.

Role of Geometry in Maximizing Surface Area:

Slits with longer lengths and wider widths promote fluid dispersion, as evidenced by broader dispersal angles and droplet spread in open space. In a nasal cavity, configurations with larger dispersal angles and more side-to-side spread may increase coverage of the turbinate surface.

Relationship Between Volumetric Flow Rate, Dispersal Angle, and Surface Area:

High volumetric flow rate (e.g., 3 mm (length)-0.3 mm (width)) will facilitate penetration but may reduce lateral coverage. Lower volumetric flow rate with broader dispersion (e.g., 12 mm (length)-1.3 mm (width)) may be more suited for applications requiring extensive surface area coverage Summary: (1) Narrower widths and shorter lengths produce focused sprays with high penetration but reduce lateral coverage. (2) Wider widths and longer lengths achieve broad dispersion with wider dispersal angles, and can maximize turbinate surface coverage. (3) The combined top and side views show that configurations like 12 mm (length)-1.3 mm (width) can maximize fluid distribution for covering the nasal turbinates.

Conclusion: Wide dispersal angles and broad lateral spread observed in open space testing indicate that configurations like 12 mm (length)-1.3 mm (width) (73-degree dispersal angle) can maximize turbinate surface coverage. Smaller cut configurations (e.g., 3 mm (length)-0.3 mm (width)) provide high volumetric flow rate and may be suited for targeted delivery rather than broad dispersion. Longer lengths and wider widths can maximize fluid delivery to the nasal turbinates by achieving both lateral and axial coverage.

Example 6—Effects of Length, Width, and Slit Geometry in Nasal Cavity Model, 1 cP (Stage 1)

Purpose: The purpose of this testing was to evaluate how the length, width, and slit geometry of 30 cannulas can influence fluid deposition performance in an average nasal cavity model. The tests aimed to determine which cannula designs provide the best middle turbinate coverage with minimal overshooting at three volumetric flow rates (7.2, 8.6 and 10.0 ml/s) and two insertion depths (20 mm and 32.5 mm). The assessment focused on achieving maximum middle turbinate coverage with minimal overshooting, using qualitative evaluations to categorize deposition results into Class 1, Class 2, and Class 3 classifications.

Methods: A total of 30 cannulae were tested with varying slit lengths, widths, and angles, along with in-line hole geometries. The testing was conducted at an insertion angle of 35° angle, ejecting 100 μL of 1 cP fluid for each test. Volumetric flow rates of 7.2, 8.6 and 10.0 ml/s were evaluated for each configuration. Special geometries included in-line holes (3 inline holes, 5 inline holes), and quadrilateral transitions (e.g., 12 mm (length)-0.3 mm→1.3 mm (width), 12 mm (length)-1.3 mm→0.3 mm (width)). Refer to Example 4 for cannula design and variations, insertion depths, evaluation criteria.

Results:

Insertion Depths: 32.5 mm depth achieved superior middle turbinate coverage and frequently outperformed 20 mm depth configurations in reducing off-target deposition. 20 mm depth resulted in deposition toward the lower turbinate, nasal floor, or nasopharynx, limiting middle turbinate coverage.

Volumetric flow rates of 7.2-8.6 ml/s provided better control and coverage with reduced overshooting. Volumetric flow rate of 10.0 ml/s frequently resulted in overshooting, though this may differ in mucus-covered conditions where drag is higher.

Cannula Geometry: Longer slit lengths contributed to better surface area coverage by generating tangential fluid flow. Wider slit widths dispersed fluid effectively across the target area, improving coverage. Offset Angles (20°) showed more overshooting compared to 0° offsets, with little improvement in deposition. In-Line Holes directed fluid toward the nasal floor, resulting in poor performance overall.

Discussion: (1) Longer slit lengths (e.g., 12 mm) facilitate tangential fluid flow, improving deposition along the nasal cavity surfaces. (2) Wider slit widths (e.g., 1.3 mm) enhance surface area coverage by increasing lateral dispersion. (3) 32.5 mm insertion depth and moderate volumetric flow rates of (7.2-8.6 ml/s) offer the most effective configurations for middle turbinate coverage.

Example 7—Repeatability of Nasal Cast Depositions, 1 cP (Stage 2)

Purpose: The purpose of Stage 2 was to confirm the repeatability of deposition of selected cannulas from Example 6 (Stage 1). Each cannula was tested three times under identical conditions, with qualitative assessments used to evaluate the consistency of deposition results, again categorized into Class 1, Class 2, and Class 3. Refer to Example 4 for cannula design and variations, insertion depths, evaluation criteria.

Results:

Among the 21 cannulas tested: Majority of the cannulas achieved consistent results across all trials (Repeatable). A few cannulas demonstrated variability, particularly at higher volumetric flow rates (Non-repeatable).

Class 1: Cannulas such as 6 mm (length)-0.75 mm (width)-0° (offset angle), 9 mm (length)-0.51 mm (width)-0° (offset angle), and 12 mm (length)-1.3 mm (width)-0° (offset angle) consistently achieved Class 1 status across trials.

Class 2 Classification: Some configurations, including 9 mm (length)-1 mm (width)-0° and 12 mm (length)-0.75 mm-0° (offset angle), showed slight overshooting but acceptable deposition.

Class 3: None.

Insights from Testing Volumetric Flow Rates: 6.7 and 8.7 ml/s achieved consistent results for most cannulas. 10.0 ml/s occasionally resulted in slight overshooting but remained within acceptable bounds for many configurations.

Discussion: Cannulas consistently meet "Class 1" criteria and demonstrate strong repeatability and reliable performance under identical conditions.

Example 8—Insertion Angle Sensitivity, 1 cP (Stage 3)

Purpose: The purpose of this study was to evaluate the sensitivity of fluid deposition performance across different insertion angles (30° and) 40° for the selected cannulas and to identify designs that can maintain consistent performance across both angles, ensuring reliable deposition regardless of insertion variability.

Refer to Example 4 for cannula design and variations, insertion depths, evaluation criteria.

Methods: A total of 14 cannulas were chosen based on their repeatability and "Class 1" classification in previous stages. Human factors data showed that most patients insert the device at angles less than 40. Each cannula was tested at two insertion angles: 30° and 40° angle. Deposition performance at each angle was evaluated across three volumetric flow rates: 6.7 ml/s, 8.7 ml/s, and 10.0 ml/s. Each angle-volumetric flow rate combination was assessed qualitatively to categorize deposition (see Example 4). The classification combinations are defined as follows:

Class 1-Class 1: Good deposition at both 30° and 40° angles.

Class 1-Class 2: Good deposition at 30° but slight overshooting at 40°.

Class 1-Class 3: Good deposition at 30° but poor deposition at 40°.

Class 3-Class 1: Poor deposition at 30° but good deposition at 40°.

Class 2-Class 3: Slight overshooting at 30° and poor deposition at 40°.

Results:

30° Angle: Most cannulas achieved "Class 1" classifications, showing good deposition with minimal overshooting. Wider widths (e.g., 1.3 mm) and longer lengths (e.g., 12 mm) performed consistently well.

40° Angle: Some cannulas transitioned to "Class 2" or "Class 3" classification, indicating sensitivity to steeper angles. Narrower widths and shorter lengths showed greater variability at this angle.

Class 1-Class 1: Cannulas like 12 mm (length)-1.3 mm (width)-0° (offset angle) and 9 mm (length)-0.75 mm (width)-0° (offset angle) maintained consistent good deposition at both 30° and 40°.

Class 1-Class 2: Cannulas like 9 mm (length)-1 mm (width)-0° (offset angle) performed well at 30° but showed slight overshooting at 40°.

Class 1-Class 3: Designs like 6 mm (length)-0.75 mm (width)-0° (offset angle) achieved good deposition at 30° but failed at 40°, with significant overshooting.

Class 3-Class 1: Designs like 6 mm (length)-0.51 mm (width)-0° (offset angle) showed overshooting at 30° but improved performance at 40°.

Class 2-Class 3: Few cannulas, such as 9 mm (length)-0.3 mm (width)-0° (offset angle), exhibited slight overshooting at 30° and poor deposition at 40°.

Discussion: Lower insertion angles, such as 30° (from the vertical), consistently resulted in better deposition performance across most cannulas. Higher insertion angles, such as 40° (from the vertical), introduced more variability, with some designs showing overshooting or reduced coverage. Wider slit widths (0.75 mm-1.3 mm) and longer slit lengths (9 mm-12 mm) were less sensitive to angle variations, maintaining "Class 1" performance across both angles. Shorter and narrower designs were more likely to exhibit overshooting at higher angles.

Example 9—Quantitative Assessment, 1 cP (Stage 4)

Purpose: The purpose of Stage 4 was to quantify fluid distribution across different regions of the nasal cavity using a sectioned nasal model. This stage aimed to validate the effectiveness of cannula designs in targeting the middle turbinates (key target) while minimizing deposition in off-target areas such as the nasal floor, olfactory, nasal valve, and nasopharynx.

Refer to Example 4 for cannula design and variations, insertion depths, evaluation criteria.

Methods: Cannulas from Stage 3 (Example 8) were selected based on their Class 1-Class 1, Class 1-Class 2, or similar classifications. A sectioned nasal model was used for fluid deposition analysis, divided into five distinct regions: nasal floor (1), nasal valve (2), olfactory region (3), middle turbinate (4), and nasopharynx (5) (See FIG. 24). A high-precision weighing scale was used to measure fluid mass before and after ejection in each region. The following were recorded: (1) Mass of fluid in the device (pre- and post-ejection); (2) Mass of fluid deposited in each nasal region (pre- and post-ejection); and (3) Residual mass percentage in the device after ejection. Based on these measurements, the percentage of ejected fluid deposited in each region of the nasal model was determined. Testing was performed at a 35° angle and three different ejection volumetric flow rates: 6.7 ml/s, 8.7 ml/s, and 10.0 ml/s.

Results:

The middle turbinates received the highest fluid deposition, with an average of 91.54%, confirming strong performance in targeting this key region. Top-performing cannulas (e.g., 12 mm (length)-1.3 mm (width)-0° (offset angle)) achieved deposition values exceeding 99.22% (See Table 1).

Off-Target Regions: Nasal floor and olfactory region had minimal deposition, averaging 0.28% and 0.07%, respectively, indicating precise fluid targeting. The nasopharynx exhibited greater variability, with deposition reaching 24.65% in certain configurations, primarily at higher velocities.

TABLE 1

| Deposition at different regions (1 cP) | | | |
|---|---|---|---|
| Region | Average (%) | Min (%) | Max (%) |
| Middle Turbinates (4) | 91.54 | 74.48 | 99.22 |
| Nasal Floor (1) | 0.28 | 0.00 | 4.62 |
| Nasal Valve (2) | 3.01 | 0.17 | 13.45 |
| Olfactory Region (3) | 0.07 | 0.00 | 0.78 |
| Nasopharynx (5) | 5.10 | 0.00 | 24.65 |

Discussion: The middle turbinates consistently showed the highest deposition. Minimal fluid presence was found in the nasal floor and olfactory region. Lower volumetric flow rates: (6.7 ml/s, 8.7 ml/s) provided optimal deposition, reducing off-target deposition. Higher volumetric flow rates (10.0 ml/s) led to increased deposition in the nasopharynx for certain designs. Cannulas with wider slit widths (1.3 mm) and longer slit lengths (12 mm) consistently achieved high turbinate deposition while minimizing off-target fluid.

Example 10—20 cP Testing (Stages 1, 3 and 4)

The purpose of the 20 cP testing was to: (1) Evaluate the fluid deposition behavior of higher-viscosity fluid (20 cP) across specific stages and device configurations. (2) Compare the results of 20 cP fluid with 1 cP fluid, focusing on similarities and differences in turbinate coverage, and off-target deposition. (3) To quantitatively evaluate fluid deposition in a sectioned nasal model for 20 cP fluid, focusing on fluid distribution in different areas.

Refer to Example 4 for cannula design and variations, insertion depths, evaluation criteria.

Methodology: (1) Stages Tested: Stage 1: Initial deposition testing. Stage 3: Sensitivity across insertion angles (30° and) 40°. Stage 4: Quantitative fluid distribution using a sectioned nasal model. Stage 2 was not tested, as repeatability was validated in 1 cP testing (Example 9). (2) Cannulas Selected: (i) 3 mm (length)-0.3 mm (width)-0° (offset angle); (ii) 3 mm (length)-1.3 mm (width)-0° (offset angle); (iii) 9 mm (length)-1 mm (width)-0° (offset angle); (iv) 9 mm (length)-1.3 mm (width)-0° (offset angle); (v) 12 mm (length)-0.3 mm (width)-0° (offset angle); (vi) 12 mm (length)-1 mm (width)-0° (offset angle); (vii) 12 mm (length)-1.3 mm (width)-0° (offset angle); (viii) 12 mm (length)-1 mm (width)-0° (offset angle) (3 mm distance); (ix) (quadrilateral slit) 12 mm (length)-0.3 mm to 1.3 mm (width)-0° (offset angle); and (x) (quadrilateral slit) 12 mm (length)-1.3 mm to 0.3 mm (width)-0° (offset angle). (3)

Volumetric flow rates: 7.2 ml/s and 10.0 ml/s (this covers the upper and lower bound). (4) Insertion depth: 32.5 mm (20 mm was eliminated from the 1 cP testing); (5) Angle: 0° offset (20 degree offset was eliminated in 1 cP testing-overshooting dose). (6) Visual assessments with high-speed camera from the side and a normal camera capturing from the front part (looking towards the turbinates).

Figure 29A:
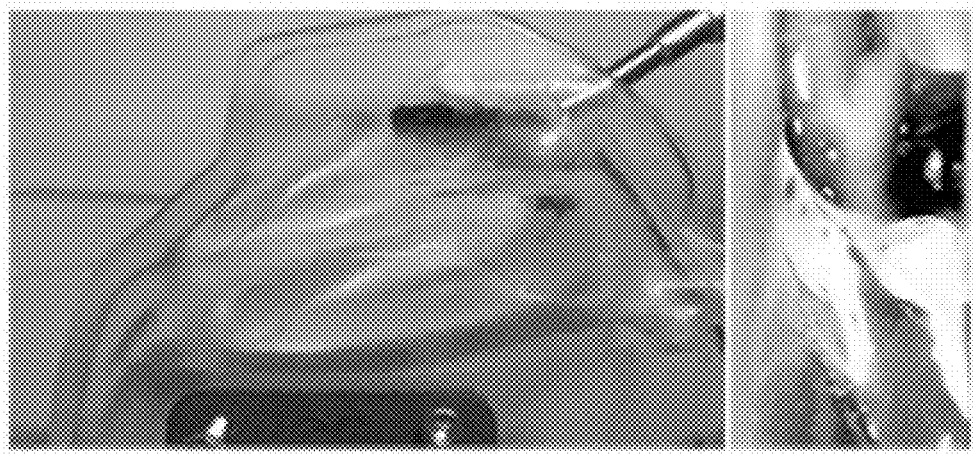
FIGS. 29A-29B depict deposition of a 20 cP (A) and a 1 cP (B) liquid according to some embodiments.
Figure 29B:
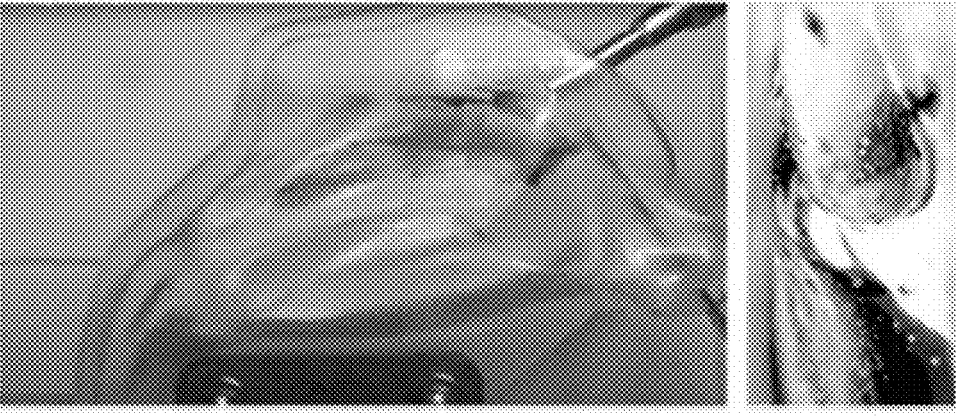

Results:

Stage 1: 20 cP fluid showed effective turbinate coverage with localized deposition, slightly reduced compared to 1 cP. 12 mm (length)-0.3 mm to 1.3 mm (width)-0° (offset angle) (Quadrilateral slit shape) and 12 mm (length)-1.3 mm (width)-0° (offset angle) (FIGS. 29A-29B) demonstrated consistent turbinate coverage with minimal off-target deposition. 3 mm (length)-0.3 mm (width)-0° (offset angle) was eliminated (Class 3 classification) due to poor turbinate coverage and significant overshooting.

Stage 3: Most cannulas performed consistently across 30° and 40° insertion angles.

Stage 4: Middle turbinate coverage remained consistent averaging 90.27% across all configurations. 12 mm (length)-1.3 mm (width)-0° (offset angle) achieved maximum coverage of 96.93%. 12 mm (length)-0.3 mm to 1.3 mm (width)-0° (offset angle) (Quadrilateral slit shape) showed similarly high performance with localized coverage.

Off-Target Deposition: Nasal Valve: Average 9.39%, max 21.28%. Nasal Floor: No measurable deposition (0%). Olfactory Region: No measurable deposition (0%). Nasopharynx: Average 0.33%, indicating good deposition control.

TABLE 2

| Deposition at different regions (20 cP) | | | |
|---|---|---|---|
| Region | Average (%) | Min (%) | Max (%) |
| Middle Turbinates (4) | 90.27 | 78.72 | 96.93 |
| Nasal Floor (1) | 0.00 | 0.00 | 0.00 |
| Nasal Valve (2) | 9.39 | 1.32 | 21.28 |
| Olfactory Region (3) | 0.00 | 0.00 | 0.00 |
| Nasopharynx (5) | 0.33 | 0.00 | 2.40 |

Discussion: 20 cP fluid showed reduced spread compared to 1 cP, with slightly lower turbinate coverage but reduced overshooting. Most cannulas performed consistently across 30° and 40° angles, with only slight variability at higher angles. 20 cP fluid achieved effective turbinate deposition compared to 1 cP. Cannulas including 12 mm (length)-1.3 mm (width)-0° (offset angle) and 12 mm (length)-0.3 mm to 1.3 mm (width)-0° (offset angle) demonstrated consistent results across both viscosities (1 cP and 20 cP).

ENUMERATED EMBODIMENTS

Enumerated Embodiment 1. A device for intranasal delivery to a subject, the device comprising:
    (a) a housing defining an insertable portion configured for insertion into a nasal channel of the subject, the insertable portion comprising a distal end, and a proximal end;
    (b) a subject engaging portion coupled to the proximal end of the insertable portion, the subject engaging portion for engaging a columella region of the subject, thereby seating the insertable portion such that the distal end of the insertable portion is positioned within an ejection zone of the nasal channel of the subject, wherein the ejection zone is:

(i) 0 mm to 30 mm superior to a horizontal line that intersects the anterior aspect of the internal nasal valve, and (ii) 0 mm to 20 mm anterior to an inclined line that intersects the anterior aspect of the middle turbinate and the posterior aspect of the vestibule.

Enumerated Embodiment 2. A device for intranasal delivery to a subject, the device comprising an insertable portion comprising a distal end, and a proximal end, wherein the device is configured to seat the distal end of the insertable portion within an ejection zone of a nasal channel of the subject, wherein the ejection zone is superior to an internal nasal valve, and wherein delivery from the insertable portion of the device is configured to selectively target a lower nasal region.

Enumerated Embodiment 3. The device of any of the preceding enumerated embodiments, further comprising a subject engaging portion coupled to the proximal end of the insertable portion, the subject engaging portion for engaging a columella region of the subject, thereby seating the distal end of the insertable portion within the ejection zone.

Enumerated Embodiment 4. The device of any of the preceding enumerated embodiments, wherein the insertable portion comprises a dispensing element for delivery of a composition to a region or sub-region of the nasal channel of the subject.

Enumerated Embodiment 5. The device of any of the preceding enumerated embodiments, wherein the dispensing element is configured to reveal from the insertable portion upon applying pressure to the columella region of the subject with the subject engaging portion of the device.

Enumerated Embodiment 6. The device of any of the preceding enumerated embodiments, wherein the region or sub-region comprises one or more turbinates.

Enumerated Embodiment 7. The device of any of the preceding enumerated embodiments, wherein the region or sub-region comprises a superior turbinate Enumerated Embodiment 8. The device of any of the preceding enumerated embodiments, wherein the region or sub-region comprises a middle turbinate.

Enumerated Embodiment 9. The device of any of the preceding enumerated embodiments, wherein the region or sub-region comprises an inferior turbinate.

Enumerated Embodiment 10. The device of any of the preceding enumerated embodiments, wherein the region or sub-region comprises the middle meatus.

Enumerated Embodiment 11. The device of any of the preceding enumerated embodiments, wherein the region or sub-region comprises the nasopharynx.

Enumerated Embodiment 12. The device of any one of the preceding claims, wherein the device is configured to limit delivery to an off-target region.

Enumerated Embodiment 13. The device of any one of the preceding claims, wherein the off-target region comprises an olfactory region, a turbinate region, a nasopharynx region, a nasal channel floor region, or a combination thereof.

Enumerated Embodiment 14. The device of any one of the preceding claims, wherein the device is configured to dispense a fluid as a laminar flow.

Enumerated Embodiment 15. The device of any of the preceding enumerated embodiments, wherein the ejection zone is:

i. 0 mm to 30 mm superior to a horizontal line that intersects the anterior aspect of the internal nasal valve, and ii. 0 mm to 20 mm anterior to an inclined line that intersects the anterior aspect of the middle turbinate and the posterior aspect of the vestibule.

Enumerated Embodiment 16. The device of any of the preceding enumerated embodiments, wherein the ejection zone is further:

i. 0 mm to 40 mm inferior to a horizontal line that is parallel to the inferior aspect of the olfactory cleft, ii. 0 mm to 20 mm posterior to the internal nasal dorsum, iii. 10 mm to 50 mm superior to a horizontal line that intersects the inferior aspect of the columella, iv. 0 mm to 30 mm superior to a horizontal line that intersects the superior aspect of the inferior turbinate, v. 0 mm to 3 mm from the septum, or vi. any combination thereof.

Enumerated Embodiment 17. The device of any of the preceding enumerated embodiments, wherein the housing further comprises a second insertable portion for insertion into a second nasal channel of the user.

Enumerated Embodiment 18. The device of any one of the preceding claims, wherein the dispensing element comprises a side opening.

Enumerated Embodiment 19. The device of any of the preceding enumerated embodiments, wherein the dispensing element is configured to dispense the composition from a side opening.

Enumerated Embodiment 20. The device of any one of the preceding claims, wherein the device is configured to deliver at least 70%, at least 80%, at least 90%, or at least 95% of the composition ejected from the side opening to the middle turbinate.

Enumerated Embodiment 21. The device of any one of the preceding claims, wherein the device is configured to deliver at most 30%, at most 20%, at most 10%, or at most 5% of the composition ejected from the side opening to the nasopharynx.

Enumerated Embodiment 22. The device of any one of the preceding claims, wherein the composition is a liquid composition.

Enumerated Embodiment 23. The device of any one of the preceding claims, wherein the dispensing element is configured such that, when said dispensing element is revealed from the insertable portion within the ejection zone, the side opening can dispense the composition towards the nasal cavity away from the internal nasal dorsum.

Enumerated Embodiment 24. The device of any one of the preceding claims, wherein the device is configured such that, when the dispensing element is revealed from the insertable portion within the ejection zone, the side opening is positioned about 15 to 35 mm from a columella datum.

Enumerated Embodiment 25. The device of any one of the preceding claims, wherein the device is configured such that, when the dispensing element is revealed from the insertable portion within the ejection zone, the side opening is positioned about 10 to 60 mm from a columella datum.

Enumerated Embodiment 26. The device of any one of the preceding claims, wherein the dispensing element is configured such that, when said dispensing element is revealed from the insertable portion within the ejection zone, the side opening comprises an offset angle of about 0°.

Enumerated Embodiment 27. The device of any one of the preceding claims, wherein the device is configured such that the insertable portion is capable of being inserted into a nasal channel of the subject at an insertion angle.

Enumerated Embodiment 28. The device of any one of the preceding claims, wherein the insertion angle is between about 25° and about 45°.

Enumerated Embodiment 29. The device of any one of the preceding claims, wherein the side opening comprises a generally elongate shape.

Enumerated Embodiment 30. The device of any one of the preceding claims, wherein the side opening comprises a generally quadrilateral shape.

Enumerated Embodiment 31. The device of any one of the preceding claims, wherein the side opening comprises a length between a distal end and a proximal end that generally aligns with a longitudinal axis of the dispensing element.

Enumerated Embodiment 32. The device of any one of the preceding claims, wherein the length of the side opening is substantially the length of the dispensing element revealed from the insertable portion upon actuation.

Enumerated Embodiment 33. The device of any one of the preceding claims, wherein the length of the side opening is shorter than the length of the dispensing element revealed from the insertable portion upon actuation.

Enumerated Embodiment 34. The device of any one of the preceding claims, wherein the length of the side opening is at least about 50%, at least about 60%, at least about 70%, at least about 80%, or at least about 90% of the length of the dispensing element revealed from the insertable portion upon actuation.

Enumerated Embodiment 35. The device of any one of the preceding claims, wherein the side opening comprises a length from about 2 mm to about 15 mm.

Enumerated Embodiment 36. The device of any one of the preceding claims, wherein the side opening comprises a length from about 6 mm to about 12 mm.

Enumerated Embodiment 37. The device of any one of the preceding claims, wherein the side opening comprises a width of between about 20% and about 99% of a width of the dispensing element.

Enumerated Embodiment 38. The device of any one of the preceding claims, wherein the side opening comprises a width of between about 0.2 mm and about 1.5 mm.

Enumerated Embodiment 39. The device of any one of the preceding claims, wherein the side opening comprises an area of between about 0.5 mm$^2$ and about 20 mm$^2$.

Enumerated Embodiment 40. The device of any one of the preceding claims, wherein the composition has a viscosity of between about 0.5 cP and about 50 cP.

Enumerated Embodiment 41. The device of any one of the preceding claims, wherein the device is configured to eject the composition from the side opening at a volumetric flow rate of between about 1.5 ml/s and about 20 ml/s.

Enumerated Embodiment 42. The device of any one of the preceding claims, wherein the device is configured to eject the composition from the side opening at a volumetric flow rate of between about 5 ml/s and about 12 ml/s.

Enumerated Embodiment 43. The device of any one of the preceding claims, wherein the device is configured to eject the composition from the side opening at a volumetric flow rate of greater than 12 ml/s.

Enumerated Embodiment 44. The device of any one of the preceding claims, wherein the device is configured to eject a fluid at a velocity selected for focusing of deposition.

Enumerated Embodiment 45. The device of any one of the preceding claims, wherein the device is configured to eject a fluid at a velocity selected for a desired deposition profile.

Enumerated Embodiment 46. The device of any one of the preceding claims, wherein the device is configured to eject a fluid at a velocity selected for bolus deposition, surface coating deposition, or droplet deposition Enumerated Embodiment 47. The device of any one of the preceding claims, wherein the at least one insertable portion that opens or expands an internal nasal valve does so by moving a superior lateral cartilage defining the internal nasal valve away from a septum of the subject.

Enumerated Embodiment 48. The device of any one of the preceding claims, wherein the at least one insertable portion that opens or expands an internal nasal valve does so by moving superior lateral cartilage defining the internal nasal valve towards an internal nasal dorsum of the subject.

Enumerated Embodiment 49. The device of any one of the preceding claims, wherein the insertable portion, upon insertion into a nasal channel of the subject, is proximal to the septum.

Enumerated Embodiment 50. The device of any one of the preceding claims, wherein the subject engaging portion prevents movement of the distal end within or away from the ejection zone when the subject engaging portion is seated on the columella region.

Enumerated Embodiment 51. The device of any one of the preceding claims, wherein dispensing a composition from the ejection zone increases on target deposition of the composition to two or more regions or sub-regions of a nasal channel.

Enumerated Embodiment 52. The device of any one of the preceding claims, wherein the subject engaging portion is seated against the columella region when the subject engaging portion simultaneously contacts a downward facing lateral face of the columella, a leftward facing lateral face of the columella, and a rightward facing lateral face of the columella.

Enumerated Embodiment 53. The device of any one of the preceding claims, wherein the subject engaging portion limits a depth of insertion of the insertable portion into the nasal channel.

Enumerated Embodiment 54. The device of any one of the preceding claims, wherein the insertable portion incorporates one or more dispensing channels leading to one or more dispensing ports configured for delivery of a composition to one or more regions or sub-regions of the nasal channel of the subject.

Enumerated Embodiment 55. The device of any one of the preceding claims, wherein the housing comprises a trigger, wherein, the trigger is configured to actuate the device upon application of pressure to the trigger to dispense a composition to the subject from the insertable portion or the dispensing element.

Enumerated Embodiment 56. The device of any one of the preceding claims, wherein the subject engaging portion comprises a trigger coupled to the housing and the subject engaging portion, wherein the trigger is configured to actuate the device upon application of pressure of the subject engaging portion to the columella region to dispense a composition to the subject from the insertable portion or the dispensing element.

Enumerated Embodiment 57. The device of any one of the preceding claims, wherein the device is transitionable from a first configuration to a second configuration.

Enumerated Embodiment 58. The device of any one of the preceding claims, wherein at least one dispensing element is configured to reveal from at least one insertable portion upon transition of the device from the first configuration to the second configuration.

Enumerated Embodiment 59. The device of any one of the preceding claims, wherein the device is transitionable from the first configuration to the second configuration upon application of pressure along a longitudinal axis of the device.

Enumerated Embodiment 60. The device of any one of the preceding claims, wherein the dispensing element is configured to reveal in a linear vector relative to a longitudinal axis of the insertable portion.

Enumerated Embodiment 61. The device of any one of the preceding claims, wherein the device is configured to be transitioned from the first configuration to the second configuration with only one hand.

Enumerated Embodiment 62. The device of any of the preceding enumerated embodiments, wherein a dispensing element is configured to reveal from a distal end of the insertable portion.

Enumerated Embodiment 63. The device of any of the preceding enumerated embodiments, wherein the revealing of the dispensing element from the insertable portion comprises extending of the dispensing element from the insertable portion.

Enumerated Embodiment 64. The device of any one of the preceding claims, wherein the device is simultaneously actuated upon being transitioned from the first configuration to the second configuration.

Enumerated Embodiment 65. The device of any one of the preceding claims, wherein the device is configured such that the distal aspect of the at least one dispensing element is positioned in the ejection zone when the device is in the second configuration.

Enumerated Embodiment 66. The device of any one of the preceding claims, wherein the dispensing element is configured to reveal from the insertable portion upon transition of the device from the first configuration to the second configuration, upon application of pressure of a portion of the housing to a columella region of a subject.

Enumerated Embodiment 67. The device of any of the preceding enumerated embodiments, wherein the dispensing element is configured to reveal in a linear vector parallel to the internal nasal dorsum from the first insertable portion at a location above an inferior turbinate of the subject.

Enumerated Embodiment 68. The device of any of the preceding enumerated embodiments, wherein the first and second dispensing elements are configured to dispense a composition from the first and second dispensing elements simultaneously.

Enumerated Embodiment 69. The device of any of the preceding enumerated embodiments, wherein the first and second dispensing elements are configured to dispense a composition from the first and second dispensing elements sequentially.

Enumerated Embodiment 70. The device of any of the preceding enumerated embodiments, wherein the two insertable portions are configured such that each contact opposite sides of a septum and apply force to a superior lateral cartilage in a direction away from the septum.

Enumerated Embodiment 71. The device of any of the preceding enumerated embodiments, wherein the two insertable portions are configured such that each contact opposite sides of a septum and apply force to a superior lateral cartilage in a direction orthogonal to a lateral axis of the septum.

Enumerated Embodiment 72. The device of any of the preceding enumerated embodiments, wherein the insertable portion is configured to fit into a wedge shape of a nasal valve where a septum contacts a superior lateral cartilage.

Enumerated Embodiment 73. The device of any of the preceding enumerated embodiments, wherein the anterior aspect of the insertable portion is configured to fit into the narrow anterior aspect of the internal nasal valve.

Enumerated Embodiment 74. The device of any of the preceding enumerated embodiments, wherein the anterior aspect of the insertable portion is configured to fit into an opening comprising a 9 to 15 degree angle with reference to the septum wall.

Enumerated Embodiment 75. The device of any of the preceding enumerated embodiments, wherein the insertable portion is configured to fit into the narrow anterior aspect of the internal nasal valve when seated about the columella region.

Enumerated Embodiment 76. The device of any of the preceding enumerated embodiments, wherein the insertable portion is configured to fit into an opening comprising a 9 to 15 degree angle with reference to the septum wall when seated about the columella region.

Enumerated Embodiment 77. The device of any of the preceding enumerated embodiments, wherein the insertable portion is tapered about a distal end of the insertable portion and is configured to be inserted into a wedge shaped internal nasal valve of a subject.

Enumerated Embodiment 78. The device of any of the preceding enumerated embodiments, wherein the insertable portion comprises a tip portion having a width which corresponds to an average diameter of an internal nasal valve.

Enumerated Embodiment 79. The device of any of the preceding enumerated embodiments, wherein the insertable portion comprises a flat surface on a lateral face of the insertable portion which contacts the septum.

Enumerated Embodiment 80. The device of any of the preceding enumerated embodiments, wherein the insertable portion comprises a rounded surface on a lateral face of the insertable portion which is opposite the septum.

Enumerated Embodiment 81. The device of any of the preceding enumerated embodiments, wherein the insertable portion comprises a width up to about 3 mm.

Enumerated Embodiment 82. The device of any of the preceding enumerated embodiments, wherein the subject engaging portion is configured to engage both a right side and a left side of the columella region.

Enumerated Embodiment 83. The device of any of the preceding enumerated embodiments, wherein the subject engaging portion comprises a concave shape.

Enumerated Embodiment 84. The device of any of the preceding enumerated embodiments, wherein the subject engaging portion comprises a U shape.

Enumerated Embodiment 85. The device of any of the preceding enumerated embodiments, wherein the subject engaging portion comprises a saddle shape.

Enumerated Embodiment 86. The device of any of the preceding enumerated embodiments, wherein the subject engaging portion comprises a saddle shape.

Enumerated Embodiment 87. The device of any of the preceding enumerated embodiments, wherein the subject engaging portion comprises a trench with a rounded bottom or rounded edges.

Enumerated Embodiment 88. The device of any of the preceding enumerated embodiments, wherein the subject engaging portion is a positioning element which aligns at least one of the insertable portion, the dispensing element, or the housing relative to the user's nasal channel.

Enumerated Embodiment 89. The device of any of the preceding enumerated embodiments, wherein an insertable portion comprises a single dispensing channel leading to a dispensing port positioned along the length of the insertable portion.

Enumerated Embodiment 90. The device of any of the preceding enumerated embodiments, wherein an insertable portion comprises two or more dispensing channels leading to two or more dispensing ports positioned at various aspects of the insertable portion.

Enumerated Embodiment 91. The device of any of the preceding enumerated embodiments, wherein the saddle portion, subject engaging portion, or positioning trigger comprises a shape which matches the anatomy of the subject's columella.

Enumerated Embodiment 92. The device of any of the preceding enumerated embodiments, wherein the subject engaging portion comprises dimension of about 20 mm by about 17 mm.

Enumerated Embodiment 93. The device of any of the preceding enumerated embodiments, wherein the first and/or second insertable portion limits a sagittal angle or an anterior-posterior angle of the device.

Enumerated Embodiment 94. The device of any of the preceding enumerated embodiments, wherein the first and/or second insertable portion limits a coronal angle or a medial-lateral angle of the device.

Enumerated Embodiment 95. The device of any of the preceding enumerated embodiments, wherein the first and/or second insertable portion and subject engaging portion limits a sagittal angle, an anterior-posterior angle of the device, a coronal angle or a medial-lateral angle of the device, or any combination thereof.

Enumerated Embodiment 98. The device of any of the preceding enumerated embodiments, wherein the first and/or second insertable portion is torsionally flexible.

Enumerated Embodiment 97. The device of any of the preceding enumerated embodiments, wherein the first and/or second insertable portion comprises dimension of about 20 mm by about 3.5 mm.

Enumerated Embodiment 98. The device of any of the preceding enumerated embodiments, wherein the insertable portion has the following flexibility characteristics:

a) a medial-lateral flexibility along a width orthogonal to a length of the insertable portion;

b) a lack of anterior-posterior flexibility about a length of the insertable portion; or c) an inferior-superior flexibility about a rotational axis orthogonal to a length of the insertable portion.

Enumerated Embodiment 99. The device of any of the preceding enumerated embodiments, wherein a dispensing element comprises a cannula or a catheter.

Enumerated Embodiment 100. The device of any of the preceding enumerated embodiments, wherein the dispensing element has one dispensing port at its distal end, one or more dispensing ports along its length, or a combination of both.

Enumerated Embodiment 101. The device of any of the preceding enumerated embodiments, wherein the one or more dispensing elements are 20 mm to 50 mm in length.

Enumerated Embodiment 102. The device of any of the preceding enumerated embodiments, wherein the one or more dispensing elements reveal 0 mm to 40 mm from the insertable portion.

Enumerated Embodiment 103. The device of any of the preceding enumerated embodiments, further comprising a reservoir fluidically connected to the one or more insertable portions.

Enumerated Embodiment 104. The device of any of the preceding enumerated embodiments, further comprising a reservoir fluidically connected to the one or more dispensing elements.

Enumerated Embodiment 105. The device of any of the preceding enumerated embodiments, wherein the actuator is spring loaded.

Enumerated Embodiment 106. The device of any of the preceding enumerated embodiments, further comprising a central tube fluidically connected to the one or more dispensing elements, wherein the central tube is inserted into the reservoir when the device is actuated.

Enumerated Embodiment 107. The device of any of the preceding enumerated embodiments, wherein the dispensing channels comprise a diameter of about 0.3 mm to about 3 mm.

Enumerated Embodiment 108. The device of any of the preceding enumerated embodiments, wherein the dispensing element comprises an inner diameter of about 0.3 mm to about 3 mm.

Enumerated Embodiment 109. A method for intranasal delivery to a subject with a device, the method comprising:

positioning a dispensing element within an ejection zone of a nasal cavity of the subject; and dispensing a composition from a side opening of the dispensing element, thereby delivering the composition to an intranasal target of the subject.

Enumerated Embodiment 110. The method of any one of the preceding enumerated embodiments, wherein the ejection zone is:

i. 0 mm to 30 mm superior to a horizontal line that intersects the anterior aspect of the internal nasal valve, and ii. 0 mm to 20 mm anterior to an inclined line that intersects the anterior aspect of the middle turbinate and the posterior aspect of the vestibule.

Enumerated Embodiment 111. The method of any of the preceding claims, wherein the ejection zone is further:

i. 0 mm to 40 mm inferior to a horizontal line that is parallel to the inferior aspect of the olfactory cleft, ii. 0 mm to 20 mm posterior to the internal nasal dorsum, iii. 10 mm to 50 mm superior to a horizontal line that intersects the inferior aspect of the columella, iv. 0 mm to 30 mm superior to a horizontal line that intersects the superior aspect of the inferior turbinate, v. 0 mm to 3 mm from the septum, or vi. any combination thereof.

Enumerated Embodiment 112. The method of any one of the preceding enumerated embodiments, wherein positioning the dispensing element within the ejection zone comprises positioning an insertable portion of the device within the ejection zone by engaging a columella region of the subject with a subject engaging portion of the device.

Enumerated Embodiment 113. The method of any one of the preceding enumerated embodiments, wherein the composition is dispensed from the dispensing element at an offset angle of about 0°.

Enumerated Embodiment 114. The method of any one of the preceding enumerated embodiments, wherein positioning the insertable portion of the device within the ejection zone comprises inserting the insertable portion at an insertion angle.

Enumerated Embodiment 115. The method of any one of the preceding enumerated embodiments, wherein the insertion angle is between about 25° and about 45°.

Enumerated Embodiment 116. The method of any one of the preceding enumerated embodiments, wherein at least 70%, at least 80%, at least 90%, or at least 95% of the composition dispensed from the side opening is delivered to the middle turbinate.

Enumerated Embodiment 117. The method of any one of the preceding enumerated embodiments, wherein at most 30%, at most 20%, at most 10%, or at most 5% of the composition dispensed from the side opening is delivered to the nasopharynx.

Enumerated Embodiment 118. The method of any one of the preceding enumerated embodiments, further comprising actuating the device by applying pressure to the columella region of the subject with the subject engaging portion of the device.

Enumerated Embodiment 119. The method of any one of the preceding enumerated embodiments, wherein the positioning the insertable portion of the device comprises positioning two insertable portions into two nasal channels of the subject, thereby opening or expanding an opening of an internal nasal valve of the subject.

Enumerated Embodiment 120. The method of any one of the preceding enumerated embodiments, wherein the positioning the dispensing element of the device comprises positioning two dispensing elements of the device into a nasal channel of the subject, wherein the two dispensing elements reveal from the insertable portion.

Enumerated Embodiment 121. The method of any one of the preceding enumerated embodiments, further comprising transitioning the device from a first configuration to a second configuration, wherein the dispensing element reveals from the insertable portion upon transition of the device from the first configuration to the second configuration.

Enumerated Embodiment 122. The method of any one of the preceding enumerated embodiments, further comprising positioning the insertable portions into nasal channels of the subject by engaging a columella region of the subject with a subject engaging portion of the device, thereby limiting a depth of insertion of the device into the subject's nasal channel and aligning the insertable portions within the nasal channel of the subject.

Enumerated Embodiment 123. The method of any one of the preceding enumerated embodiments, further comprising actuating the device by applying pressure to the subject engaging portion of the device with the columella region of the subject.

Enumerated Embodiment 124. The method of any one of the preceding enumerated embodiments, wherein the two insertable portions comprise at least one dispensing element.

Enumerated Embodiment 125. The method of any one of the preceding enumerated embodiments, wherein the at least one dispensing element reveals outwards from at least one of the two insertable portions.

Enumerated Embodiment 126. The method of any one of the preceding enumerated embodiments, further comprising transitioning the device from a first configuration to a second configuration, wherein the dispensing element reveals from the insertable portion upon transition of the device from the first configuration to the second configuration.

Enumerated Embodiment 127. The method of any one of the preceding enumerated embodiments, wherein the inserting two insertable portions advances the two insertable portions along the inner dorsum and/or on along either side of the septum until a columella engaging region of the device contacts a columella of the subject, preventing further insertion, and establishing a depth datum.

Enumerated Embodiment 128. The method of any one of the preceding enumerated embodiments, wherein the inserting two insertable portions uses the nasofrontal angle as an angular reference to position the insertable portions within the nasal channels.

Enumerated Embodiment 129. The method of any one of the preceding enumerated embodiments, wherein the inserting two insertable portions comprises inserting the two insertable portions past a nasal vestibule.

Enumerated Embodiment 130. The method of any one of the preceding enumerated embodiments, wherein the inserting two insertable portions comprises inserting the two insertable portions along soft tissues of an interior dorsum wall in an orientation parallel to the soft tissues.

Enumerated Embodiment 131. The method of any one of the preceding enumerated embodiments, wherein the inserting two insertable portions prevents rotation of the device about an axis parallel to the subject's height.

Enumerated Embodiment 132. The method of any one of the preceding enumerated embodiments, wherein the inserting two insertable portions creates a yaw angle on a reference coronal plane relative to a y-axis of the device.

Enumerated Embodiment 133. The method of any one of the preceding enumerated embodiments, wherein the inserting two insertable portions creates a substantially unimpeded flow to a nasal turbinate.

Enumerated Embodiment 134. The method of any one of the preceding enumerated embodiments, wherein the simultaneous actuation refers to transition for the first configuration to the second configuration and actuation occurring in a single motion upon application of pressure about a longitudinal axis of the device.

Enumerated Embodiment 135. The method of any one of the preceding enumerated embodiments, wherein the positioning the insertable portion of the device within the nasal channel of the subject occurs by engaging a columella region of the subject with a subject engaging portion of the device.

Enumerated Embodiment 136. The method of any one of the preceding enumerated embodiments, wherein the ejection zone comprises a trapezium or irregular quadrilateral plane comprising (i) an inferior side being a 10-25 mm line extending posteriorly and horizontally from the anterior aspect of the internal nasal valve, (ii) an anterior side being a 10-35 mm line extending superiorly and parallel to the internal nasal dorsum from the anterior aspect of the internal nasal valve, (iii) a superior side being a 10-25 mm line extending posteriorly and horizontally from a point on the internal nasal dorsum that is 0-10 mm inferior to the inferior aspect of the olfactory cleft, and (iv) a posterior line being a 10-35 mm line extending vertically along a plane that intersects the anterior aspect of the middle turbinate.

Enumerated Embodiment 137. The method of any one of the preceding enumerated embodiments, wherein the target region is the middle meatus, and wherein dispensing the composition from a posterior end of the dispensing element increases on target delivery of the composition to the target region.

Enumerated Embodiment 138. The method of any one of the preceding enumerated embodiments, wherein the ejection zone is further: parallel with a middle turbinate of the subject, and not within the middle meatus.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the present disclosure may be employed in practicing the present disclosure. It is intended that the following claims define the scope of the present disclosure and that methods and structures within the scope of these claims and their equivalents be covered thereby.

The invention claimed is:

1. A device for intranasal delivery to a subject, the device comprising:

(a) a housing defining an insertable portion configured for insertion into a nasal channel of the subject, the insertable portion comprising a distal end, and a proximal end; and (b) a subject engaging portion coupled to the proximal end of the insertable portion, the subject engaging portion comprises a U shape and is configured to engage a columella region of the subject by simultaneously contacting a downward facing lateral face of the columella region, a leftward facing lateral face of the columella region, and a rightward facing lateral face of the columella region, thereby seating the insertable portion such that the distal end of the insertable portion is positioned within an ejection zone of the nasal channel of the subject, wherein the ejection zone is:

(i) 0 mm to 30 mm superior to a horizontal line that intersects an anterior aspect of an internal nasal valve, and (ii) 0 mm to 20 mm anterior to an inclined line that intersects an anterior aspect of a middle turbinate and a posterior aspect of a vestibule, wherein the insertable portion comprises a dispensing element for delivery of a composition to a region or sub-region of the nasal channel of the subject, wherein the dispensing element comprises a side opening.

2. The device of claim 1, wherein the device is transitionable from a first configuration to a second configuration, wherein the dispensing element extends from the insertable portion upon transition of the device from the first configuration to the second configuration.

3. The device of claim 2, wherein the side opening comprises a length at least about 10% of a length of the dispensing element extended from the insertable portion in the second configuration.

4. The device of claim 2, wherein application of pressure by the subject engaging portion to the columella region of the subject is configured to actuate the device.

5. The device of claim 1, wherein the dispensing element is extended from the insertable portion, wherein the side opening comprises a length at least about 10% of a length of the dispensing element extended from the insertable portion.

6. The device of claim 1, wherein the side opening comprises a width of at least about 10% and at most about 95% of a width of the dispensing element.

7. The device of claim 1, wherein the side opening comprises a length from about 2 mm to about 15 mm.

8. The device of claim 1, wherein the side opening comprises an opening area of between about 0.2 mm$^2$ and about 50 mm$^2$.

9. The device of claim 1, wherein the device is configured to dispense a fluid as a laminar flow.

10. The device of claim 1, wherein the housing further comprises a second insertable portion for insertion into a second nasal channel of the subject.

11. The device of claim 1, wherein the dispensing element comprises a dispensing channel positioned along a length of the dispensing element, wherein the dispensing channel is positioned off-center along the dispensing element.

12. The device of claim 1, wherein the dispensing element comprises a dispensing channel, wherein the dispensing channel is tapered at a distal end of the dispensing channel.

13. The device of claim 1, wherein the device is configured to eject the composition from the side opening at a volumetric flow rate of between about 1.5 ml/s and about 20 ml/s.

14. The device of claim 1, wherein the region or sub-region of the nasal channel comprises one or more turbinates.

15. The device of claim 1, wherein the region or sub-region of the nasal channel is a superior turbinate, the middle turbinate, an inferior turbinate, a middle meatus, or a nasopharynx.

* * * * *